(12) United States Patent  (10) Patent No.: US 8,431,603 B2
Shibata et al.  (45) Date of Patent: Apr. 30, 2013

(54) **3-PHENYLPYRAZOLO[5,1-*B*]THIAZOLE COMPOUNDS**

(75) Inventors: Hisashi Shibata, Tsukuba (JP); Kodo Shikata, Tsukuba (JP); Akira Inomata, Tsukuba (JP); Kogyoku Shin, Tsukuba (JP); Taro Terauchi, Tsukuba (JP); Yoshinori Takahashi, Tsukuba (JP); Minako Hashizume, Tsukuba (JP); Kunitoshi Takeda, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 91 days.

(21) Appl. No.: 12/421,182

(22) Filed: Apr. 9, 2009

(65) Prior Publication Data

US 2009/0259049 A1  Oct. 15, 2009

Related U.S. Application Data

(60) Provisional application No. 61/045,084, filed on Apr. 15, 2008.

(30) Foreign Application Priority Data

Apr. 15, 2008  (JP) ................ 2008-106080

(51) Int. Cl.
*A61K 31/4439* (2006.01)
*C07D 513/02* (2006.01)

(52) U.S. Cl.
USPC .............................. 514/368; 548/154

(58) Field of Classification Search ........... None
See application file for complete search history.

(56) References Cited

U.S. PATENT DOCUMENTS

| | | |
|---|---|---|
| 4,007,189 A | 2/1977 | Sato et al. |
| 4,596,872 A | 6/1986 | Davey |
| 4,910,199 A | 3/1990 | Bourguignon et al. |
| 4,925,849 A | 5/1990 | Shiokawa et al. |
| 4,957,925 A | 9/1990 | Gubin et al. |
| 4,985,444 A | 1/1991 | Shiokawa et al. |
| 4,990,516 A | 2/1991 | Ohashi et al. |
| 4,992,442 A | 2/1991 | Tsujitani et al. |
| 4,994,453 A | 2/1991 | Shiokawa et al. |
| 5,087,629 A | 2/1992 | Shiokawa et al. |
| 5,102,869 A | 4/1992 | Shiokawa et al. |
| 5,102,878 A | 4/1992 | Shiokawa et al. |
| 5,127,936 A | 7/1992 | Selby |
| 5,155,114 A | 10/1992 | Shiokawa et al. |
| 5,179,103 A | 1/1993 | Shiokawa et al. |
| 5,190,862 A | 3/1993 | Wielinger et al. |
| 5,234,818 A | 8/1993 | Zimmermann et al. |
| 5,296,490 A | 3/1994 | Shiokawa et al. |
| 5,338,743 A | 8/1994 | Shiokawa et al. |
| 5,391,482 A | 2/1995 | Mangold |
| 5,445,943 A | 8/1995 | Hoenes |
| 5,457,200 A | 10/1995 | Zimmermann et al. |
| 5,525,480 A | 6/1996 | Zimmermann et al. |
| 5,565,468 A | 10/1996 | Larsen et al. |
| 5,602,132 A | 2/1997 | Roger et al. |
| 5,691,347 A | 11/1997 | Corbier et al. |
| 5,942,515 A | 8/1999 | Namiki et al. |
| 6,638,933 B2 | 10/2003 | Gerlach et al. |
| 6,642,246 B1 | 11/2003 | Schmiesing |
| 6,657,064 B2 | 12/2003 | Gerlach et al. |
| 6,664,261 B2 | 12/2003 | Chen et al. |
| 6,703,404 B2 | 3/2004 | Maul et al. |
| 6,730,789 B1 | 5/2004 | Birault et al. |

(Continued)

FOREIGN PATENT DOCUMENTS

AU  2003220190 A1  9/2003
CA  2115805 A1  8/1994

(Continued)

OTHER PUBLICATIONS

Altemus et al., "Changes in Cerebrospinal Fluid Neurochemistry During Treatment of Obsessive-Compulsive Disorder With Clomipramine", Arch Gen Psychiatry, vol. 51, Oct. 1994, pp. 794-803.

Arase et al., "Effects of Corticotropin Releasing Factor on Genetically Obese (Fatty) Rats", Psychology & Behavior, vol. 45, 1989, pp. 565-570, Pergamon Press.

(Continued)

*Primary Examiner* — Kamal Saeed
(74) *Attorney, Agent, or Firm* — Birch Stewart Kolasch & Birch, LLP

(57) ABSTRACT

A compound represented by the following formula (I), or salt thereof exhibits excellent CRF receptor antagonism, and sufficient pharmacological activity, safety and pharmacokinetic properties as a drug.

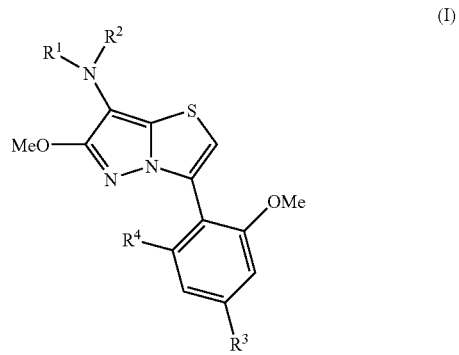

(I)

wherein $R^1$ represents the formula $-A^{11}-A^{12}$; $R^2$ represents tetrahydrofurylmethyl, tetrahydropyranylmethyl or tetrahydropyranyl; $A^{11}$ represents a single bond, methylene or 1,2-ethylene; $A^{12}$ represents C1-6 alkyl, C3-6 cycloalkyl or C3-6 cycloalkyl having methyl; $R^3$ represents methoxy, cyano, cyclobutyloxymethyl, methoxymethyl or ethoxymethyl; and $R^4$ represents methoxy or chlorine.

20 Claims, No Drawings

U.S. PATENT DOCUMENTS

| | | | |
|---|---|---|---|
| 6,849,642 | B2 | 2/2005 | Gerlach et al. |
| 6,936,631 | B2 | 8/2005 | Gerlach et al. |
| 7,074,797 | B2 | 7/2006 | Chen et al. |
| 7,078,405 | B2 | 7/2006 | Hibi et al. |
| 7,091,215 | B2 | 8/2006 | Hibi et al. |
| 7,176,216 | B2 | 2/2007 | Hibi et al. |
| 7,285,666 | B2 | 10/2007 | Hibi et al. |
| 7,323,569 | B2 | 1/2008 | Hibi et al. |
| 7,625,925 | B2 | 12/2009 | Hibi et al. |
| 7,772,249 | B2 | 8/2010 | Hibi et al. |
| 2003/0065187 | A1 | 4/2003 | Buchwald et al. |
| 2004/0019216 | A1 | 1/2004 | Buchwald et al. |
| 2004/0122039 | A1 | 6/2004 | Hibi et al. |
| 2004/0224974 | A1 | 11/2004 | Hibi et al. |
| 2006/0211696 | A1 | 9/2006 | Hibi et al. |
| 2006/0235011 | A1 | 10/2006 | Hibi et al. |
| 2006/0270659 | A1 | 11/2006 | Chen et al. |
| 2007/0129382 | A1 | 6/2007 | Grigoriadis et al. |
| 2007/0293511 | A1 | 12/2007 | Luo et al. |
| 2008/0076943 | A1 | 3/2008 | Hibi et al. |
| 2008/0194589 | A1 | 8/2008 | Lanier et al. |
| 2008/0306092 | A1 | 12/2008 | Hossner |
| 2009/0181985 | A1 | 7/2009 | Hibi et al. |
| 2009/0259049 | A1 | 10/2009 | Shibata et al. |

FOREIGN PATENT DOCUMENTS

| | | |
|---|---|---|
| CN | 100338063 C | 9/2007 |
| CN | 101081850 A | 12/2007 |
| CN | 101081853 A | 12/2007 |
| EP | 0068378 A1 | 1/1983 |
| EP | 0 299 209 A2 | 1/1989 |
| EP | 0347252 A2 | 12/1989 |
| EP | 0 368 343 A2 | 5/1990 |
| EP | 0369145 A2 | 5/1990 |
| EP | 0433853 A1 | 6/1991 |
| EP | 0433854 A2 | 6/1991 |
| EP | 0 497 258 A2 | 8/1992 |
| EP | 0611766 A1 | 8/1994 |
| EP | 0659747 A1 | 6/1995 |
| EP | 0778277 A1 | 6/1997 |
| EP | 0812831 A1 | 12/1997 |
| EP | 1389618 A1 | 2/2004 |
| EP | 1 555 265 A1 | 7/2005 |
| EP | 2266990 A1 | 12/2010 |
| HU | 211684 A9 | 12/1995 |
| IN | 237668 | 1/2010 |
| IN | 246359 | 2/2011 |
| JP | 46-31228 A | 9/1971 |
| JP | 50-11399 | 4/1975 |
| JP | 2-131424 A | 5/1990 |
| JP | 2-275882 A | 11/1990 |
| JP | 3-508033 T | 12/1991 |
| JP | 5-58913 A | 3/1993 |
| JP | 5-255337 A | 10/1993 |
| JP | 5-271338 A | 10/1993 |
| JP | 6-220345 A | 8/1994 |
| JP | 10-72449 A | 3/1996 |
| JP | 10-218881 A | 8/1998 |
| JP | 11-43434 A | 2/1999 |
| JP | 2000-502723 T | 3/2000 |
| JP | 2000-503661 A | 3/2000 |
| JP | 2000-109431 A | 4/2000 |
| JP | 2001-89368 A | 4/2001 |
| JP | 2001-511813 A | 8/2001 |
| JP | 2002-76880 A | 3/2002 |
| JP | 2004-53678 A | 2/2004 |
| JP | 2004-532792 A | 10/2004 |
| JP | 2005-314355 A | 11/2005 |
| JP | 2005-314585 A | 11/2005 |
| JP | 2007-515474 A | 6/2007 |
| JP | 2008-503444 A | 2/2008 |
| JP | 2008-517067 A | 5/2008 |
| JP | 2009-510004 A | 3/2009 |
| JP | 2010-235929 A | 10/2010 |
| JP | 2011-40348 A | 2/2011 |
| JP | 4654325 B2 | 3/2011 |
| KR | 10-2005-0070069 A | 7/2005 |
| NO | 20034788 | 12/2003 |
| RU | 2 007 403 C1 | 2/1994 |
| RU | 2002110112 A | 12/2003 |
| SU | 1795971 A3 | 2/1993 |
| WO | 0353902 A1 | 2/1990 |
| WO | WO 90/01030 A1 | 2/1990 |
| WO | WO 94/13643 A1 | 6/1994 |
| WO | WO 94/13644 A1 | 6/1994 |
| WO | WO 94/13661 A1 | 6/1994 |
| WO | WO 94/13676 A1 | 6/1994 |
| WO | WO 94/13677 A1 | 6/1994 |
| WO | WO 95/10506 A1 | 4/1995 |
| WO | WO 95/34563 A1 | 12/1995 |
| WO | WO 97/29109 A1 | 8/1997 |
| WO | WO 97/29110 A1 | 8/1997 |
| WO | 97/44038 A1 | 11/1997 |
| WO | WO 98/08847 A1 | 3/1998 |
| WO | WO 98/35967 A2 | 6/1998 |
| WO | 98/33799 A1 | 8/1998 |
| WO | 98/45295 A1 | 10/1998 |
| WO | WO 99/01454 A1 | 1/1999 |
| WO | WO 99/10350 A1 | 3/1999 |
| WO | WO 99/36393 A1 | 7/1999 |
| WO | WO 99/40090 A1 | 8/1999 |
| WO | WO 00/01697 A1 | 1/2000 |
| WO | WO 00/39127 A1 | 7/2000 |
| WO | WO 00/59907 A2 | 10/2000 |
| WO | WO 00/59908 A2 | 10/2000 |
| WO | WO 01/35917 A1 | 5/2001 |
| WO | WO 01/44248 A1 | 6/2001 |
| WO | WO 02/06288 A2 | 1/2002 |
| WO | WO 02/18320 A2 | 3/2002 |
| WO | WO 02/058704 A1 | 8/2002 |
| WO | 02/085838 A1 | 10/2002 |
| WO | WO-02/088121 A1 | 11/2002 |
| WO | WO 03/072536 A1 | 9/2003 |
| WO | WO 03/078435 A1 | 9/2003 |
| WO | WO-2004/037822 A1 | 5/2004 |
| WO | WO 2009/128383 A1 | 10/2009 |
| WO | WO 2010/015628 A1 | 2/2010 |

OTHER PUBLICATIONS

Arborelius et al., "The Role of Corticotropin Releasing Factor in Depression and Anxiety Disorders", Journal of Endocrinology, vol. 160, 1999, pp. 1-12.

Bakke et al., "Plasma Corticosterone and Restraint Induced Gastric Pathology: Age-Related Differences After Administration of Corticotropin Releasing Factor", Life Sciences, vol. 45, 1989, pp. 907-916, Pergamon Press.

Baldwin et al., "CRF Antagonist Reverses the 'anxiogenic' Response to Ethanol Withdrawal in the Rat" Psychopharmacology, vol. 103, 1991, pp. 227-232.

Banki et al., "CSF Corticotropin-Releasing Factor-Like Immunoreactivity in Depression and Schizophrenia", American Journal of Psychiatry, vol. 144, No. 7, Jul. 1987, pp. 873-877.

Barquist et al., "Abdominal Surgery-Induced Delayed Gastric Emptying in Rats: Role of CRF and Sensory Neurons", CRF and Capsaicin Inhibit Delayed Emptying by Surgery. 1991, pp. G616-G620 (Copyright 1992, The American Physiological Society).

Behan et al., "Displacement of Corticotropin Releasing Factor from Its Binding Protein as a Possible Treatment for Alzheimer's Disease", Nature, vol. 378, Nov. 16, 1995, pp. 284-287.

Bohmer et al., "Effects of Corticotropin-Releasing Factor on Central Respiratory Activity", European Journal of Pharmacology, vol. 182, 1990, pp. 405-411.

Bremner et al., "Elevated CSF Corticotropin-Releasing Factor Concentrations in Posttraumatic Stress Disorder", American Journal of Psychiatry, vol. 154. No. 5, May 1997, pp. 624-629.

Butler et al., "Corticotropin-Releasing Factor Produces Fear-Enhancing And Behavioral Activating Effects Following Infusion Into The Locus Coerules", The Journal of Neuroscience, vol. 10, No. 1, Jan. 1990, pp. 176-183.

Chalmers et al., "Corticotrophin-Releasing Factor Receptors: From Molecular Biology to Drug Design", TIPS, vol. 17, Apr. 1996, pp. 166-172, Elsevier Science Ltd.

Chalmers et al., "Localization of Novel Corticotrophin-Releasing Factor Receptor (CRF2) mRNA Expression to Specific Subcortical Nuclei in Rat Brain: Comparison with CRF1 Receptor mRNA Expression", The Journal of Neuroscience, vol. 15, No. 10, Oct. 1995, pp. 6340-6350.

Chappell et al., "Elevated Cerebrospinal Fluid Corticotropin-Releasing Factor in Tourette's Syndrome: Comparison to Obsessive Compulsive Disorder and Normal Controls", Biol. Psychiatry, vol. 39, 1996, pp. 776-783.

Chen et al., "Design and Synthesis of a Series of Non-Peptide High Affinity Human Corticotropin-Releasing Factor1 Receptor Antagonists", J. Med. Chem., vol. 39, No. 22, 1996, pp. 4358-4360.

Crofford et al., "Corticotropine-Releasing Hormone in Synovial Fluids and Tissues of Patients with Rheumatoid Arthritis and Osteoarthritis", The Journal of Immunology, vol. 151, No. 3, Aug. 1, 1993, pp. 1587-1596.

Crofford et al., "Local Secretion of Corticotrophin-Releasing Hormone in the Joints of Lewis Rats with Inflammatory Arthritis", The Journal of Clinical Investigation, Inc., vol. 90, Dec. 1992, pp. 2555-2564.

Desouza et al., "Corticotrophin-Releasing Hormone (CRH) is Decreased in the Basai Ganglia in Huntington's Disease", Brain Research, vol. 437, 1987, pp. 355-359.

Diamant et al., "Structure-Related Effects of CRF and CRF-Derived Peptides: Dissociation of Behavioral, Endocrine and Autonomic Activity", Neuroendocrinology, vol. 57, 1993, pp. 1071-1081.

Dieterich et al., "Corticotrophin-Releasing Factor Receptors: An Overview", Experimental and Clinical Endocrinology & Diabetes, vol. 105, 1997, pp. 65-82.

Dorwald, "Side Reactions in Organic Synthesis: A Guide to Successful Synthesis Design", 2005.

Dunn et al., "Physiological and Behavioral Responses to Corticotrophin-Releasing Factor Administration: Is CRF a Mediator of Anxiety or Stress Response?", Brain Research Reviews, vol. 15, 1990, pp. 71-100, Elsevier Science Publishers B.V. (pp. 71-79 only provided).

Ehlers et al., "Corticotropin Releasing Factor Produces Increases in Brain Excitability and Convulsive Seizures in Rats", Brain Research, vol. 278, 1983, pp. 332-336. Elsevier.

Ford et al., "Psychosensory Modulation of Colonic Sensation in the Human Transverse and Sigmold Colon," Gastroenterology, vol. 109, No. 6, 1995, pp. 1772-1780.

Fujito et al., "Reaction of Pyridinium and Isoquinolinium N-Imines with Ketenethioacetals", Heterocycles, vol. 6, No. 4, 1977, pp. 379-383.

Fukudo et al., "Impact of Corticotropin-Releasing Hormone on Gastrointestinal Motility and Adrenocorticotropic Hormone in Normal Controls and Patients with Irritable Bowel Syndrome", Gut. vol. 42, 1998, pp. 845-849.

Garrick et al., "Corticotropin-Releasing Factor Acts Centrally to Suppress Stimulated Gastric Contractility in the Rat", Regulatory Peptides, vol. 21, 1988, pp. 173-181, Elsevier.

Gold et al., "Responses to Corticotropin-Releasing Hormone in the Hypercortisolism of Depression and Cushing's Disease", The New England Journal of Medicine, vol. 314, No. 21, May 22, 1986, pp. 1329-1335.

Gubin et al., "Novel Heterocyclic Analogues of the New Potent Class of Calcium Entry Blockers: 1[[4-(Aminoalkoxy)phenyl]sulfonyl]indolizines", Journal of Medicinal Chemistry, vol. 36, No. 10, 1993, pp. 1425-1433.

Gunion et al., "Intrahypothalamic Corticotropin-Releasing Factor Elevates Gastric Bicarbonate and Inhibits Stress Ulcers in Rats", Central CRF and Gastric Bicarbonate, 1989, pp. G152-G157.

Hiroi et al., "Expression of Corticotropin Releasing Hormone Receptors Type I and Type II mRNA in Suicide Victims and Controls", Molecular Psychiatry, vol. 6, 2001, pp. 540-546.

Hotta et al., "The Responses of Plasma Adrenocorticotropin and Cortisol to Corticotropin-Releasing Hormone (CRH) and Cerebrospinal Fluid Immunocreative CRH in Anorexis Nervosa Patients", Journal of Clinical Endocrinology and Metabolism, vol. 62, No. 2, 1986, pp. 319-324.

Jain et al., "Corticotropin-Releasing Factor Modulates the Immune Response to Stress in the Rat", Endocronology, vol. 128, No. 3, 1991, pp. 1329-1336.

Jordan, "Tamoxifen: A Most Unlikely Pioneering Medicine". Nature Reviews, vol. 2, Mar. 2003, pp. 205-213.

Kalin et al., "Fear-Motivated Behavior Induced by Prior Shock Experience is Mediated by Corticotropin-Releasing Hormone Systems", Brain Research, vol. 509, 1990, pp. 80-84, Elsevier.

Karalis et al., "Autocrine or Paracrine Inflammatory Actions of Corticotropin-Releasing Hormone in Vivo", Science, vol. 254, Oct. 18, 1991, pp. 421-423.

Krahn et al., "CRF Antagonist Partially Reverses CRF—and Stress-Induced Effects on Feeding", Brain Research Bulletin, vol. 17, Mar. 24, 1986, pp. 285-289, Ankho International Inc.

Lembo et al., "Effects of the Corticotropin-Releasing Factor (CRF) on Rectal Afferent Nerves in Humans", Neurogastroenterology and Motility, vol. 8, No. 1, Mar. 1996, pp. 9-18.

Lenz et al., "Stress-Induced Gastrointestinal Secretory and Motor Responses in Rats are Mediated by Endogenous Corticotropin-Releasing Factor", Gastroenterology, vol. 95, No. 6, Dec. 1986, pp. 1510-1517.

Leonard, "Changes in the Immune System in Depression and Dementia: Causal or Co-Incidental Effects?", International Journal of Developmental Neuroscience, vol. 19, 2001, pp. 305-312, Elsevier Science Ltd.

Levine et al., "Effect of Centrally Administered Corticotropin Releasing Factor (CRF) on Multiple Feeding Paradigms", Neuropharmacology, vol. 22. No. 3A, 1983, pp. 337-339. Pergamon Press, Ltd., Great Britain.

Liaw et al., "Cloning and Characterization of the Human Corticotropin-Releasing Factor-2 Receptor Complementary Deoxyribonucleic Acid", Endocrinology, vol. 137. No. 1, 1996, pp. 72-77.

Lyons et al., "Corticotropin Releasing Factor Antagonist Reduced Ischemic Hippocampal Neuronal Injury", Brain Research, vol. 545, 1991, pp. 338-342.

Menzaghi et al., "Characterization of a Novel and Potent Corticotropin-Releasing Factor Antagonist in Rats", The Journal of Pharmacology and Experimental Therapeutics, vol. 269, No. 2, Jan. 31, 1994, pp. 564-572.

Monnikes et al., "CRF in the Paraventricular Nucleus of the Hypothalamus Induces Dose-Related Behavioral Profile in Rats", Brain Research, vol. 574, 1992, pp. 70-76, Elsevier Science Publishers B.V.

Morimoto et al., "The Central Role of Corticotropin-Releasing Factor (CRF-41) in Psychological Stress in Rats", Journal of Psychology, vol. 460, 1993, pp. 221-229, Great Britain.

Murakami et al., "Stimulation by Urocortin of Growth Hormone (GH) Secretion in GH-Producing Human Pituitary Adenoma Cells", Endocrine Journal, vol. 44, No. 4, 1997, pp. 627-629.

Nemeroff et al., "Reduced Corticotropin Releasing Factor Binding Sites in the Frontal Cortex of Suicide Victims", Arch. Gen. Psychiatry, vol. 45, 1986, pp. 577-579.

Nicholson et al., "Pituitary and Hypothalamic Hormones in Normal and Neoplastic Adrenal Medullae: Biologically Active Corticotropin-Releasing Hormone and Corticotropin", Regulatory Peptides. vol. 18, 1987, pp. 173-186, Elsevier.

Nink et al., "Effects of Corticotropin-Releasing Hormone on the Postoperative Course of Elderly Patients Under Long-term Artifical Respiration", Acta Endocrinologica, vol. 127, 1992, pp. 200-204.

Notice of Allowance for U.S. Appl. No. 10/250,693, dated Mar. 6, 2006.

Notice of Allowance for U.S. Appl. No. 10/451,741, dated Jan. 12, 2006.

Notice of Allowance for U.S. Appl. No. 10/524,662, dated Jun. 11, 2007.

Notice of Allowance for U.S. Appl. No. 10/524,662, dated Oct. 22, 2007.

Notice of Allowance for U.S. Appl. No. 10/689,088, Sep. 29, 2006.

Notice of Allowance for U.S. Appl. No. 11/757,595, dated Aug. 25, 2009.

Ochi et al., "Studies of Heterocyclic Compounds, VIII, Synthesis and Tautomerism of 2-Hydroxypyrazolo[1,5-alpha]pyridine", Bulletin of the Chemical Society of Japan, vol. 49, No. 7, 1976, pp. 1980-1984.

Owens et al.: "Physiology and Pharmacology of Corticotropin-Releasing Factor", Pharmacological Reviews, vol. 43, No. 4, 1991, pp. 425-473.

Owens et al., "The Effects of Alprazolam on Corticotropin-Releasing Factor Neurons in the Rat Brain: Acute Time Course, Chronic Treatment and Abrupt Withdrawal", The Journal of Pharmacology and Experimental Therapeutics, vol. 258. No. 1, 1991, pp. 349-356.

Petrusz et al., "Corticotropin-Releasing Factor (CRF)-Like Immunoreactivity in the Gastro-Entero-Pancreatic Endocrine System", Peptides, vol. 5, Suppl. 1, 1984, pp. 71-78, Ankho International Inc.

Plotsky et al., "Hypothalamic-Pituitary-Adrenal Axis Function in the Zucker Obese Rat", Endocrinology, vol. 130, No. 4, 1992, pp. 1931-1941.

Poliak et al., "Stress and Autoimmunity: The Neuropeptides Corticotropin-Releasing Factor and Urocortin Suppress-Encephalomyelitis via Effects on Both the Hypothalamic-Pituitary-Adrenal Axis and the Immune System", The Journal of Immunology, vol. 158, 1997, pp. 5751-5756.

Raadsheer et al., "Corticotropin-Releasing Hormone mRNA Levels in the Paraventricular Nucleus of Patients With Alzheimer's Disease and Depression", American Journal of Psychiatry, vol. 152, No. 9, Sep. 1995, pp. 1372-1376.

Rivier et al., "Characterization of Rat Hypothalamic Corticotropin-Releasing Factor", Proc. Natl. Acad. Sci. USA, vol. 80, Aug. 1983, pp. 4851-4855.

Rivier et al., "Synthetic Competitive Antagonists of Corticotropin-Releasing Factor: Effect on ACTH Secretion in the Rat", Science, vol. 224, May 25, 1984, pp. 889-891.

Roy-Byrne et al., "The Corticotropin-Releasing Hormone Stimulation Test in Patients With Panic Disorder", Am. J. Psychiatry, vol. 143, No. 7, Jul. 1986, pp. 896-899.

Sasaki et al., "Immunoreactive Corticotropin-Releasing Hormone Present in Human Plasma May Be Derived From Both Hypothalamic and Extrahypothalamic Sources", Journal of Clinical Endocrinology and Metabolism, vol. 65, No. 1, 1987, pp. 176-182.

Sasaki et al, "Isolation and Characterization of a Corticotropin-Releasing Hormone-Like Peptide From Human Placenta", Journal of Clinical Endocrinology and Metabolism, vol. 67, No. 4, 1988, pp. 768-773.

Sauvage et al., "Detection of Corticotropin—Releasing Hormone Receptor 1 Immunoreactivity in Cholinergic, Dopaminergic and Noradrenergic Neurons of the Murine Basal Forebrain and Brainstem Nuclei-Potential Implication for Arousal and Attention", Neuroscience, vol. 104, No. 3, 2001, pp. 643-652.

Scopa et al., "Presence of Immunoreactive Corticotropin Releasing Hormone in Thyroid Lesions", American Journal of Pathology. vol. 145, No. 5, Nov. 1994, pp. 1159-1167.

Sherman et al., "The Effects of ICV-CRH on Novelty-Induced Behavior", Pharmacology Biochemistry & Behavior, vol. 26, 1987, pp. 699-703, Pergamon Journals Ltd.

Shibahara, et al., "Isolation and Sequence Analysis of the Human Corticotropin-Releasing Factor Precursor Gene", The EMBO Journal, vol. 2, No. 5, 1993, pp. 775-779.

Singh et al., "Enhancing Effect of Corticotropin-Releasing Neurohormone on the Production of Interleukin-1 and Interleukin-2", Neuroscience Letters, vol. 120, 1990, pp. 151-154, Elsevier Scientific Publishers Ireland Ltd.

Singh et al., "Potent Mast Cell Degranulation and Vascular Permeability Triggered by Urocortin Through Activation of Corticotropin-Releasing Hormone Receptors", The Journal of Pharmacology and Experimental Therapeutics, vol. 288, No. 3, 1999, pp. 1349-1356.

Singh, "Stimulatory Effect of Corticotropin-Releasing Neurohormone on Human Lymphocyte Proliferation and Interleukin-2 Receptor Expression", Journal of Neuroimmunology, vol. 23, 1989, pp. 257-262, Elsevier Science Publishers B.V.

Sirinathsinghji et al., "Corticotropin-Releasing Factor is a Potent Inhibit of Sexual Receptivity in the Female Rat", Nature, vol. 305, Sep. 15, 1983, pp. 232-235.

Stenzel-Poore et al., "Development of Cushing's Syndrome in Corticotropin-Releasing Factor Transgenic Mice", Endocrinology, vol. 130, No. 6, 1992, pp. 3378-3386.

Stenzel-Poore et al., "Overproduction of Corticotropin-Releasing Factor in Transgenic Mice: A Genetic Model of Anxiogenic Behavior", The Journal of Neuroscience, vol. 14, No. 5, May 1994, pp. 2579-2584.

Tache et al., "Role of CFR in Stress-Related Alterations of Gastric and Colonic Motor Function", Annals of the New York Academy of Sciences. vol. 697, Corticotropin-Releasing Factor and Cytokinses: Role in The Stress Response, 1993, cover page, dedication page, pp. 232-243.

Tache et al., "Central Nervous System Action of Corticotropin-Releasing Factor to Inhibit Gastric Emptying in Rats", American Journal of Psychiatry, vol. 253. 1987, pp. G241-G245.

Tazi et al., "Corticotropin-Releasing Factor Antagonist Blocks Stress-Induced Fighting in Rats", Regulatory Peptides, vol. 18, 1987, pp. 37-42, Elsevier Science Publishers B.V.

Theoharides et al., "Corticotropin-Releasing Hormone Induces Skin Mast Cell Degranulation and Increased Vascular Permeability, a Possible Explanation for Its Proinflammatory Effects", Endocrinology, vol. 139, No. 1, 1996, pp. 403-413.

Tominaga et al. "Reaction of Pyridinium and Quinolinium N-Imines with Ketenethioacetais", Yakugaku Zasshi, vol. 104, No. 5, 1984, pp. 440-448.

US Office Action for U.S. Appl. No. 10/451,741, dated Jan. 28, 2005.
US Office Action for U.S. Appl. No. 10/451,741, dated Sep. 22, 2005.
US Office Action for U.S. Appl. No. 10/524,662, dated Feb. 5, 2007.
US Office Action for U.S. Appl. No. 10/689,088, dated Apr. 28, 2005.
US Office Action for U.S. Appl. No. 10/689,088, dated Mar. 30, 2006.
US Office Action for U.S. Appl. No. 10/689,088, dated Oct. 18, 2005.
US Office Action for U.S. Appl. No. 11/421,740, dated May 19, 2008.
US Office Action for U.S. Appl. No. 11/421,740, dated Sep. 3, 2008.
US Office Action for U.S. Appl. No. 11/446,415, dated Aug. 1, 2007.
US Office Action for U.S. Appl. No. 11/446,416, dated Feb. 21, 2007.
US Office Action for U.S. Appl. No. 11/757,595, dated Dec. 8, 2008.
US Office Action for U.S. Appl. No. 11/858,160, dated Jan. 22, 2009.
US Office Action for U.S. Appl. No. 12/397,132, dated Jun. 15, 2009.
US Office Action for U.S. Appl. No. 12/397,132, dated Sep. 16, 2009.
US Office Action for U.S. Appl. No. 10/250,693, dated Sep. 2, 2005.

Valdenaire et al., "A New Functional Isoform of the Human CRF2 Receptor for Corticotropin-Releasing Factor", Biochimica et Biophysica Acta, vol. 1352. 1997, pp. 129-132, Elsevier Science B.V.

Vale et al., "Characterization of a 41-Residue Ovine Hypothalamic Peptide That Stimulates Secretion of Corticotropin and Beta-Endorphin", Science, vol. 213, Sep. 18, 1981, pp. 1394-1397.

Vale et al., "Chemical and Biological Characterization of Corticotropin Releasing Factor", Recent Progress in Hormone Research, vol. 39, 1983, cover page, pp. 245-270.

Whitehouse et al., "Reductions in Corticotropin Releasing Factor-Like Immunoreactivity in Cerebral Cortex in Alzheimer's Disease, Parkinson's Disease, and Progressive Supranuclear Palsy", Neurology, vol. 37, pp. 905-909, Jun. 1987.

Whitten et al., "Rapid Microscale Synthesis, a New Method for Lead Optimization Using Robotics and Solution Phase Chemistry: Application to the Synthesis and Optimization of Corticotropin-Releasing Factor1 Receptor Antagonists", J. Med. Chem., vol. 39, No. 22, 1996, pp. 4354-4357.

International Preliminary Report on Patentability, dated Nov. 30, 2010, for Application No. PCT/JP2009/057270.

International Search Report, dated Nov. 16, 2010, for Application No. PCT/JP2010/067556.

Maecker et al., "Astressin, a Novel and Potent CFR Antagonist, is Neuroprotective in the Hippocampus When Administered After a Seizure, " Brain Research, 1997, pp. 166-170, vol. 744, Elsevier Science B.V.

Strijbos et al., "Corticotropin-Releasing Factor Antagonist Inhibits Neuronal Damage Induced by Focal Cerebral Ischaemia or Activation of NMDA Receptors in the Rat Brain," Brain Research, 1994, pp. 405-408, vol. 656, Elsevier Science B.V.

Blank et al., "The Corticotropin-Releasing Factor Receptor 1 Antagonist CP-154,526 Reverses Stress-induced Learning Deficits in Mice". Behavioral Brain Research, 2003, pp. 207-213, vol. 136, Elsevier Science B.V.

Luckey et al., "Corticotropin-Releasing Factor Receptor 1-Deficient Mice Do Not Develop Postoperative Gastric Ileus", Gastroenterology, Dec. 2003, pp. 654-659, vol. 125, No. 3.

Hotta et al, "Corticotropin-Releasing Factor Receptor Type 1 Mediates Emotional Stress-Induced Inhibition of Food Intake and Behavioral Changes in Rats", Brain Research, 1999, pp. 221-225, vol. 823, Elsevier Science B.V.

Martinez et al., "Role of CRF Receptor 1 in Central CRF-Induced Stimulation of Colonic Propulsion in Rats," Brain Research, 2001, pp. 29-35, vol. 893, Elsevier Science B.V.

Rassnick et al., "Microinjection of a Corticotropin-Releasing Factor Antagonist into the Central Nucleus of the Amygdala Reverses Anxiogenic-Like Effects of Ethanol Withdrawal", Brain Research, 1993, vol. 605, Elsevier Science B.V.

Iredale et al., "Role of Corticotropin-Releasing Factor Receptor-1 in Opiate Withdrawal," Journal of Neurochemistry, 2000, pp. 199-208, vol. 74, No. 1, Lippincott Williams & Wilkins, Inc., Philadelphia, PA.

Lancel et al., "The CRH1 Receptor Antagonist R121919 Attenuates Stress-Elicited Sleep Disturbances in Rats, Particularly in Those with High Innate Anxiety", Journal of Psychiatric Research, 2002, pp. 197-208, vol. 36, Elsevier Science Ltd.

Lé et al., "The Role of Corticotropin-Releasing Factor in Stress-Induced Relapse to Alcohol-Seeking Behavior in Rats", Psychopharmacology, 2000, pp. 317-324, vol. 150.

Nakazato et al., "Corticotropin-Releasing Factor$_1$ Receptor as a Target for Therapeutic Intervention", Drugs of the Future, 1999, pp. 1089-1098, vol. 24, No. 10, Prous Science.

Sagami et al., "Effect of a Corticotropin Releasing Hormone Receptor Antagonist on Colonic Sensory and Motor Function in Patients with Irritable Bowel Syndrome", Gut, 2004, pp. 958-964.

Keck et al., "The Anxiolytic Effect of the CRH$_1$ Receptor Antagonist R121919 Depends on Innate Emotionality in Rats", European Journal of Neuroscience, 2001, pp. 373-380, vol. 13, Federation of European Neuroscience Societies.

Overstreet et al, "Antidepressant Effects of Citalopram and CRF Receptor Antagonist CP-154,526 in a Rat Model of Depression", European Journal of Pharmacology, 2004. pp. 195-201, vol. 492, Elsevier B.V.

Kang et al., "Acute Stress Increases Interstitial Fluid Amyloid-β via Corticotropin-Releasing Factor and Neuronal Activity", PNAS, Jun. 19, 2007, pp. 10673-10678, vol. 104, No. 25.

Zobel et al., "Effects of the High-Affinity Corticotropin-Releasing Hormone Receptor 1 Antagonist R121919 in Major Depression: the First 20 Patients Treated", Journal of Psychiatric Research, 2000, pp. 171-181, vol. 34, Elsevier Science Ltd.

Briscoe et al., "Antalarmin Blockade of Corticotropin Releasing Hormone-Induced Hypertension in Rats", Brain Research, 2000, pp. 204-207, vol. 881, Elsevier Science B.V.

Baram et al., "The CRF1 Receptor Mediates the Excitatory Actions of Corticotropin Releasing Factor (CFR) in the developing Rat Brain: in Vivo Evidence using a Novel, Selective, Non-Peptide CRF Receptor Antagonist", Brain Research, 1997, pp. 89-95, vol. 770.

Shaham et al., "CP-154,526. a Selective. Non-Peptide Antagonist of the Corticotropin-Releasing Factor1 Receptor Attenuates Stress-Induced Relapse to Drug Seeking in Cocaine- and Heroin-Trained Rats", Psychopharmacology, 1998, pp. 184-190, vol. 137.

Rissman et al., "Corticotropin-Releasing Factor Receptors Differentially regulate Stress-Induced Tau Phosphorylation", Journal of Neuroscience, Jun. 13, 2007, pp. 6552-6562. vol. 27, No. 24.

Lee et al., "Behavioral Stress Accelerates Plaque Pathogenesis in the Brain of Tg2576 Mice Via Generation of Metabolic Oxidative Stress", Journal of Neurochemistry, 2009, pp. 1165-1175, vol. 108, International Society for Neurochemistry.

International Search Report, dated Dec. 21, 2010, for Application No. PCT/JP2010/067564.

Chilean Office Action, dated Jun. 14, 2011, for Chilean Application No. 896-09.

English translation of Chilean Office Action, dated Jun. 14, 2011, for Chilean Application No. 896-09.

Vietnamese Notice of Allowance for Vietnamese Application No. 1-2005-00679, dated Jan. 18, 2012.

Canadian Notice of Allowance, dated Jan. 13, 2011, for Canadian Application No. 2,494,574.

Canadian Notice of Allowance, dated Nov. 18, 2009, for Canadian Application No. 2,443,802.

Canadian Office Action, dated Apr. 14, 2009, for Canadian Application No. 2,443,802.

Canadian Office Action, dated Apr. 28, 2010, for Canadian Application No. 2,494,574.

Canadian Request for Examination, dated Jun. 10, 2008, for Canadian Application No. 2,494,574.

Chilean Amendment, dated Jul. 23, 2010, for Chilean Application No. 896-2009.

Chilean Office Action, dated Jan. 25, 2012, for Chilean Application No. 896-09.

Chinese Amendment, dated Mar. 22, 2006, for Chinese Application No. 200380101417.7.

Chinese Office Action, dated Apr. 24, 2009, for Chinese Application No. 200710128112.5.

Chinese Office Action, dated Feb. 17, 2006, for Chinese Application No. 02808872.7.

Chinese Office Action, dated Jul. 22, 2005, for Chinese Application No. 02808872.7.

Chinese Office Action, dated Jun. 1, 2007, for Chinese Application No. 200380101417.7.

Chinese Office Action, dated Jun. 5, 2009, for Chinese Application No. 200710128111.0.

Chinese Office Action, dated May 26, 2006, for Chinese Application No. 200380101417.7.

Chinese Office Action, dated Oct. 13, 2006, for Chinese Application No. 200380101417.7.

Chinese Office Action, dated Oct. 16, 2009, for Chinese Application No. 200710128111.0.

Chinese Office Action, dated Sep. 22, 2006, for Chinese Application No. 02808872.7.

Czech Office Action, dated Jul. 30, 2009, for Czech Application No. PV 2003-2937.

Czech Office Action, dated Mar. 26, 2009, for Czech Application No. PV 2003-2937.

Czech Office Action, dated Nov. 20, 2009, for Czech Application No. PV 2003-2937.

Czech Office Action, dated Sep. 24, 2008, for Czech Application No. PV 2003-2937.

Dautzenberg et al., "The CRF peptide family and their receptors: yet more partners discovered", TRENDS in Pharmacological Sciences, vol. 23, No. 2, pp. 71-77, Feb. 2002.

European Office Action, dated Apr. 21, 2008, for European Application No. 03758781.3.

European Office Action, dated Apr. 4, 2008, for European Application No. 02711424.8.

European Office Action, dated Feb. 16, 2009, for European Application No. 03758781.3.

European Office Action, dated Feb. 26, 2009, for European Application No. 03758781.3.

European Office Action, dated Jan. 4, 2010, for European Application No. 02720608.5.

European Office Action, dated Jul. 19, 2010, for European Application No. 02711424.8.

European Office Action, dated Jul. 22, 2011, for European Application No. 09732907.2.

European Office Action, dated Jun. 14, 2005, for European Application No. 02720608.5.

European Office Action, dated Jun. 8, 2009, for European Application No. 02711424.8.

European Office Action, dated May 16, 2011, for European Application No. 02711424.8.

European Office Action, dated May 22, 2007, for European Application No. 02711424.8.

European Office Action, dated Nov. 14, 2007, for European Application No. 03758781.3.

European Office Action, dated Nov. 25, 2010, for European Application No. 02720608.5.

European Office Action, dated Sep. 4, 2008, for European Application No. 03758781.3.
European Submission of English translation of priority document, dated Aug. 13, 2007, for European Application No. 02720608.5.
Extended European Search Report, dated Jul. 5, 2011, for European Application No. 09732907.2.
Filipino Notice of Allowability, dated Jul. 18, 2008, for Filipino Application No. 1-2005-500278.
Filipino Notice of Allowability, dated Mar. 21, 2007, for Filipino Application No. 1-2003-501066.
Filipino Office Action, dated Feb. 9, 2004, for Filipino Application No. 1-2003-501066.
Filipino Office Action, dated Jan. 31, 2008, for Filipino Application No. 1-2005-500278.
Filipino Office Action, dated May 23, 2008, for Filipino Application No. 1-2005-500278.
Filipino Office Action, dated Nov. 22, 2006, for Filipino Application No. 1-2003-501066.
Filipino Office Action, dated Oct. 31, 2007, for Filipino Application No. 1-2007-500806.
Hong Kong Request to record a designated patent application for a standard patent, dated Feb. 2, 2006, for Hong Kong Application No. 06101472.9.
Hungarian Office Action, dated Feb. 18, 2011, for Hungarian Application No. P0401292.
Hungarian Request for Amendment, dated Feb. 14, 2005, for Hungarian Application No. P0401292.
Hungarian Search Report, dated Dec. 16, 2010, for Hungarian Application No. P0401292.
Indian Amendment, dated Oct. 16, 2008, for Indian Application No. 961/CHENP/2005.
Indian Office Action, dated May 10, 2007, for Indian Application No. 1748/DELNP/2003.
Indian Office Action, dated Nov. 25, 2008, for Indian Application No. 961/CHENP/2005.
Indian Office Action, dated Nov. 4, 2009, for Indian Application No. 961/CHENP/2005.
Indian Office Action, dated Sep. 15, 2010, for Indian Application No. 1966/CHENP/2007.
Indian Office Action, dated Sep. 17, 2007, for Indian Application No. 1748/DELNP/2003.
Indian Office Action, dated Sep. 27, 2006, for Indian Application No. 1748/DELNP/2003.
Indian Section 8(1) filing, dated Apr. 29, 2011, for Indian Application No. 7277/CHENP/2010.
Indonesian Notice of Allowance, dated Nov. 2, 2009, for Indonesian Application No. W-00200500983.
Indonesian Office Action, dated Apr. 2, 2008, for Indonesian Application No. W-00200500983.
Japanese Amendment and Explanation for Circumstances Concerning Accelerated Examination, dated Oct. 27, 2010, for Japanese Application No. 2010-508183.
Japanese Amendment and Petition, dated Oct. 7, 2008, for Japanese Application No. 2004-546447.
Japanese Amendment and Request for Examination, dated Jan. 13, 2005, for Japanese Application No. 2002-585420
Japanese Office Action, dated Aug. 5, 2008, for Japanese Application No. 2002-585420.
Japanese Office Action, dated Dec. 14, 2010, for Japanese Application No. 2010-508183.
Japanese Office Action, dated Feb. 16, 2010, for Japanese Application No. 2002-563153.
Japanese Office Action, dated Feb. 27, 2009, for Japanese Application No. 2002-563153.
Japanese Office Action, dated Jun. 2, 2010, for Japanese Application No. 2002-563153.
Japanese Office Action, dated May 26, 2009, for Japanese Application No. 2004-546447.
Japanese Office Action, dated Sep. 30, 2008, for Japanese Application No. 2002-585420.
Jordanian Amendment, dated Aug. 30, 2010, for Jordanian Application No. 127/2009.
Kehne et al., "Non-Peptidic CRF1 Receptor Antagonists for the Treatment of Anxiety, Depression and Stress Disorders", Current Drug Targets—CNS & Neurological Disorders, vol. 1, No. 5, pp. 467-493, 2002.
Korean Amendment, dated Dec. 7, 2010, for Korean Application No. 10-2010-7019769.
Korean Amendment, dated Jun. 19, 2008, for Korean Application No. 10-2008-7006800.
Korean Amendment, dated Oct. 13, 2008, for Korean Application No. 10-2008-7006800.
Korean Office Action, dated Aug. 16, 2010, for Korean Application No. 10-2008-7006800.
Korean Office Action, dated Dec. 4, 2008, for Korean Application No. 10-2003-7013949.
Korean Office Action, dated May 16, 2008, for Korean Application No. 10-2003-7013949.
Korean Office Action, dated May 16, 2008, for Korean Application No. 10-2008-7005209.
Korean Office Action, dated Nov. 4, 2008, for Korean Application No. 10-2008-7005209.
Korean Office Action, dated Oct. 31, 2007, for Korean Application No. 10-2003-7013949.
Korean Request for Examination, dated Jun. 19, 2008, for Korean Application No. 10-2008-7006800.
Kosovo Amendment, dated Mar. 1, 2011, for Kosovo Application No. 329.
Malaysian Statement Justifying the Applicant's Right to a Patent, dated Sep. 27, 2010, for Malaysian Application No. PI2010004527 (Derived from International Application No. PCT/JP2009/057270).
Mexican Notice of Allowance, dated Dec. 3, 2010, for Mexican Application No. PA/a/2007/009752.
Mexican Notice of Allowance, dated Jul. 20, 2007, for Mexican Application No. PA/a/2005/002185.
Mexican Notice of Allowance, dated May 15, 2008, for Mexican Application No. PA/a/2003/009738.
Mexican Office Action, dated Mar. 12, 2008, for Mexican Application No. PA/a/2003/009738.
New Zealand Examination Report and Notice of Acceptance, dated Jun. 8, 2011, for New Zealand Application No. 588376.
New Zealand Examination Report, dated Mar. 29, 2011, for New Zealand Application No. 588376.
New Zealand Examination Report, dated May 26, 2004, for New Zealand Application No. 529333.
New Zealand Examination Report, dated Oct. 25, 2005, for New Zealand Application No. 538860.
New Zealand Notice of Acceptance, dated Dec. 22, 2004, for New Zealand Application No. 529333.
New Zealand Notice of Acceptance, dated Jun. 26, 2006, for New Zealand Application No. 538860.
Norwegian Amendment, dated Oct. 14, 2008, for Norwegian Application No. 20052443.
Norwegian Notice of Allowance, dated Nov. 7, 2008, for Norwegian Application No. 20034788.
Norwegian Notice of Allowance, dated Sep. 6, 2011, for Norwegian Application No. 20052443.
Norwegian Office Action, dated Apr. 13, 2011, for Norwegian Application No. 20052443.
Norwegian Office Action, dated Jan. 14, 2011, for Norwegian Application No. 20052443.
Norwegian Office Action, dated Jun. 3, 2011, for Norwegian Application No. 20052443.
Norwegian Office Action, dated Mar. 25, 2008, for Norwegian Application No. 20034788.
Norwegian Office Action, dated Nov. 12, 2007, for Norwegian Application No. 20034788.
Pakistani Notice of Acceptance, dated Feb. 29, 2012, for Pakistani Application No. 101/2011.
Pakistani Notice of Acceptance, dated Feb. 29, 2012, for Pakistani Application No. 307/2009.
Pakistani Office Action, dated Aug. 3, 2009, for Pakistani Application No. 307/2009.
Peruvian Amendment, dated Aug. 2, 2010, for Peruvian Application No. 000505.2009.

Polish Office Action, dated Apr. 28, 2009, for Polish Application No. P-367067.
Polish Office Action, dated Apr. 29, 2010, for Polish Application No. P-376132.
Polish Office Action, dated Jul. 29, 2011, for Polish Application No. P-367067.
Polish Office Action, dated Mar. 4, 2010, for Polish Application No. P-367067.
Response to Australian Office Action, dated Apr. 23, 2009, for Australian Application No. 2003275589.
Response to Australian Office Action, dated Dec. 18, 2006, for Australian Application No. 2002251546.
Response to Canadian Office Action, dated Jun. 10, 2010, for Canadian Application No. 2,494,574.
Response to Canadian Office Action, dated Jun. 17, 2009, for Canadian Application No. 2,443,802.
Response to Chilean Office Action, dated Sep. 15, 2011, for Chilean Application No. 896-2009.
Response to Chinese Office Action, dated Apr. 17, 2006, for Chinese Application No. 02808872.7.
Response to Chinese Office Action, dated Aug. 1, 2006, for Chinese Application No. 200380101417.7.
Response to Chinese Office Action, dated Dec. 25, 2006, for Chinese Application No. 200380101417.7.
Response to Chinese Office Action, dated Jul. 17, 2009, for Chinese Application No. 200710128111.0.
Response to Chinese Office Action, dated Nov. 23, 2005, for Chinese Application No. 02808872.7.
Response to Czech Office Action, dated Feb. 5, 2009, for Czech Application No. PV 2003-2937.
Response to Czech Office Action, dated May 25, 2009, for Czech Application No. PV 2003-2937.
Response to Czech Office Action, dated Oct. 12, 2009, for Czech Application No. PV 2003-2937.
Response to European Office Action, dated Aug. 4, 2005, for European Application No. 02720608.5.
Response to European Office Action, dated Feb. 15, 2010, for European Application No. 02720608.5
Response to European Office Action, dated Feb. 27, 2008, for European Application No. 0375 8781.3.
Response to European Office Action, dated May 19, 2008, for European Application No. 03758781.3.
Response to European Office Action, dated Oct. 1, 2007, for European Application No. 02711424.8.
Response to European Office Action, dated Oct. 14, 2008, for European Application No. 02711424.8.
Response to European Office Action, dated Oct. 27, 2010, for European Application No. 02711424.8.
Response to European Office Action, dated Oct. 5, 2009, for European Application No. 02711424.8.
Response to Filipino Office Action, dated Jun. 18, 2008, for Filipino Application No. 1-2005-500278.
Response to Filipino Office Action, dated Mar. 11, 2004, for Filipino Application No. 1-2003-501066.
Response to Filipino Office Action, dated Mar. 2, 2007, for Filipino Application No. 1-2003-501066.
Response to Filipino Office Action, dated Mar. 3, 2008, for Filipino Application No. 1-2005-500278.
Response to Filipino Office Action, dated Nov. 27, 2007, for Filipino Application No. 1-2007-500806.
Response to Hungarian Office Action, dated Jun. 17, 2011, for Hungarian Application No. P0401292.
Response to Indian Office Action, dated Aug. 10, 2007, for Indian Application No. 1748/DELNP/2003.
Response to Indian Office Action, dated Jan. 10, 2011, for Indian Application No. 1966/CHENP/2007.
Response to Indian Office Action, dated Mar. 24, 2009, for Indian Application No. 961/CHENP/2005.
Response to Indian Office Action, dated May 1, 2007, for Indian Application No. 1748/DELNP/2003.
Response to Indian Office Action, dated Nov. 13, 2009, for Indian Application No. 961/CHENP/2005
Response to Indian Office Action, dated Sep. 24, 2007, for Indian Application No. 1748/DELNP/2003.
Response to Indonesian Office Action, dated Jul. 3, 2008, for Indonesian Application No. W-00200500983.
Response to Indonesian Office Action, dated Oct. 16, 2008, for Indonesian Application No. W-00200500983.
Response to Japanese Office Action, dated Apr. 20, 2010, for Japanese Application No. 2002-563153.
Response to Japanese Office Action, dated Apr. 28, 2009, for Japanese Application No. 2002-563153.
Response to Korean Office Action, dated Feb. 29, 2008, for Korean Application No. 10-2003-7013949.
Response to Korean Office Action, dated Jul. 16, 2008, for Korean Application No. 10-2003-7013949.
Response to Korean Office Action, dated Jul. 16, 2008, for Korean Application No. 10-2008-7005209.
Response to Mexican Office Action, dated May 8, 2008, for Mexican Application No. PA/a/2003/009738.
Response to New Zealand Examination Report, dated Apr. 13, 2006, for New Zealand Application No. 538860.
Response to New Zealand Examination Report, dated May 25, 2011, for New Zealand Application No. 588376.
Response to New Zealand Examination Report, dated Nov. 22, 2004, for New Zealand Application No. 529333.
Response to Norwegian Office Action, dated Aug. 16, 2011, for Norwegian Application No. 20052443.
Response to Norwegian Office Action, dated Mar. 12, 2008, for Norwegian Application No. 20034788.
Response to Norwegian Office Action, dated Mar. 30, 2011, for Norwegian Application No. 20052443.
Response to Norwegian Office Action, dated May 24, 2011, for Norwegian Application No. 20052443.
Response to Norwegian Office Action, dated Oct. 27, 2008, for Norwegian Application No. 20034788.
Response to Pakistani Office Action, dated Feb. 17, 2011, for Pakistani Application No. 307/2009.
Response to Pakistani Office Action, dated Jul. 27, 2011, for Pakistani Application No. 307/2009.
Response to Polish Office Action, dated Jul. 5, 2010, for Polish Application No. P-367067.
Response to Polish Office Action, dated Jun. 22, 2010, for Polish Application No. P-376132.
Response to Polish Office Action, dated Jun. 29, 2009, for Polish Application No. P-367067.
Response to Polish Office Action, dated Oct. 25, 2011, for Polish Application No. P-367067.
Response to Russian Office Action, dated Apr. 2, 2004, for Russian Application No. 2003134371.
Response to Russian Office Action, dated Dec. 1, 2006, for Russian Application No. 2003134371.
Response to Russian Office Action, dated Jul. 3, 2006, for Russian Application No. 2003134371.
Response to Russian Office Action, dated Nov. 13, 2007, for Russian Application No. 2005115504.
Response to Taiwanese Office Action, dated Jun. 3, 2005, for Taiwanese Application No. 091108720.
Response to Taiwanese Office Action, dated Sep. 12, 2006, for Taiwanese Application No. 092129327.
Response to Taiwanese Office Action, dated Sep. 8, 2005, for Taiwanese Application No. 091108720.
Response to Thai Office Action, dated Jul. 23, 2010, for Thai Application No. 0901001738.
Response to US Office Action, dated Apr. 19, 2007, for U.S. Appl. No. 10/524,662.
Response to US Office Action, dated Apr. 2, 2009, for U.S. Appl. No. 11/757,595.
Response to US Office Action, dated Apr. 27, 2007, for U.S Appl. No. 11/446,416.
Response to US Office Action, dated Aug. 2, 2005, for U.S. Appl. No. 10/451,741.
Response to US Office Action, dated Dec. 11, 2009, for U.S. Appl. No. 12/397,132.

Response to US Office Action, dated Dec. 14, 2005, for U.S. Appl. No. 10/689,088.
Response to US Office Action, dated Dec. 2, 2005, for U.S. Appl. No. 10/250,693.
Response to US Office Action, dated Dec. 22, 2005, for U.S. Appl. No. 10/451,741.
Response to US Office Action, dated Feb. 28, 2005, for U.S. Appl. No. 10/451,741.
Response to US Office Action, dated Jul. 10, 2009, for U.S. Appl. No. 12/397,132.
Response to US Office Action, dated Jul. 25, 2005, for U.S. Appl. No. 10/689,088.
Response to US Office Action, dated Jun. 12, 2006, for U.S. Appl. No. 10/689,088.
Response to US Office Action, dated Jun. 19, 2008, for U.S. Appl. No. 11/421,740.
Response to US Office Action, dated Mar. 10, 2010, for U.S. Appl. No. 12/397,132.
Response to Vietnamese Office Action, dated May 26, 2008, for Vietnamese Application No. 1-2005-00679.
Russian Office Action, dated Feb. 1, 2006, for Russian Application No. 2003134371.
Russian Office Action, dated Feb. 13, 2007, for Russian Application No. 2003134371.
Russian Office Action, dated Feb. 2, 2004, for Russian Application No. 2003134371.
Russian Office Action, dated Mar. 12, 2007, for Russian Application No. 2005115504.
Russian Office Action, dated Nov. 22, 2007, for Russian Application No. 2005115504.
Russian Office Action, dated Sep. 29, 2006, for Russian Application No. 2003134371.
Russian Request for Substantial Examination, dated Mar. 22, 2005, for Russian Application No. 2003134371.
Russian Request for Examination, dated Jul. 4, 2006, for Russian Application No. 2005115504.
Singapore Amendment, dated Apr. 20, 2007, for Singapore Application No. 200502609-1.
Singapore Amendment, dated Jul. 28, 2011, for Singapore Application No. 201005623-2.
Singapore Amendment, dated May 28, 2004, for Singapore Application No. 200306355-9.
Singapore Amendment, dated Oct. 18, 2005, for Singapore Application No. 200306355-9.
Singapore Notification of Grant, dated Feb. 28, 2006, for Singapore Application No. 200306355-9.
Singapore Notification of Grant, dated Jul. 31, 2007, for Singapore Application No. 200502609-1.
South African Amendment, dated Feb. 15, 2005, for South African Application No. 2005/01310.
South African Amendment, dated Jan. 19, 2005, for South African Application No. 2003/8860.
South African Office Action, dated Feb. 14, 2005, for South African Application No. 2003/8860.
South African Office Action, dated Jan. 5, 2012, for South African Application No. 2010/06764.
South African Office Action, dated Jul. 3, 2006, for South African Application No. 2005/01310.
Sri Lankan Certificate of Grant, dated Nov. 25, 2010, for Sri Lankan Patent No. 13600.
Supplementary Partial European Search Report, dated Feb. 11, 2005, for European Application No. 02711424.8.
Supplementary Partial European Search Report, dated Jul. 5, 2006, for European Application No. 03758781.3.
Supplementary Partial European Search Report, dated Jun. 3, 2005, for European Application No. 02720608.5.
Taiwanese Amendment, dated Mar. 3, 2007, for Taiwanese Application No. 092129327.
Taiwanese Amendment, dated Nov. 8, 2007, for Taiwanese Application No. 091108720.
Taiwanese Office Action, dated Apr. 7, 2005, for Taiwanese Application No. 091108720.
Taiwanese Office Action, dated Jul. 11, 2005, for Taiwanese Application No. 091108720.
Taiwanese Office Action, dated Jul. 27, 2006, for Taiwanese Application No. 092129327.
Taiwanese Office Action, dated Mar. 22, 2007, for Taiwanese Application No. 092129327.
Taiwanese Office Action, dated Nov. 23, 2007, for Taiwanese Application No. 091108720.
US Notice of Allowance, dated Jun. 20, 2007, for U.S. Appl. No. 11/446,416.
US Notice of Allowance, dated Mar. 29, 2010, for U.S. Appl. No. 12/397,132.
US Notice of Allowance, dated Oct. 22, 2007, for U.S. Appl. No. 10/524,662.
US Office Action, dated Apr. 1, 2005, for U.S. Appl. No. 10/451,741.
US Office Action, dated Feb. 22, 2012, for U.S. Appl. No. 12/900,026.
Venezuelan Amendment, dated Dec. 21, 2010, for Venezuelan Application No. 2009-000652.
Vietnamese Amendment, dated Oct. 21, 2008, for Vietnamese Application No. 1-2005-00679.
Vietnamese Notice of Acceptance, dated Jun. 27, 2005, for Vietnamese Application No. 1-2005-00679.
Vietnamese Office Action, dated Mar. 25, 2008, for Vietnamese Application No. 1-2005-00679.
Amendment dated Nov. 10, 2011 in response to the Communication pursuant to Rule 70(2) and 70a(2) EPC dated Jul. 22, 2011 for European Patent Application No. 09732907.2.
U.S. Office Action (Restriction) for U.S. Appl. No. 12/900,046, dated Feb. 22, 2012.
Mexican Office Action dated May 28, 2012 for Patent Application No. MX/a/2010/011089.
Request for Advanced Examination and Submission of Prior Art in Canadian Patent Application No. 2721670 dated Jun. 11, 2012.
U.S. Office Action dated Jun. 22, 2012, for U.S. Appl. No. 12/900,046.
"Chemical Abstracts", Monatsch Chemistry Journal, vol. 96, No. 17, pp. 749, Abstract No. 142751b, 1982.
"The Merck Index", Twelfth Edition, Merck & Co., Inc., pp. 845, Monograph No. 4957, 1996.
Aboul-Fadl et al., 'Effective and Variable Functionalization of Pyrazolo[1,5-a]pryridines Involving Palladium-Catalyzed Coupling Reactions, Synthesis, vol. 12, pp. 1727-1732, 2000.
Armarego et al., "Purification of Laboratory Chemicals", 4th Edition, pp. 51, 1996.
Australian Notice of Allowance, dated Apr. 7, 2004, for Australian Application No. 20235/01.
Australian Notice of Allowance, dated Nov. 10, 2010, for Australian Application No. 2005233430.
Australian Office Action, dated Mar. 13, 2003, for Australian Application No. 20235/01.
Australian Office Action, dated May 4, 2010, for Australian Application No. 2005233430.
Australian Office Action, dated Nov. 25, 2003, for Australian Application No. 20235/01.
Australian submission of Search Report, dated May 15, 2003, for Australian Application No. 20235/01.
Brazilian Amendment, dated Feb. 25, 2005, for Brazilian Application No. PI0209252-2.
Brazilian Amendment, dated Oct. 30, 2008, for Brazilian Application No. PI0313976-0.
Brazilian Office Action, dated Feb. 3, 2011, for Brazilian Application No. PI0209252-2.
Canadian Amendment, dated Apr. 20, 2005, for Canadian Application No. 2394120.
Canadian Notice of Allowance, dated Dec. 10, 2007, for Canadian Application No. 2394120.
Chinese Notice of Allowance, dated Mar. 4, 2011, for Chinese Application No. 200580010906.0.
Chinese Notice of Allowance, dated Sep. 15, 2006, for Chinese Application No. 00817075.4.
Chinese Office Action, dated Apr. 11, 2008, for Chinese Application No. 200580010906.0.

Chinese Office Action, dated Mar. 25, 2010, for Chinese Application No. 200580010906.0.
Chinese Office Action, dated Nov. 26, 2004, for Chinese Application No. 00817075.4.
Chinese Office Action, dated Sep. 16, 2005, for Chinese Application No. 00817075.4.
European Amendment, dated Nov. 5, 2004, for European Application No. 00983479.7.
European Intent to Grant, dated Feb. 10, 2005, for European Application No. 03029058.9.
European Intent to Grant, dated Jul. 27, 2004, for European Application No. 00983479.7.
European Notice of Allowance, dated Jan. 20, 2005, for European Application No. 00983479.7.
European Notice of Allowance, dated Jun. 16, 2005, for European Application No. 03029058.9.
European Notice of Allowance, dated May 11, 2012, for European Application No. 09732907.2.
European Office Action, dated Feb. 21, 2003, for European Application No. 00983479.7.
European Office Action, dated Feb. 25, 2004, for European Application No. 00983479.7.
European Office Action, dated Jul. 11, 2003, for European Application No. 00983479.7.
European Office Action, dated Sep. 8, 2004, for European Application No. 03029058.9.
European Preliminary Amendment, dated Mar. 28, 2012, for European Application No. 10822051.8.
European Preliminary Amendment, dated Mar. 28, 2012, for European Application No. 10822057.5.
European Search Report, dated Feb. 25, 2004, for European Application No. 03029058.9.
Extended European Search Report, dated Oct. 13, 2010, for European Application No. 08840583.2.
Filipino Amendment, dated Jan. 5, 2005, for Filipino Application No. 1-2000-03412.
Filipino Amendment, dated Mar. 14, 2005, for Filipino Application No. 1-2000-03412.
Filipino Notice of Allowability, dated Nov. 29, 2007, for Filipino Application No. 1-2000-03412.
Filipino Office Action, dated Jul. 3, 2007, for Filipino Application No. 1-2000-03412.
Filipino Office Action, dated Mar. 21, 2002, for Filipino Application No. 1-2000-03412.
Filipino Office Action, dated May 5, 2006, for Filipino Application No. 1-2000-03412.
Gulf Cooperation Council Amendment, dated Dec. 5, 2010, for the Cooperation Council for the Arab States of the Gulf Application No. 13262.
Hu et al., 'Synthesis and Properties of Substituted Polyacetylenes Having Cyclohexyl Groups', Polymer Journal, vol. 39, No. 9, pp. 968-974, Jul. 31, 2007.
Indian Office Action, dated Aug. 25, 2011, for Indian Application No. 4147/CHENP/2006.
International Preliminary Examination Report, dated Dec. 19, 2001, for International Application No. PCT/JP00/08811.
International Preliminary Report on Patentability, dated May 11, 2010, for International Application No. PCT/JP2008/068822.
International Preliminary Report on Patentability, dated Oct. 19, 2006, for International Application No. PCT/JP2005/006928.
International Search Report, dated Dec. 16, 2008, for International Application No. PCT/JP2008/068822.
International Search Report, dated Jun. 7, 2005, for International Application No. PCT/JP2005/006928.
International Search Report, form PCT/ISA/210, dated Oct. 5, 2010, for International Application No. PCT/JP2010/063708.
Israeli Amendment, dated Jan. 10, 2011, for Israeli Application No. 158624.
Israeli Amendment, dated Jun. 30, 2009, for Israeli Application No. 167208.
Israeli Amendment, dated Nov. 18, 2008, for Israeli Application No. 167208.
Israeli Information Disclosure Statement, dated Apr. 5, 2009, for Israeli Application No. 178491.
Israeli Notice of Allowance, dated Dec. 23, 2009, for Israeli Application No. 167208.
Israeli Notice of Allowance, dated Jan. 11, 2011, for Israeli Application No. 158624.
Israeli Notice Prior to Examination, dated Jun. 5, 2011, for Israeli Application No. 208393.
Israeli Office Action, dated Aug. 5, 2009, for Israeli Application No. 158624.
Israeli Office Action, dated Aug. 5, 2010, for Israeli Application No. 158624.
Israeli Office Action, dated Dec. 26, 2010, for Israeli Application No. 178491.
Israeli Office Action, dated Jan. 25, 2010, for Israeli Application No. 178491.
Israeli Office Action, dated Mar. 12, 2007, for Israeli Application No. 158624.
Israeli Office Action, dated Mar. 30, 2008, for Israeli Application No. 158624.
Israeli Office Action, dated Nov. 27, 2007, for Israeli Application No. 167208.
Israeli Office Action, dated Sep. 15, 2011, for Israeli Application No. 178491.
Japanese Amendment, dated Feb. 21, 2012, for Japanese Application No. 2011-535430.
Japanese Amendment, dated Mar. 21, 2008, for Japanese Application No. 2006-512315.
Japanese Notice of Allowance, dated Apr. 3, 2012, for Japanese Application No. 2008-226399.
Japanese Notice of Allowance, dated Mar. 3, 2008, for Japanese Application No. 2000-375811.
Japanese Office Action, dated Jul. 26, 2011, for Japanese Application No. 2006-512315.
Japanese Office Action, dated Nov. 28, 2007, for Japanese Application No. 2000-375811.
Japanese Petition, dated Feb. 21, 2012, for Japanese Application No. 2011-535430.
Jones et al., "British Society of Gastronenterology guidlines for the management of the irritable bowel syndrome", GUT, vol. 47, Suppl II, ii1-ii19, 2000.
Khan et al., 'Tricyclic Heteroaromatic Ring Systems III. Synthesis of 1H,6H-Dipyrazolo [3,4-b:3',4'-d] pyridin-3-ones', Monatshefte fur Chemie, vol. 113, No. 1, pp. 123-127, Apr. 1982.
Klapars, et al., 'A General and Efficient Copper Catalyst for thet Amidation of Aryl Halides', Journal of American Chemical Society, vol. 124, pp. 7421-7428, 2002.
Korean Amendment, dated Dec. 10, 2004, for Korean Application No. 10-2002-7006902.
Korean Amendment, dated Jan. 26, 2007, for Korean Application No. 10-2002-7006902.
Korean Amendment, dated Sep. 29, 2006, for Korean Application No. 10-2002-7006902.
Korean Argument Brief, dated Jan. 26, 2007, for Korean Application No. 10-2002-7006902.
Korean Argument Brief, dated Sep. 29, 2006, for Korean Application No. 10-2002-7006902.
Korean Notice of Allowance, dated Mar. 15, 2007, for Korean Application No. 10-2002-7006902.
Korean Office Action, dated Jul. 1, 2011, Korean Application No. 10-2006-7021332.
Korean Office Action, dated Jul. 31, 2006, for Korean Application No. 10-2002-7006902.
Korean Office Action, dated Nov. 27, 2006, for Korean Application No. 10-2002-7006902.
Kosovan Amendment, dated Mar. 1, 2011, for Kosovan Application No. 329.
Nelson et al., "Behavioural abnormalities in male mice lacking neuronal nitric oxide synthase", Letters to Nature, vol. 378, pp. 383-386, Nov. 23, 1995.
New Zealand Notice of Acceptance, dated Dec. 9, 2004, for New Zealand Application No. 519241.

New Zealand Office Action, dated Feb. 17, 2004, for New Zealand Application No. 519241.
New Zealand Office Action, dated Nov. 9, 2004, for New Zealand Application No. 519241.
Poland Office Action, dated Apr. 16, 2012, for Poland Application No. P-367067.
Response to Australian Office Action, dated Feb. 23, 2004, for Australian Application No. 20235/01.
Response to Australian Office Action, dated Oct. 15, 2003, for Australian Application No. 20235/01.
Response to Australian Office Action, dated Oct. 18, 2010, for Australian Application No. 2005233430.
Response to Brazilian Office Action, dated Apr. 5, 2011, for Brazilian Application No. PI0209252-2.
Response to Chilean Office Action, dated Mar. 7, 2012, for Chilean Application No. 2009-000896.
Response to Chinese Office Action, dated Aug. 26, 2008, for Chinese Application No. 200580010906.0.
Response to Chinese Office Action, dated Dec. 1, 2005, for Chinese Application No. 00817075.4.
Response to Chinese Office Action, dated Mar. 28, 2005, for Chinese Application No. 00817075.4.
Response to Chinese Office Action, dated May 17, 2010, for Chinese Application No. 200580010906.0.
Response to European Office Action, dated Jan. 10, 2005, for European Application No. 03029058.9.
Response to European Office Action, dated Jun. 23, 2003, for European Application No. 00983479.7.
Response to European Office Action, dated Jun. 28, 2004, for European Application No. 00983479.7.
Response to European Office Action, dated Nov. 6, 2003, for European Application No. 00983479.7.
Response to Filipino Office Action, dated Jul. 23, 2007, for Filipino Application No. 1-2000-03412.
Response to Israeli Office Action, dated Dec. 4, 2011, for Israeli Application No. 178491.
Response to Israeli Office Action, dated Jul. 30, 2008, for Israeli Application No. 158624.
Response to to Israeli Office Action, dated Jul. 9, 2007, for Israeli Application No. 158624.
Response to Israeli Office Action, dated Mar. 19, 2008, for Israeli Application No. 167208.
Response to Israeli Office Action, dated Mar. 28, 2011, for Israeli Application No. 178491.
Response to Israeli Office Action, dated May 2, 2010, for Israeli Application No. 178491.
Response to Israeli Office Action, dated Oct. 13, 2010, for Israeli Application No. 158624.
Response to Israeli Office Action, dated Oct. 26, 2009, for Israeli Application No. 158624.
Response to Israeli Office Action, dated Sep. 18, 2011, for Israeli Application No. 208393.
Response to Japanese Office Action, dated Jan. 10, 2008, for Japanese Application No. 2000-375811.
Response to Japanese Office Action, dated Sep. 15, 2011, for Japanese Application No. 2006-512315.
Response to Korean Office Action, dated Aug. 29, 2011, for Korean Application No. 10-2006-7021332.
Response to New Zealand Office Action, dated Nov. 19, 2004, for New Zealand Application No. 519241.
Response to New Zealand Office Action, dated Nov. 3, 2004, for New Zealand Application No. 519241.
Response to Taiwanese Office Action, dated Dec. 7, 2007, for Taiwanese Application No. 91102009.
Response to Taiwanese Office Action, dated Feb. 25, 2004, for Taiwanese Application No. 91102009.
Response to Taiwanese Office Action, dated Oct. 13, 2008, for Taiwanese Application No. 91102009.
Response to US Office Action, dated Apr. 19, 2004, for U.S. Appl. No. 10/148,836.
Response to US Office Action, dated Jan. 16, 2004, for U.S. Appl. No. 10/148,836.
Response to US Office Action, dated Jan. 22, 2010, for U.S. Appl. No. 11/578,134.
Response to US Office Action, dated Jan. 24, 2005, for U.S. Appl. No. 10/903,059.
Response to US Office Action, dated Jan. 24, 2005, for U.S. Appl. No. 10/903,387.
Response to US Office Action, dated Jul. 1, 2010, for U.S. Appl. No. 11/578,134.
Response to US Office Action, dated May 4, 2009, for U.S. Appl. No. 11/578,134.
Response to US Office Action, dated Sep.,28, 2009, for U.S. Appl. No. 11/578,134.
Response to US Restriction/Election of Species Requirement, dated Mar. 22, 2012, for U.S. Appl. No. 12/900,026.
Response to US Restriction/Election of Species Requirement, dated Mar. 23, 2012, for U.S. Appl. No. 12/900,046.
Rodriguez-Spong et al., "General principles of pharmaceutical solid polymorphism: a supramolecular perspective", Advanced Drug Delivery Reviews, vol. 56, pp. 241-274, 2004.
Sato et al., "Studies on Cardiovascular Agents. 6. Synthesis and Coronary Vasodilating and Antihypertensive Activities of 1,2,4-Triazolo[1,5,-a]pyrimidines Fuse to Heterocyclic Systems", Journal of Medicinal Chemistry, American Chemical Society, vol. 23, No. 8, pp. 927-937, 1980.
Souillac, et al., "Characterization of Delivery Systems, Differential Scanning Calorimetry", Encyclopedia of Controlled Drug Delivery, pp. 212-227, 1999.
Supplementary Partial European Search Report, dated Dec. 4, 2002, for European Application No. 00983479.7.
Taiwanese Amendment, dated Apr. 12, 2004, for Taiwanese Application No. 89126373.
Taiwanese Amendment, dated Apr. 4, 2005, for Taiwanese Application No. 89126373.
Taiwanese Amendment, dated Mar. 8, 2012, for Taiwanese Application No. 098112062.
Taiwanese Amendment, dated Oct. 13, 2003, for Taiwanese Application No. 89126373.
Taiwanese Amendment, dated Sep. 14, 2006, for Taiwanese Application No. 89126373.
Taiwanese Claim Amendment, dated Apr. 4, 2005, for Taiwanese Application No. 89126373.
Taiwanese Claim Amendment, dated Sep. 14, 2006, for Taiwanese Application No. 89126373.
Taiwanese Notice of Allowance, dated May 27, 2009, for Taiwanese Application No. 91102009.
Taiwanese Notice of Allowance, dated Oct. 18, 2006, for Taiwanese Application No. 89126373.
Taiwanese Office Action, dated Aug. 31, 2006, for Taiwanese Application No. 89126373.
Taiwanese Office Action, dated Feb. 13, 2004, for Taiwanese Application No. 89126373.
Taiwanese Office Action, dated Jul. 14, 2008, for Taiwanese Application No. 91102009.
Taiwanese Office Action, dated Jul. 28, 2003, for Taiwanese Application No. 91102009.
Taiwanese Office Action, dated Mar. 17, 2003, for Taiwanese Application No. 89126373.
Taiwanese Office Action, dated Oct. 5, 2007, for Taiwanese Application No. 91102009.
Taiwanese Re-examination, dated Oct. 13, 2003, for Taiwanese Application No. 89126373.
Taiwanese Supplement and Modification, dated Apr. 12, 2004, for Taiwanese Application No. 89126373.
Taiwanese Supplement and Modification, dated Apr. 4, 2005, for Taiwanese Application No. 89126373.
Taiwanese Supplement and Modification, dated Sep. 14, 2006, for Taiwanese Application No. 89126373.
US Amendment, dated Aug. 2, 2004, for U.S. Appl. No. 10/903,059.
US Amendment, dated Aug. 2, 2004, for U.S. Appl. No. 10/903,387.
US Notice of Allowance, dated Feb. 25, 2005, for U.S. Appl. No. 10/903,059.
US Notice of Allowance, dated Feb. 25, 2005, for U.S. Appl. No. 10/903,387.

US Notice of Allowance, dated May 5, 2004, for U.S. Appl. No. 10/148,836.
US Notice of Allowance, dated Sep. 8, 2010, for U.S. Appl. No. 11/578,134.
US Office Action, dated Apr. 1, 2010, for U.S. Appl. No. 11/578,134.
US Office Action, dated Apr. 3, 2009, for U.S. Appl. No. 11/578,134.
US Office Action, dated Feb. 19, 2004, for U.S. Appl. No. 10/148,836.
US Office Action, dated Jun. 26, 2009, for U.S. Appl. No. 11/578,134.
US Office Action, dated Nov. 23, 2004, for U.S. Appl. No. 10/903,059.
US Office Action, dated Nov. 23, 2004, for U.S. Appl. No. 10/903,387.
US Office Action, dated Oct. 22, 2009, for U.S. Appl. No. 11/578,134.
US Office Action, dated Sep. 16, 2003, for U.S. Appl. No. 10/148,836.
Vietnamese Office Action, dated May 21, 2012, for Vietnamese Application No. 1-2010-03032.
Vippagunta et al., "Crystalline Solids", Advanced Drug Delivery Reviews, vol. 48, pp. 3-26, 2001.
Office Action dated May 24, 2012 for Chilean Application No. 896-09 with English translation.
U.S. Office Action dated Jun. 22, 2012 for U.S. Appl. No. 12/900,026.
English Translation of the International Preliminary Report on Patentability and Written Opinion of the International Searching Authority dated May 18, 2012 for International Application No. PCT/JP2010/067564 (Form PCT/IB/338, Form PCT/IB/373 and Form PCT/ISA/237).
Argentine Amendment, dated Jul. 26, 2010, for Argentine Application No. P-090101280.
Australian Amendment, dated Apr. 30, 2007, for Australian Application No. 2003275589.
Australian Amendment, dated Dec. 9, 2010, for Australian Application No. 2009237050.
Australian Notice of Acceptance, dated Jan. 3, 2007, for Australian Application No. 2002251546.
Australian Notice of Acceptance, dated May 18, 2009, for Australian Application No. 2003275589.
Australian Office Action, dated Aug. 21, 2006, for Australian Application No. 2002251546.
Australian Office Action, dated Aug. 21, 2008, for Australian Application No. 2003275589.
Australian Office Action, dated Sep. 14, 2006, for Australian Application No. 2002251546.
Australian Submission of Search Report, dated Jun. 15, 2005, for Australian Application No. 2002251546.
Bangladeshi Amendment, dated Aug. 1, 2010, for Bangladeshi Application No. 75/2009.
Polish Response dated Nov. 16, 2012 for PL Patent Application No. P-367067.
Russian Response dated Oct. 29, 2012 for RU Patent Application No. 2010146240 with English translation.
Office Action for Filipino Application No. 12010502102, dated Aug. 17, 2012.
Office Action for Indonesian Application No. W00201003905, dated Aug. 3, 2012, including an English translation.
Office Action for Mexican Application No. MX/a/2010/011089, dated Jul. 23, 2012, including an English translation.
Office Action for Polish Application No. P-367067, dated Sep. 17, 2012, including an English translation.
Office Action for Polish Application No. P-376132, dated Jul. 3, 2012, including an English translation.
Office Action for Russian Application No. 2010146240, dated Aug. 23, 2012, including an English translation.
Response (Submission Documents), dated Sep. 24, 2012, in Filipino Application No. 12010502102.
Response (Submission Documents), dated Sep. 7, 2012, in Polish Application No. P-376132, including a partial English translation.
Response to an Office Action for Filipino Application No. 1-2007-500806, dated Aug. 15, 2012.
Response to an Office Action for Mexican Application No. MX/a/2010/011089, dated Jun. 28, 2012, including an English translation.
Response to an Office Action for Polish Application No. P-367067, dated Aug. 17, 2012, including an English translation.
Response to an Office Action for U.S. Appl. No. 12/900,026, dated Sep. 19, 2012.
Response to Office Action for Vietamese Application No. 1-2010-03032, dated Jul. 11, 2012, including an English translation.
Shin et al., "Discovery of a novel, potent, selective, and orally active corticotropin-releasing factor 1 (CRF1) receptor antagonist, E2508, for the treatment of stress-related disorders such as anxiety and depression," 244th ACS National Meeting, Aug. 19-23, 2012, Philadelphia, Pennsylvania, 2 pages.
Takahashi et al., "Design, Synthesis, and Structure-Activity Relationships of Novel Pyrazolo[5,1-b]thiazole Derivatives as Potent and Orally Active Corticotropin-Releasing Factor 1 Receptor Antagonists," J. of Medicinal Chemistry, Just Accepted Manuscript, Sep. 12, 2012, 47 pages.
Takahashi et al., "Design, Synthesis, and Structure-Activity Relationships of Novel Pyrazolo[5,1-b]thiazole Derivatives as Potent and Orally Active Corticotropin-Releasing Factor 1 Receptor Antagonists," Journal of Medicinal Chemistry, Sep. 12, 2012, vol. 55, pp. 8450-8463.
Takahashi et al., "Synthesis and Structure-Activity Relationships of Pyrazolo[1,5-a]pyridine Derivatives: Potent and Orally Active Antagonists of Corticotropin-Releasing Factor 1 Receptor," Journal of Medicinal Chemistry, May 15, 2012, vol. 55, pp. 5255-5269.
Takeda et al., "Design, synthesis and structure-activity relationships of 5-alkylaminolquinolines as a novel series of CRF1 receptor antagonists," Bioorganic & Medicinal Chemistry Letters, vol. 22, 2012, pp. 4756-4761 (Available online May 24, 2012).
Takeda et al., "Design, synthesis and structure-activity relationships of a series of 2-Ar-8-methyl-5-alkylaminoquinolines as novel CRF1 receptor antagonists," Bioorganic & Medicinal Chemistry Letters, Accepted Manuscript, 2012, 45 pages.
Takeda et al., "Synthesis and Structure-Activity Relationships of 8-Substituted-2-aryl-5-alkylaminoquinolines: Potent, Orally Active Corticotropin-Releasing Factor-1 Receptor Antagonists," Bioorganic & Medicinal Chemistry, Accepted Manuscript, 2012, pp. 1-43.
Terauchi et al., "Discovery of a novel, potent, selective, and orally active corticotropin-releasing factor 1 (CRF1) receptor antagonist, E2009, for the treatment of stress-related disorders such as anxiety and depression," 244th ACS National Meeting, Philadelphia, PA, Aug. 19-23, 2012, 2 pages
Venezuelan Newspaper Advertisements, Sep. 7, 2011, with English translation.
Voluntary Amendment for Canadian Application No. 2,721,670, dated Sep. 5, 2012.
Filipino Completion of Final Requirements dated Nov. 8, 2012 for Filipino Appliation No. 1/2010/502102.
Polish Notice of Allowance dated Sep. 20, 2012, for PL Patent Application No. P376132.
Takeda et al., "Synthesis and Structure-Activity Relationships of 8-Substituted-2-aryl-5-alkylaminoquinolines: Potent, Orally Active Corticotropin-Releasing Factor-1 Receptor Antagonists," Bioorganic & Medicinal Chemistry, Sep. 23, 2012, pp. 6559-6578.
Vietnamese Notice of Allowance dated Oct. 26, 2012, for VN Patent Application No. 1-2010-03032.
Austrahan Office Action issued on Nov. 19. 2012 for AU Patent Application No. 2009237050.
Canadian Notice of Allowance dated Jan. 7, 2013, for CA Patent Application No. 2721670, with English translation.
Chinese Office Action dated Dec. 3, 2012, for CN Application No. 200980113130.3, with English translation.
Indonesian Notice of Allowance dated Jan. 11, 2013, for ID Application No. W-00201003905, including an English translation.
Israeli Notice of Non-Substantive Deficiencies Prior to Allowance of Patent Application dated Jan. 6, 2013, for IL Patent Application No. 208393, with English translation.
Polish Notice of Allowance dated Dec. 20, 2012, for PL Patent Application No. P-367067, with English translation.

Response to Chinese Office Action dated Jan. 25, 2013, for CN Application No. 200980113130.3, with English translation.
Response to Filipino Completion of Final Requirements dated Dec. 12, 2012 for Filipino Application No. 1-2010-502102.
Response to Indonesian Office Action dated Dec. 14, 2012, for Application No. W-00201003905, including an English translation.
Russian Decision on Grant dated Dec. 5, 2012, for RU Patent Application No. 2010146240, with English translation.
Ukranian Notice of Allowance dated Dec. 24, 2012, for UA Application No. 201013461, with English translation.
United States Notice of Allowance dated Jan. 23, 2013, for U.S. Appl. No. 12/900,026.

3-PHENYLPYRAZOLO[5,1-*B*]THIAZOLE COMPOUNDS

RELATED APPLICATIONS

This application claims priority to U.S. provisional application 61/045,084 filed on Apr. 15, 2008 as well as Japanese Patent Application 2008-106,080 filed on Apr. 15, 2008, both of which are herein incorporated by reference by in their entireties.

BACKGROUND OF THE INVENTION

1. Field of the Invention

The present invention relates to novel compounds having antagonism against corticotropin-releasing factor (hereunder, "CRF") receptor, salts thereof and medical use of the same.

2. Related Background of the Invention

CRF is a neuropeptide consisting of 41 amino acids which is produced and secreted in the hypothalamus and promotes release of adrenocorticotropic hormone (ACTH) under stress, and it also functions in the brain as a neurotransmitter or neuromodulator, integrating electrophysiology, autonomic nerves and behavior in response to stress.

CRF receptors are of two subtypes, CRF1 receptors and CRF2 receptors, of which CRF1 receptors have been reported to be widely distributed in the cerebral cortex, cerebellum, olfactory bulb, pituitary gland, amygdaloid nucleus and elsewhere.

Numerous low molecular compounds having CRF receptor antagonism have been noted as potential therapeutic agents for a number of diseases including depression, anxiety and stress-related disorders. (See Non-patent document 1)

Disclosed compounds having CRF receptor antagonism include 2,6-dimethoxy-4-methoxymethylphenyl-containing compounds (see Patent document 1), but compounds having a pyrazolo[5,1-b]thiazole skeleton according to the present invention have been neither disclosed nor suggested.

The compound shown below has been disclosed as a compound having a pyrazolo[5,1-b]thiazole skeleton, but its use is for colorimetry. (See Example 16 of Patent document 2)

[Chemical Formula 1]

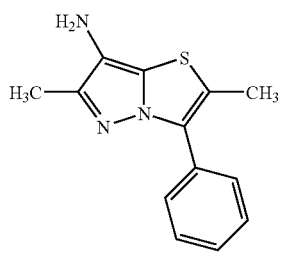

[Patent document 1] U.S. Patent Application Publication No. 2004/0224974
[Patent document 2] U.S. Pat. No. 5,234,818
[Non-patent document 1] Drugs of the Future, 24:1089-1098 (1999)

SUMMARY OF THE INVENTION

Absolutely no 3-phenylpyrazolo[5,1-b]thiazole compounds having superior CRF receptor antagonism are known. Furthermore, although compounds having CRF receptor antagonism have been reported, they have not necessarily been adequate in terms of exhibiting superior CRF receptor antagonism, and in terms of having sufficient pharmacological activity, safety and pharmacokinetic properties as medicaments.

As a result of diligent research in light of the current circumstances, the present inventors have discovered novel compounds that are excellent CRF receptor antagonists with sufficient pharmacological activity, safety and pharmacokinetic properties, which are therefore useful as prophylactic or therapeutic agents for depression, anxiety, irritable bowel syndrome and the like.

Specifically, the invention relates to the following.

<1> A compound represented by the following formula (I) or salt thereof.

[Chemical Formula 2]

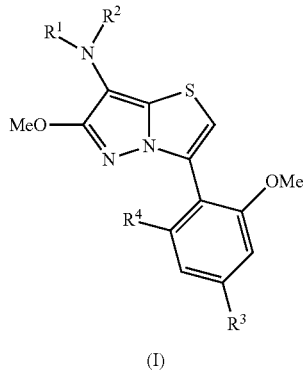

wherein
$R^1$ represents the formula $-A^{11}-A^{12}$;
$R^2$ represents tetrahydrofurylmethyl, tetrahydropyranylmethyl or tetrahydropyranyl;
$A^{11}$ represents a single bond, methylene group or 1,2-ethylene;
$A^{12}$ represents C1-6 alkyl or C3-6 cycloalkyl, or C3-6 cycloalkyl having methyl;
$R^3$ represents methoxy, cyano, cyclobutyloxymethyl, methoxymethyl or ethoxymethyl; and
$R^4$ represents methoxy group or chlorine.

<2> A compound or salt thereof according to <1> above, wherein $R^2$ is tetrahydropyran-4-yl, tetrahydropyran-3-yl, (tetrahydropyran-4-yl)methyl or (tetrahydrofuran-3-yl)methyl.

<3> A compound or salt thereof according to <1> or <2> above, wherein $R^1$ is n-propyl, n-butyl, n-pentyl, cyclopropylmethyl, cyclobutylmethyl, 2-(cyclopropyl)ethyl or (2-methylcyclopropyl)methyl.

<4> A pharmaceutical composition comprising a compound or salt thereof according to any one of <1> to <3> above as an active ingredient.

<5> A pharmaceutical composition according to <4> above, which is a CRF1 receptor antagonist.

<6> A therapeutic or prophylactic agent for a disease for which CRF1 receptor antagonist is effective, comprising a compound or salt thereof according to any one of <1> to <3> above.

<7> A therapeutic or prophylactic agent for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia, which comprises a compound or salt thereof according to any one of <1> to <3> above.

<8> A therapeutic or prophylactic agent for depression, depressive symptoms, anxiety or irritable bowel syndrome, comprising a compound or salt thereof according to any one of <1> to <3> above.

<9> A method for treatment or prevention of depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia, comprising administering to a patient, a compound or salt thereof according to any one of <1> to <3> above.

<10> A method for treatment or prevention of depression, depressive symptoms, anxiety or irritable bowel syndrome, comprising administering to a patient, a compound or salt thereof according to any one of <1> to <3> above.

<11> A compound or salt thereof according to any one of <1> to <3> above for treatment or prevention of depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia.

<12> A compound or salt thereof according to any one of <1> to <3> above for treatment or prevention of depression, depressive symptoms, anxiety or irritable bowel syndrome.

<13> Use of a compound or salt thereof according to any one of <1> to <3> above for the manufacture of a therapeutic or prophylactic agent for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia.

<14> Use of a compound or salt thereof according to any one of <1> to <3> above for the manufacture of a therapeutic or prophylactic agent for depression, depressive symptoms, anxiety or irritable bowel syndrome.

<15-1> N-Butyl-3-[2,6-dimethoxy-4-(methoxymethyl)phenyl]-6-methoxy-N-(tetrahydro-2H-pyran-4-yl)pyrazolo[5,1-b][1,3]thiazole-7-amine or salt thereof.

<15-2> N-Butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine or salt thereof.

<15-3> N-(2-Cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine or salt thereof.

<15-4> N-(Cyclobutylmethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine or salt thereof.

<15-5> N-(Cyclopropylmethyl)-3-[4-(ethoxymethyl)-2,6-dimethoxyphenyl]-6-methoxy-N-(tetrahydro-2H-pyran-3-yl)pyrazolo[5,1-b][1,3]thiazole-7-amine or salt thereof.

<15-6> 3-[4-(Ethoxymethyl)-2,6-dimethoxyphenyl]-6-methoxy-N-propyl-N-(tetrahydro-2H-pyran-3-yl)pyrazolo[5,1-b][1,3]thiazole-7-amine or salt thereof.

<15-7> N-(Cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine or salt thereof.

<15-8> 3-[2,6-Dimethoxy-4-(methoxymethyl)phenyl]-6-methoxy-N-pentyl-N-(tetrahydro-2H-pyran-4-yl)pyrazolo[5,1-b][1,3]thiazole-7-amine or salt thereof.

<15-9> N-(Cyclopropylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine or salt thereof.

<15-10> 3-[2,6-Dimethoxy-4-(methoxymethyl)phenyl]-6-methoxy-N-propyl-N-(tetrahydro-2H-pyran-4-yl)pyrazolo[5,1-b][1,3]thiazole-7-amine or salt thereof.

<15-11> N-(Cyclopropylmethyl)-3-[2,6-dimethoxy-4-(methoxymethyl)phenyl]-6-methoxy-N-(tetrahydro-2-pyran-3-yl)pyrazolo[5,1-b][1,3]thiazole-7-amine or salt thereof.

<15-12> 3-[2,6-Dimethoxy-4-(methoxymethyl)phenyl]-6-methoxy-N-[(2-methylcyclopropyl)methyl]-N-(tetrahydro-2H-pyran-4-yl)pyrazolo[5,1-b][1,3]thiazole-7-amine or salt thereof.

<15-13> 3-[2-Chloro-6-methoxy-4-(methoxymethyl)phenyl]-6-methoxy-N-propyl-N-(tetrahydro-2H-pyran-4-yl)pyrazolo[5,1-b][1,3]thiazole-7-amine or salt thereof.

<15-14> 4-{7-[(Cyclopropylmethyl)(tetrahydrofuran-3-ylmethyl)amino]-6-methoxypyrazolo[5,1-b][1,3]thiazol-3-yl}-3,5-dimethoxybenzonitrile or salt thereof.

<15-15> 4-{7-[(Cyclopropylmethyl)(tetrahydro-2H-pyran-4-ylmethyl)amino]-6-methoxypyrazolo[5,1-b][1,3]thiazol-3-yl}-3,5-dimethoxybenzonitrile or salt thereof.

<15-16> N-(Cyclopropylmethyl)-6-methoxy-N-(tetrahydro-2H-pyran-4-ylmethyl)-3-(2,4,6-trimethoxyphenyl)-pyrazolo[5,1-b][1,3]thiazole-7-amine or salt thereof.

<15-17> 3-{4-[(Cyclobutyloxy)methyl]-2,6-dimethoxyphenyl}-6-methoxy-N-propyl-N-(tetrahydro-2H-pyran-4-yl)pyrazolo[5,1-b][1,3]thiazole-7-amine or salt thereof.

CRF receptor antagonists have been reported to be effective for a wide range of diseases, which are listed below.

(1) Depression, Depressive Symptoms, Anxiety

CRF1 receptor antagonist R121919 is effective for ameliorating depression, depressive symptoms, anxiety and the like. (Journal of Psychiatric Research, 34:171-181 (2000))

CRF1 receptor antagonist R121919 exhibits an anti-anxiety action in rats. (European Journal of Neuroscience, 13:373-380 (2001))

CRF1 receptor antagonist CP-154526 exhibits anti-depressant and anti-anxiety actions in rats. (European Journal of Pharmacology, 492:195-201 (2004))

(2) Irritable Bowel Syndrome (IBS)

CRF1 receptor antagonist α-helical CRF(9-41) inhibits colon intestinal hyperkinesis in IBS patients and reduces abdominal pain and anxiety. (Gut 2004; 53:958-964)

(3) Sleep Disorder, Insomnia

CRF1 receptor antagonist R121919 inhibits stress-related sleep disorder particularly in high-anxiety rats. (Journal of Psychiatric Research, 36:197-208 (2002))

(4) Alcohol Dependence, Alcohol Withdrawal Symptoms, Drug Dependence, Drug Withdrawal Symptoms CRF1 receptor antagonist CP-154526 inhibits recurrence of stress-elicited alcohol-seeking behavior in rats. (Psychopharmacology, 150:317-324 (2000))

CRF1 receptor antagonist α-helical CRF(9-41) inhibits anxiety behavior in ethanol withdrawal rats. (Brain Research, 605:25-32 (1993))

CRF1 receptor antagonist CP-154526 inhibits recurrence of stress-elicited drug (heroin, cocaine)-seeking behavior in rats. (Psychopharmacology, 137:184-190 (1998))

Pretreatment with CRF1 receptor antagonist CP-154526 inhibits naltrexone-induced morphine withdrawal symptoms. (Journal of Neurochemistry, 74:199-208 (2000))

(5) Stress-Related Gastrointestinal Dysfunction

CRF1 receptor antagonist NBI-27914 inhibits water avoidance stress-related rat catharsis. (Brain Research, 893:29-35 (2001))

(6) Anorexia Nervosa, Eating Disorder

CRF1 receptor antagonists α-helical CRF(9-41) and CRA1000 inhibit stress-related reduction in food intake. (Brain Research, 823:221-225 (1999))

(7) Postoperative Ileus

CRF1 receptor antagonist CP-154526 ameliorates gastric emptying retardation following surgery. (Gastroenterology, 125:654-659 (2003))

(8) Dementia, Alzheimer-Type Senile Dementia, Multi-Infarct Dementia, Senile Dementia CRF1 receptor antagonist CP-154526 inhibits learning disturbance following acute stress. (Behavioural Brain Research, 138:207-213 (2003))

CRF1 receptor antagonist α-helical CRF(9-41) suppresses stress-related increase in intracerebral amyloid-β. (Proceedings of the National Academy of Sciences of the United States of America, 104:10673-10678 (2007))

CRF1 receptor antagonist NBI27914 inhibits increased levels of Aβ and Aβ plaque deposition induced by stress in Tg2576 mice (Journal of Neurochemistry, 108: 165-175 (2009))

CRF1 receptor antagonist antalarmin inhibits stress-induced hippocampal tau phosphorylation (Journal of Neuroscience, 27 (24): 6552-6562 (2007))

(9) Ischemic Neuropathy, Apoplexy

CRF1 receptor antagonist α-helical CRF(9-41) inhibits ischemic and excitotoxic encephalopathy. (Brain Research, 656:405-408 (1994))

(10) Excitotoxic Neuropathy

CRF1 receptor antagonist Asressin inhibits kainic acid-induced excitotoxic neuropathy. (Brain Research, 744:166-170 (1997))

(11) Convulsion, Epilepsy

CRF1 receptor antagonist NBI27914 inhibits limbic system seizure (convulsion and epilepsy induced by CRF administration). (Brain Research, 770:89-95 (1997))

(12) Hypertension

CRF1 receptor antagonist Antalarmin inhibits hypertension induced by intraventricular administration of CRF. (Brain Research, 881:204-207 (2000))

The compounds and salts thereof according to the invention have excellent CRF receptor antagonism, as evidenced by the activity data in the Pharmacological Test Examples described below. Thus, based on the aforementioned publications demonstrating a correlation between CRF receptor antagonism and effects of treating or preventing diseases, the compounds or salts thereof according to the invention are useful for treatment or prevention of diseases associated with CRF and/or CRF receptors, and are particularly useful as therapeutic or prophylactic agents for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia.

DESCRIPTION OF THE PREFERRED EMBODIMENTS

The present invention will now be explained in detail.

Throughout the present specification, the structural formulas for the compounds will show only one specific isomer for convenience, but the invention includes all isomers such as geometric isomers, optical isomers, stereoisomers and tautomers implied by the compound structures, as well as their isomer mixtures, and the compounds may therefore be any of the isomers or mixtures thereof in any desired proportion, without being limited to the formulas that are shown for convenience. Thus, for example, the compounds of the invention may exist as optically active forms or racemic mixtures, all of which are included without limitations according to the invention, and whether racemic mixtures or optically active forms, they may be used as mixtures with the optically active forms in any desired proportion.

Polymorphic crystals may also exist, and there may be used any crystal form or a mixture thereof without any restrictions, as well as amorphous forms, and the compounds of the invention also include both anhydrate and solvate (especially hydrate). The invention further encompasses metabolites of compound (I) according to the invention, that are produced by metabolism (oxidation, reduction, hydrolysis, conjugation and the like) in the body. The invention still further encompasses compounds that yield compound (I) according to the invention by metabolism (oxidation, reduction, hydrolysis, conjugation and the like) in the body (so-called prodrugs).

The meanings of the terms and symbols used throughout the present specification will now be explained, followed by a more detailed description of the invention.

The term "C1-6 alkyl" used throughout the present specification refers to C1-6 straight-chain or branched alkyl groups, and as specific examples there may be mentioned methyl, ethyl, 1-propyl (n-propyl), 2-propyl (i-propyl), 2-methyl-1-propyl (i-butyl), 2-methyl-2-propyl (tert-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl and 2,3-dimethyl-2-butyl.

The term "C3-6 cycloalkyl" used throughout the present specification refers to C3-6 monocyclic saturated aliphatic hydrocarbon groups, and as specific examples there may be mentioned cyclopropyl, cyclobutyl, cyclopentyl and cyclohexyl.

As specific examples of the "C3-6 cycloalkyl having methyl" referred to throughout the present specification there may be mentioned 2-methylcyclobutyl, 3-methylcyclobutyl and 2-methylcyclopropyl, among which 2-methylcyclopropyl is preferred.

As specific examples of "tetrahydropyranyl" referred to throughout the present specification there may be mentioned tetrahydropyran-4-yl and tetrahydropyran-3-yl, with tetrahydropyran-4-yl being preferred.

As specific examples of "tetrahydropyranylmethyl" referred to throughout the present specification there may be mentioned (tetrahydropyran-4-yl)methyl, (tetrahydropyran-3-yl)methyl and (tetrahydropyran-2-yl)methyl, among which (tetrahydropyran-4-yl)methyl is preferred.

As specific examples of "tetrahydrofurylmethyl" referred to throughout the present specification there may be mentioned (tetrahydrofuran-3-yl)methyl and (tetrahydrofuran-2-yl)methyl, with (tetrahydrofuran-3-yl)methyl being preferred.

The term "anxiety" used in the present specification refers not only to anxiety in the strict sense, but also to conditions within the general concept of anxiety, such as generalized anxiety disorder, panic disorder, phobia, obsessive compulsive disorder and post-traumatic stress disorder, as well as diseases closely related to anxiety.

The term "dementia" used in the present specification refers not only to dementia in the strict sense, but also conditions within the general concept of dementia, such as Alzheimer-type senile dementia, multi-infarct dementia and senile dementia, as well as diseases closely related to dementia.

A "salt" used in the present specification is not particularly restricted so long as it is formed with the compound of the invention, although it is preferably a pharmacologically acceptable salt, and as specific examples there may be mentioned inorganic acid salts, organic acid salts and acidic amino acid salts.

A "salt" used in the present specification, unless otherwise specified, may form a salt with an appropriate ratio, and the number of the acid molecule against one molecule of the compound is not particularly restricted, but preferably approximately 0.1 to approximately 5 molecules of the acid exist against one molecule of the compound, more preferably approximately 0.5 to approximately 2 molecules of the acid exist against one molecule of the compound, and even more preferably approximately 0.5, approximately 1 or approximately 2 molecules of the acid exist against one molecule of the compound.

As preferred examples of inorganic acid salts there may be mentioned hydrochloride, hydrobromide, sulfate, nitrate and phosphate, and as preferred examples of organic acid salts there may be mentioned acetate, succinate, fumarate, malate, tartrate, citrate, lactate, stearate, benzoate, methanesulfonate and p-toluenesulfonate.

As preferred examples of acidic amino acid salts there may be mentioned aspartate and glutamate.

(General Production Schemes)

General production schemes for compounds according to the invention will be outlined below, although they are not intended to be restrictive. The starting compounds and reagents used in the general production schemes for compounds of the invention may also form salts or solvates (especially hydrates).

The compounds represented by general formula (I) of the invention can be produced by the following production schemes.

Production Scheme 1

[Chemical Formula 3]

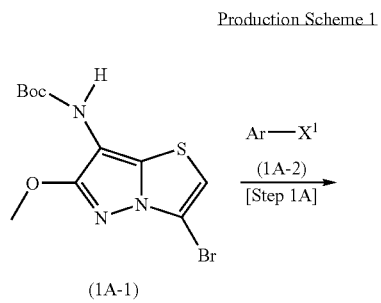

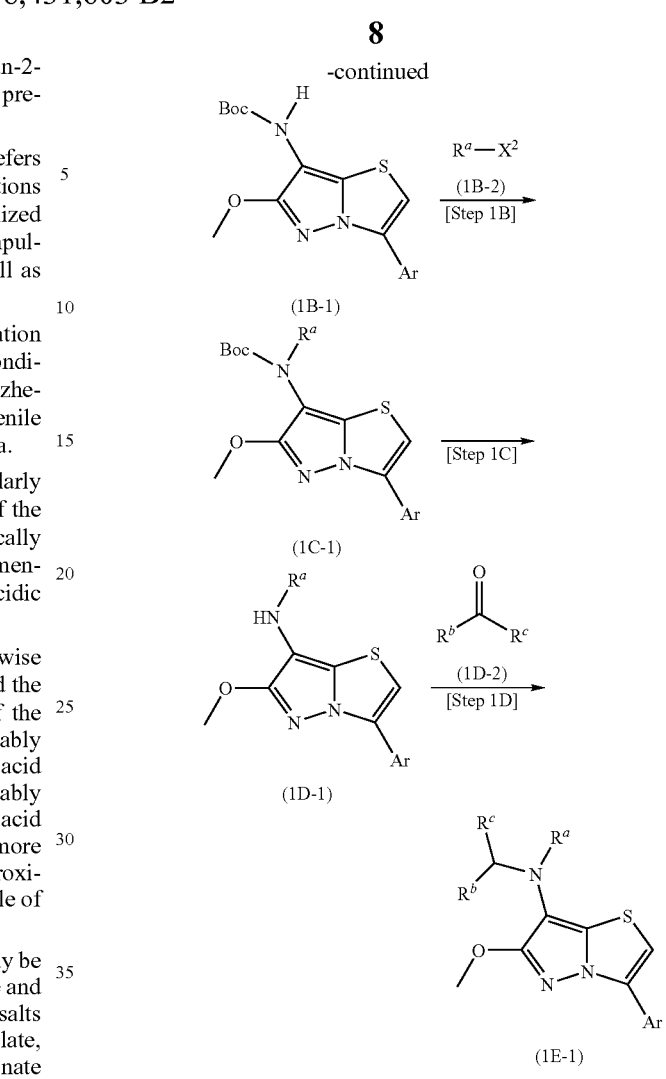

wherein Ar corresponds to the group represented by the formula:

[Chemical Formula 4]

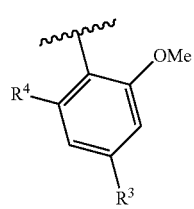

in compound (I) described above;

$R^a$ and the group represented by the formula:

[Chemical Formula 5]

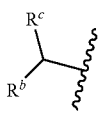

each independently corresponds to $R^1$ or $R^2$ above;

$X^1$ represents $B(OH)_2$ or the like;

$X^2$ represents a leaving group such as iodine, bromine, chlorine, methanesulfonyloxy or p-toluenesulfonyloxy; and Boc represents tert-butoxycarbonyl.

Step 1A

This is a step of reacting compound (1A-1) and compound (1A-2) in a solvent in the presence of a base and a palladium catalyst to produce compound (1B-1).

The step can be carried out with reference to the reaction conditions described in WO 04/037822 (step 5-E of Production Process 5, Example 47) and in (2f) of Example 2 below and the like.

The compounds represented by general formula (1A-1) can be produced according to (2e) of Example 2 and the like.

For a compound represented by general formula (1A-2) there may be used a compound that can be produced under the reaction conditions described in WO 04/037822 (Production Examples 29 and 33) and in Production Examples 1C(3) and 2C(6) and Examples 16(b) and 17(d) below and the like. For a compound represented by general formula (1A-2) there may be used any commercially available compound, or a compound that can be easily produced by a person skilled in the art from a commercially available compound.

The reaction may be carried out under a stream or in an atmosphere of an inert gas such as nitrogen or argon.

The solvent used for the reaction is not particularly restricted so long as it dissolves the starting materials to some extent and does not interfere with the reaction, and examples include alcohol solvents such as methanol, ethanol and n-butanol, ether solvents such as tetrahydrofuran, 1,2-dimethoxyethane, methyl-tert-butyl ether, cyclopentyl methyl ether, diethyl ether, diisopropyl ether, dibutyl ether, dicyclopentyl ether, 1,2-dimethoxyethane and 1,4-dioxane, aromatic hydrocarbon solvents such as benzene, toluene, xylene and mesitylene, amide solvents such as N,N-dimethylformamide, aliphatic hydrocarbon solvents such as heptane and hexane, or 1-methyl-2-pyrrolidinone, water, and mixtures thereof, among which preferred solvents are water, alcohol solvents, aromatic hydrocarbon solvents, ether solvents and mixtures thereof, and more preferred solvents are a mixed solvent of ethanol and toluene, or a mixed solvent of 1,2-dimethoxymethane and water.

The base used in this step is not particularly restricted and will differ depending on the starting material and solvent used, but examples include inorganic bases such as lithium hydroxide, sodium hydroxide, potassium hydroxide, barium hydroxide, lithium carbonate, sodium carbonate, potassium carbonate, sodium hydrogencarbonate, potassium hydrogencarbonate, cesium carbonate, cesium fluoride and potassium fluoride, cyclic bases such as imidazole and pyridine and organic amines such as triethylamine and N,N-diisopropylethylamine, among which sodium carbonate and potassium carbonate are preferred.

The palladium catalyst is not particularly restricted so long as it does not interfere with the reaction, and will differ depending on the starting material and solvent used, but as preferred examples there may be mentioned tetrakis(triphenylphosphine)palladium(0), palladium(II) acetate/triphenylphosphine, palladium(II) acetate/2-dicyclohexylphosphino-2',4',6'-triisopropylbiphenyl, palladium(II) chloride, tris(dibenzylideneacetone)dipalladium(0)/tri-tert-butylphosphine and dichloro[1,1'-bis(diphenylphosphine)-ferrocene]palladium(0).

The reaction temperature will generally differ depending on the starting materials, solvent and other reagents used in the reaction, but it is preferably between 0° C. and the reflux temperature of the solvent (as the reactor internal temperature), and more preferably 60° C.-100° C.

The reaction time will also, in general, differ depending on the starting materials, solvent and other reagents used in the reaction, and on the reaction temperature, but it is preferably 1-48 hours and more preferably 1-6 hours at the aforementioned reaction temperature after addition of the reagents.

Compound (1A-2) may be used at 1-5 molar equivalents and preferably 1-3 molar equivalents with respect to compound (1A-1).

The aforementioned base may be used at 1-10 molar equivalents and preferably 2-5 molar equivalents with respect to compound (1A-1).

The palladium catalyst may be used at 0.01-1 molar equivalents and preferably 0.05-0.1 molar equivalents with respect to compound (1A-1).

Step 1B

This is a step of reacting compound (1B-1) and compound (1B-2) in a solvent in the presence of a base to produce compound (1C-1).

The step can be carried out with reference to the reaction conditions described in WO 04/037822 (step 5-A of Production Process 5, and Production Example 24) and in (2 g) of Example 2 below and the like.

The reaction may be carried out under a stream or in an atmosphere of an inert gas such as nitrogen or argon.

Compound (1B-2) may be a compound that can be produced under the reaction conditions described in Production Example 1B below and the like. Compound (1B-2) may be a commercially available compound, or a compound that can be easily produced by a person skilled in the art from a commercially available compound.

The solvent used for this reaction is not particularly restricted so long as it dissolves the starting materials to some degree and does not interfere with the reaction, and for example, there may be used nitrile solvents such as acetonitrile, ether solvents such as tetrahydrofuran, 1,2-dimethoxyethane, methyl-tert-butyl ether, cyclopentyl methyl ether, diethyl ether, diisopropyl ether, dibutyl ether and dicyclopentyl ether, aromatic hydrocarbon solvents such as benzene and toluene, amide solvents such as N,N-dimethylformamide, aliphatic hydrocarbon solvents such as heptane and hexane, dimethyl sulfoxide, or mixtures thereof, among which N,N-dimethylformamide and dimethyl sulfoxide are preferred.

The base used for this step is not particularly restricted and will differ depending on the starting material and solvent used, but as examples there may be mentioned inorganic bases such as lithium hydroxide, sodium hydroxide, potassium hydroxide, lithium carbonate, sodium carbonate, potassium-tert-butoxide, butyllithium, methyllithium, lithium hydrogencarbonate and cesium carbonate, organometallic bases such as potassium-tert-butoxide, butyllithium, methyllithium, lithium bis(trimethylsilyl)amide, sodium bis(trimethylsilyl)amide and potassium bis(trimethylsilyl)amide, hydride bases such as lithium hydride, sodium hydride and potassium hydride, cyclic bases such as imidazole, pyridine and 4-dimethylaminopyridine, and organic amines such as triethylamine and N,N-diisopropylethylamine, among which sodium hydride and sodium hydroxide are preferred.

The reaction temperature will generally differ depending on the starting materials, solvent and other reagents used in the reaction, but it is preferably 0° C.-80° C. (as the reactor internal temperature).

The reaction time will generally differ depending on the starting materials, the solvent and the other reagents used in the reaction, and on the reaction temperature, but preferably stirring is carried out for 1-8 hours at the aforementioned reaction temperature after addition of the reagents.

Compound (1B-2) may be used at 1-5 moles with respect to compound (1B-1).

The base may be used at 1-5 molar equivalents and preferably 1.5 molar equivalents with respect to compound (1B-1).

Step 1C

This is a step of acid treatment of compound (1C-1) to produce compound (1D-1).

The step can be carried out with reference to the reaction conditions described in WO 04/037822 (step 5-B of Production Process 5, and Production Example 24) and in (2 g) of Example 2 below and the like.

This step can be carried out in the presence or in the absence of a solvent, and when a solvent is used, the solvent used for the reaction is not particularly restricted so long as it can dissolve the starting materials to some extent and does not interfere with the reaction, and examples include ether solvents such as tetrahydrofuran, 1,2-dimethoxyethane, methyl-tert-butyl ether, cyclopentyl methyl ether, diethyl ether, diisopropyl ether, dibutyl ether, dicyclopentyl ether and 1,4-dioxane, aromatic hydrocarbon solvents such as benzene and toluene, aliphatic hydrocarbon solvents such as heptane and hexane, ethyl acetate, halogen solvents such as dichloromethane, acetonitrile, and mixtures thereof, with dichloromethane being preferred.

The acid used in this step may be hydrochloric acid, sulfuric acid, trifluoroacetic acid or the like, with trifluoroacetic acid being preferred.

The reaction temperature will generally differ depending on the starting materials, solvent and other reagents used in the reaction, but it is preferably 0° C.-40° C. (as the reactor internal temperature).

The reaction time will also differ in most cases depending on the starting materials, the solvent and the other reagents used in the reaction, and on the reaction temperature, but preferably stirring is carried out for 1-8 hours at the aforementioned reaction temperature after addition of the reagents.

The acid may be used in an amount of 1 mol or more with respect to compound (1C-1), and a large excess of acid may also be used as the reaction solvent.

The product of step 1B and step 1C may be used as starting material for the subsequent step without any special purification, with only a procedure of simple treatment of the reaction mixture and distilling off the solvent, similar to (2 g) in Example 2 described below.

Step 1D

This is a step of reacting compound (1D-1) and compound (1D-2) in a solvent, in the presence of a reducing agent and in the presence or in the absence of an acid, to produce compound (1E-1).

The step can be carried out with reference to the reaction conditions described in WO 04/037822 (step 5-C of Production Process 5, and Production Example 24) and in (2 g) of Example 2 and the like.

The reaction may be carried out under a stream or in an atmosphere of an inert gas such as nitrogen or argon.

Compound (1D-2) may be an aldehyde compound or ketone compound as defined above, and there may be used a compound that can be produced under the reaction conditions described in Production Example 1A below and the like, a commercially available compound, or a compound that can be easily produced by a person skilled in the art from a commercially available compound using ordinary methods.

The solvent used for this reaction is not particularly restricted so long as it dissolves the starting materials to some degree and does not interfere with the reaction, and as examples there may be mentioned alcohol solvents such as methanol and ethanol, ether solvents such as tetrahydrofuran, 1,2-dimethoxyethane, methyl-tert-butyl ether, cyclopentyl methyl ether, diethyl ether, diisopropyl ether, dibutyl ether and dicyclopentyl ether or acetic acid and the like, any of which may be used alone or as mixed solvents.

The reducing agent may be a reducing agent that is commonly used for reductive amination between carbonyl compounds and amine compounds and is not particularly restricted for this reaction, and α-picolineborane, sodium triacetoxyborohydride and sodium borohydride may be mentioned as examples.

The acid used for the reaction may be trifluoroacetic acid, acetic acid and the like.

The reaction temperature will generally differ depending on the starting materials, solvent and other reagents used in the reaction, but it is preferably between 0° C. and the reflux temperature of the solvent (as the reactor internal temperature), and is more preferably room temperature.

The reaction time will also, in general, differ depending on the starting materials, solvent and other reagents used in the reaction, and on the reaction temperature, but it is preferably 1-48 hours and more preferably 1-6 hours at the aforementioned reaction temperature after addition of the reagents.

The reducing agent may be used at 0.5-3 molar equivalents and preferably 1-2 molar equivalents with respect to compound (1D-1).

Compound (1D-2) may be used at 1-5 molar equivalents and preferably 1-2 molar equivalents with respect to compound (1D-1).

Production Scheme 2

[Chemical Formula 6]

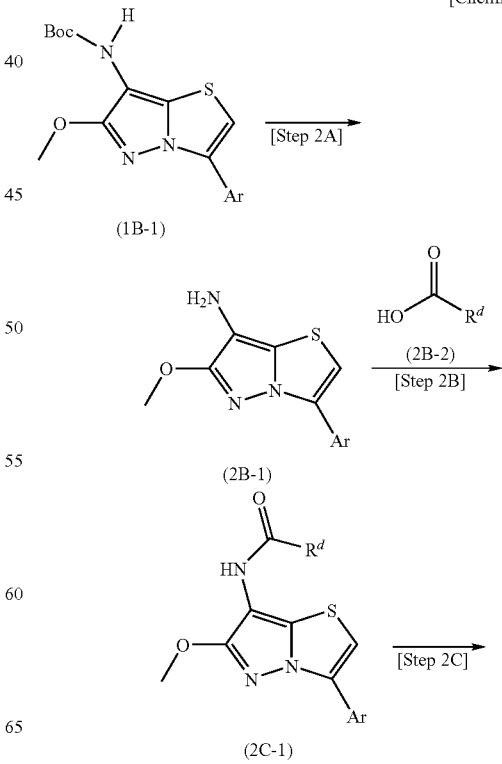

-continued (2D-1)

(1D-2)
[Step 2D]

(2E-1)

wherein Ar is a group represented by the formula:

[Chemical Formula 7]

Boc has the same definition as above, and
the group represented by $R^d$—$CH_2$— corresponds to $R^1$ or $R^2$.

Step 2A

This is a step of acid treatment of compound (1B-1) to produce compound (2B-1).

This step may be carried out under the reaction conditions described for step 1C of Production Scheme 1, or with reference to the reaction conditions described in (12a) of Example 12 below and the like.

The solvent used for the reaction is not particularly restricted so long as it dissolves the starting materials to some extent and does not interfere with the reaction, and for example, ethyl acetate, water or a mixed solvent thereof may be used.

The acid used in this step may be hydrochloric acid, sulfuric acid, trifluoroacetic acid and the like, but it is preferably a solution of hydrochloric acid in ethyl acetate, or trifluoroacetic acid.

The reaction temperature will generally differ depending on the starting materials, solvent and other reagents used in the reaction, but it is preferably 0° C.-40° C.

The reaction time will also, in general, differ depending on the starting materials, solvent and other reagents used in the reaction, and on the reaction temperature, but it is preferably 1-48 hours and more preferably 1-6 hours at the aforementioned reaction temperature after addition of the reagents.

The acid may be used in an amount of 1 mol or more with respect to compound (1B-1), and a large excess of acid may also be used as the reaction solvent.

Step 2B

This is a step of reacting compound (2B-1) and compound (2B-2) in a solvent in the presence of a condensation agent to produce compound (2C-1).

This step may be carried out with reference to the reaction conditions described in (12b) of Example 12 below and the like.

As compounds represented by general formula (2B-2), there may be used a commercially available compound, or a compound that can be easily produced by a person skilled in the art from a commercially available compound.

The reaction may be carried out under a stream or in an atmosphere of an inert gas such as nitrogen or argon.

The solvent used for the reaction is not particularly restricted so long as it can dissolve the starting materials to some extent and does not interfere with the reaction, and examples include ether solvents such as tetrahydrofuran, 1,2-dimethoxyethane, methyl-tert-butyl ether, cyclopentyl methyl ether, diethyl ether, diisopropyl ether, dibutyl ether, dicyclopentyl ether, 1,2-dimethoxyethane and 1,4-dioxane, amide solvents such as N,N-dimethylformamide, and a mixed solvent thereof.

The condensation agent for this step will differ depending on the starting materials and the solvent used and is not particularly restricted, and examples include water-soluble carbodiimide (1-ethyl-3-(3-dimethylaminopropyl)carbodiimide hydrochloride), 1-hydroxybenzotriazole, and a mixture thereof.

The reaction temperature will generally differ depending on the starting materials, solvent and other reagents used in the reaction, but it is preferably 0° C.-40° C.

The reaction time will also differ in most cases depending on the starting materials, the solvent and the other reagents used in the reaction, and on the reaction temperature, but it is preferably 1-48 hours at the aforementioned temperature after addition of the reagents.

Compound (2B-2) may be used at 1-5 molar equivalents and preferably 1-1.5 molar equivalents with respect to compound (2B-1).

The condensation agent may be used at 1-10 molar equivalents with respect to compound (2B-1).

Step 2C

This is a step of reducing compound (2C-1) in a solvent in the presence of a reducing agent to produce compound (2D-1).

The step may be carried out with reference to the reaction conditions described in (12c) of Example 12 below and the like.

The reaction may be carried out under a stream or in an atmosphere of an inert gas such as nitrogen or argon.

The solvent used for the reaction is not particularly restricted so long as it can dissolve the starting materials to some extent and does not interfere with the reaction, and examples include ether solvents such as tetrahydrofuran, 1,2-dimethoxyethane, methyl-tert-butyl ether, cyclopentyl methyl ether, diethyl ether, diisopropyl ether, dibutyl ether, dicyclopentyl ether, 1,2-dimethoxyethane and 1,4-dioxane, among which tetrahydrofuran is preferred.

The reducing agent for this step will differ depending on the starting materials and the solvent used and is not particularly restricted, and examples include borane and a solution of borane in tetrahydrofuran.

The reaction temperature will generally differ depending on the starting materials, solvent and other reagents used in the reaction, but it is preferably from 0° C. to the reflux temperature of the solvent (as the reactor internal temperature).

The reaction time will also differ in most cases depending on the starting materials, the solvent and the other reagents used in the reaction, and on the reaction temperature, but it is preferably 1-24 hours at the aforementioned temperature after addition of the reagents.

The reducing agent may be used at 1-10 molar equivalents and preferably 2-5 molar equivalents with respect to compound (2C-1).

The product of step 2C may be used as starting material for the subsequent step without any special purification, with only a procedure of simple treatment of the reaction solution and distilling off the solvent, similar to (12c) in Example 12 described below.

Step 2D

This is a step in which compound (2D-1) and compound (1D-2) are reacted to obtain compound (2E-1).

The reaction conditions for this step may be the same conditions by the same procedure as in step 1D of Production Scheme 1.

Upon completion of the reaction in each step of the processes described above, the target compound of each step may be recovered from the reaction mixture by an ordinary method.

[Reaction Treatment Method]

When the reaction mixture is a liquid, for example, the reaction mixture is returned to room temperature or cooled on ice as desired, and neutralized with an appropriate acid, alkali, oxidizing agent or reducing agent, followed by addition of water and an organic solvent that is immiscible therewith and does not react with the target compound, such as ethyl acetate. After thoroughly shaking the mixture, it is allowed to stand for separation and the layer of the resulting bilayer that contains the target compound is separated. Next, a solvent that is immiscible with the obtained layer and does not react with the target compound is added, and then the layer containing the target compound is washed and separated. When the layer is an organic layer, it may be dried using a desiccant such as anhydrous magnesium sulfate or anhydrous sodium sulfate, and the solvent distilled off to obtain the target compound. When the layer is an aqueous layer, it may be electrically desalted and then freeze-dried to obtain the target compound.

When the entire reaction mixture is a liquid, it may be possible to recover the target compound simply by distilling off the components other than the target compound (for example, solvent, reagents, etc.) at ordinary pressure or under reduced pressure.

When the target compound precipitates alone as a solid, or when the entire reaction mixture is a liquid and the target compound precipitates alone as a solid during the collecting process, the target compound may be first collected by a filtration method, the collected target compound washed with a suitable organic or inorganic solvent and drying carried out as suitable to obtain the target compound.

On the other hand, when the reagents or catalyst are the only solids present, or when the reagents or catalyst alone precipitate as solid during treatment of the reaction mixture, with the target compound remaining dissolved in solution, the reagents or catalyst may be first removed by a filtration method, the removed reagents or catalyst washed with a suitable organic or inorganic solvent, and the obtained wash combined with the mother liquor to obtain a liquid mixture, which may then be treated in the same manner as in the case that the entire reaction mixture is a liquid, in order to obtain the target compound.

The reaction mixture may be used directly for subsequent steps without isolation of the target compound in cases where components other than the target compound in the reaction mixture will not inhibit reaction in the subsequent steps.

[Purifying Process]

Purity of the target compound collected by the above methods can be increased by appropriately carrying out recrystallization, various chromatography methods, or distillation.

When the collected target compound is a solid, purity of the target compound can usually be improved by recrystallization. For recrystallization there may be used a simple solvent or a multiple solvent mixture that does not react with the target compound. Specifically, the target compound may first be dissolved at room temperature or with heating in the simple solvent or solvent mixture that does not react with the target compound. The obtained mixture may then be cooled with ice water or the like or allowed to stand at room temperature to cause precipitation of the target compound from the mixture.

When the collected target compound is a solid or liquid, purity of the target compound can be improved by various chromatography methods. In most cases a weakly acidic silica gel such as silica gel 60 (70-230 mesh or 340-400 mesh) by Merck, Ltd. or BW-300 (300 mesh) by Fuji Silysia Chemical, Ltd. may be used. If the target compound is basic, there may be used propylamine-coated silica gel (200-350 mesh) by Fuji Silysia Chemical, Ltd., or the like. If the target compound is dipolar or requires elution with a highly polar solvent such as methanol, there may be used NAM-200H or NAM-300H by Nagara Science Co., Ltd. Using these silica gels, the target compound may be eluted in a simple solvent or solvent mixture that does not react with the target compound and the solvent distilled off to obtain the target compound with enhanced purity.

When the collected target compound is a liquid, purity of the target compound can also be improved by distillation. The temperature and degree of reduced pressure may be adjusted as appropriate depending on the target compound, to obtain the target compound by an ordinary distillation method.

When a compound of the invention is obtained in free form, it may be converted to an acceptable salt of the compound by an ordinary method.

Conversely, when a compound of the invention is obtained as a salt, it may be converted to the free form of the compound by an ordinary method.

Various isomers (for example, geometric isomers, optical isomers, rotational isomers, stereoisomers, tautomers and the like) obtained for compounds of the invention may be purified and isolated using ordinary separation means such as, for example, recrystallization, a diastereomer salt method, enzymatic resolution or various chromatography methods (for example, thin-layer chromatography, column chromatography, gas chromatography, etc.).

[Formulation]

When a compound of the invention is to be used as a drug, the compound of the invention will usually be used after mixture and formulation with appropriate additives. However, this does not negate the use of the compounds of the invention in bulk forms as drugs.

As additives there may be mentioned excipients, binders, lubricants, disintegrators, coloring agents, taste correctives, emulsifiers, surfactants, dissolving aids, suspending agents, isotonizing agents, buffering agents, antiseptic agents, antioxidants, stabilizers, absorption accelerators and the like which are commonly used in drugs, and these may also be used in appropriate combinations as desired.

As examples of excipients there may be mentioned lactose, white soft sugar, glucose, corn starch, mannitol, sorbitol, starch, pregelatinized starch, dextrin, crystalline cellulose, light silicic anhydride, aluminum silicate, calcium silicate, magnesium aluminometasilicate, calcium hydrogenphosphate and the like.

As examples of binders there may be mentioned polyvinyl alcohol, methylcellulose, ethylcellulose, gum arabic, tragacanth, gelatin, shellac, hydroxypropylmethylcellulose, hydroxypropylcellulose, carboxymethylcellulose sodium, polyvinylpyrrolidone, macrogol and the like.

As examples of lubricants there may be mentioned magnesium stearate, calcium stearate, sodium stearyl fumarate, talc, polyethylene glycol, colloidal silica and the like.

As examples of disintegrators there may be mentioned crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium and the like.

As coloring agents there may be mentioned those approved for addition to pharmaceuticals, such as iron sesquioxide, yellow iron sesquioxide, calamine, caramel, β-carotene, titanium oxide, talc, riboflavin sodium phosphate, yellow aluminum lake and the like.

As taste correctives there may be mentioned cocoa powder, menthol, aromatic powders, peppermint oil, camphor, cinnamon powder and the like.

As emulsifying agents or surfactants there may be mentioned stearyl triethanolamine, sodium lauryl sulfate, lauryl aminopropionic acid, lecithin, glycerin monostearate, sucrose fatty acid esters, glycerin fatty acid esters and the like.

As dissolving aids there may be mentioned polyethylene glycol, propylene glycol, benzyl benzoate, ethanol, cholesterol, triethanolamine, sodium carbonate, sodium citrate, polysorbate 80, nicotinamide and the like.

As suspending agents there may be mentioned the aforementioned surfactants, as well as hydrophilic polymers such as polyvinyl alcohol, polyvinylpyrrolidone, methylcellulose, hydroxymethylcellulose, hydroxyethylcellulose and hydroxypropylcellulose.

As isotonizing agents there may be mentioned glucose, sodium chloride, mannitol, sorbitol and the like.

As buffering agents there may be mentioned phosphate, acetate, carbonate and citrate buffering solutions.

As antiseptic agents there may be mentioned methylparaben, propylparaben, chlorobutanol, benzyl alcohol, phenethyl alcohol, dehydroacetic acid, sorbic acid and the like.

As antioxidants there may be mentioned sulfite, ascorbic acid, α-tocopherol and the like.

As stabilizers there may be mentioned those commonly used in drugs.

As absorption accelerators there may also be mentioned those commonly used in drugs.

As formulations there may be mentioned oral forms such as tablets, powders, granules, capsules, syrups, lozenges and inhalants; external preparations such as suppositories, ointments, eye salves, tapes, eye drops, nose drops, ear drops, poultices, lotions, and the like; and injections.

The aforementioned oral forms may be formulated with appropriate combinations of the additives mentioned above. Their surfaces may also be coated if necessary.

The aforementioned external preparations may be formulated with appropriate combinations of the additives mentioned above, and especially excipients, binders, taste correctives, emulsifiers, surfactants, dissolving aids, suspending agents, isotonizing agents, antiseptic agents, antioxidants, stabilizers and absorption accelerators.

Injections may also be formulated with appropriate combinations of the additives mentioned above, and especially emulsifiers, surfactants, dissolving aids, suspending agents, isotonizing agents, buffering agents, antiseptic agents, antioxidants, stabilizers and absorption accelerators.

The dosage of a drug according to the invention will differ depending on the severity of symptoms, patient age, gender and body weight, type of dosage form/salt, patient drug sensitivity and specific nature of the disease, but the dosage per day for adults will generally be 30 μg to 10 g (preferably 0.1 mg to 1 g) for oral administration, 30 μg to 20 g (preferably 100 μg to 10 g) for external application and 30 μg to 1 g (preferably 100 μg to 1 g) for injection, either administered at a single time or divided into several dosages.

These values are the actual administered amounts in the case of oral formulations and injections, and are the amounts actually absorbed by the body in the case of external formulations.

EXAMPLES

The compounds of the invention may be produced by the processes described in the following examples, and the effects of the compounds may be confirmed by the methods described in the following testing examples. However, these specific examples are merely illustrative and not intended to restrict the invention in any way, while various modifications may be implemented such as are within the scope of the invention.

Compounds mentioned with reference to published documents were produced in the manner described in those documents.

The symbols used throughout the present specification stand for the followings.
$^1$H-NMR: Proton nuclear magnetic resonance
δ: Chemical shift
s: singlet
d: doublet
t: triplet
q: quartet
m: multiplet
dd: double doublet
br.s: broad singlet
sept: septet
J: coupling constant
Hz: Hertz
M: mol/L
n-: normal
s-: secondary
tert-: tertiary (tertiary)
N: Normality
$CDCl_3$: deuterio-chloroform
DMSO-$d_6$: deuterio-dimethyl sulfoxide
DMF: N,N-Dimethylformamide
DME: 1,2-Dimethoxyethane
THF: Tetrahydrofuran
DMSO: Dimethyl sulfoxide
NMP: N-Methylpyrrolidinone
WSCD: Water-soluble carbodiimide, 1-ethyl-3-(3-dimethylaminopropyl)carbodiimide hydrochloride [CAS No. 25952-53-8]
4AMS: Molecular sieves 4 A (pore size: 4 angstrom)
Me: Methyl
EGTA: Glycol ether diamine tetraacetic acid (O,O'-bis(2-aminoethyl)ethyleneglycol-N,N,N',N'-tetraacetic acid)
BSA: Bovine serum albumin "Under reduced pressure" means conditions with approximately 1 to 50 mmHg by using a vacuum pump, a water-jet pump etc.

Unless otherwise specified, the "silica gel" in "silica gel column chromatography" mentioned throughout the examples is Silica Gel 60 (70-230 mesh or 340-400 mesh) by Merck, Ltd., FLASH+Cartridge (KP-SIL, pore size: 60 angstrom, particle size: 32-63 μm) by Biotage, or Cartridge (Hi-Flash, pore size: 60 angstrom, particle size: 40 μm) by Yamazen.

Also unless otherwise specified, the "(NH)silica gel" in "(NH)silica gel column chromatography" mentioned throughout the examples is propylamine-coated silica gel (200-350 mesh) by Fuji Silysia Chemical, Ltd., or Cartridge (Hi-Flash Amino, pore size: 60 angstrom, particle size: 40 μm) by Yamazen.

The term "room temperature" refers to a range from about 10° C. to 35° C. The percentage values are weight percentages, unless otherwise specified.

Production Example 1A

Dihydro-2H-pyran-3(4H)-one

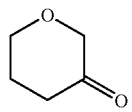

[Chemical Formula 8]

To a mixture of oxalyl chloride (2.28 mL, 26.6 mmol) and dichloromethane (40 mL) was added a mixture of DMSO (3.78 mL, 53.2 mmol) and dichloromethane (20 mL) while stirring at −78° C., and the mixture was stirred at −78° C. for 30 minutes. After then adding to this mixture a mixture of tetrahydropyran-3-ol (synthesized according to the method described in Tetrahedron, 60, 10411-10418, 2004) (1.36 g, 13.3 mmol) and dichloromethane (20 mL) at −78° C., the resulting mixture was stirred at −78° C. for 30 minutes, after which triethylamine (11.1 mL, 79.8 mmol) was added and stirring was continued for 2 hours while slowly raising the temperature to 0° C.

Brine and diethyl ether were added to the mixture, and after sufficient shaking, the organic layer was separated and the organic layer was washed with brine and dried over anhydrous magnesium sulfate. The mixture was then filtered, and the solvent in the filtrate was distilled off under reduced pressure to obtain the title compound (1.62 g, 16.2 mmol).

$^1$H-NMR(CDCl$_3$) δ: 2.07-2.14 (m, 2H), 2.54 (t, J=6.8 Hz, 2H), 3.82-3.88 (m, 2H), 4.03 (s, 2H).

Production Example 1B

2-Cyclopropylethyl methanesulfonate

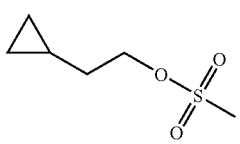

[Chemical Formula 9]

To a mixture of 2-cyclopropylethanol (5.35 g, 62.1 mmol) and dichloromethane (107 mL) were added methanesulfonyl chloride (5.29 mL, 68.3 mmol) and triethylamine (13.1 mL, 93.1 mmol) in that order while stirring on ice, and the resulting mixture was stirred for 1 hour. Water and ethyl acetate were then added to the reaction mixture. After thoroughly shaking the mixture, the organic layer was separated and the organic layer was washed with brine and dried over anhydrous magnesium sulfate. The mixture was then filtered, and the solvent in the filtrate was distilled off under reduced pressure to obtain the title compound (10.3 g, 62.7 mmol).

$^1$H-NMR (CDCl$_3$) δ: 0.10-0.16 (m, 2H), 0.48-0.55 (m, 2H), 0.72-0.83 (m, 1H), 1.65 (q, J=6.8 Hz, 2H), 3.01 (s, 3H), 4.29 (t, J=6.8 Hz, 2H).

Production Example 1C (1)

4-Bromo-3,5-dimethoxybenzamide

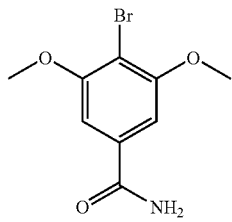

[Chemical Formula 10]

To a mixture of 4-bromo-3,5-dimethoxybenzoic acid (15 g, 57.6 mmol) and THF (200 mL) were added triethylamine (9.63 mL, 69.0 mmol) and ethyl chloroformate (5.79 mL, 60.6 mmol) while stirring on ice, and the resulting mixture was stirred for 20 minutes while cooling on ice. After adding 28% aqueous ammonia to the mixture and stirring at room temperature for 2 hours, ethyl acetate was further added. After then thoroughly shaking the mixture, the organic layer was separated and the organic layer was washed with brine and dried over anhydrous magnesium sulfate. The mixture was filtered, and the solvent in the filtrate was distilled off under reduced pressure. The obtained residue (solid) was washed with diethyl ether and collected by filtration to obtain the title compound (11.8 g, 45.4 mmol).

$^1$H-NMR (CDCl$_3$) δ: 3.95 (s, 6H), 7.00 (s, 2H).

Production Example 1C (2)

4-Bromo-3,5-dimethoxybenzonitrile

[Chemical Formula 11]

After adding toluene (20 mL), DMF (5 mL) and thionyl chloride (3.36 mL, 46.1 mmol) to 4-bromo-3,5-dimethoxybenzamide (4 g, 15.4 mmol) in that order, the mixture was stirred at 50° C. for 1 hour. Ice water was added to the mixture at room temperature, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure.

The obtained residue (solid) was washed with diethyl ether/n-heptane (1/1) to obtain the title compound (2.08 g, 8.59 mmol).

$^1$H-NMR (CDCl$_3$) δ: 3.93 (s, 6H), 6.82 (s, 2H).

Production Example 1C (3)

(4-Cyano-2,6-dimethoxyphenyl)boronic acid

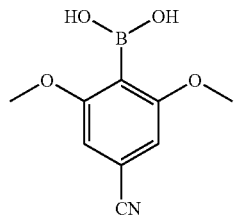

[Chemical Formula 12]

To a mixture of 4-bromo-3,5-dimethoxybenzonitrile (2 g, 8.26 mmol) and THF (60 mL) was added n-butyllithium (1.58 M solution in n-hexane: 5.48 mL, 8.68 mmol) while stirring at −100° C., and stirring was continued at −100° C. for 30 minutes. After then adding trimethyl borate (1.84 mL, 16.5 mmol), stirring was continued for 4 hours while raising the temperature to −20° C. A saturated aqueous solution of ammonium chloride and 1N hydrochloric acid were then added to the reaction mixture, and ethyl acetate was added.

After thoroughly shaking the mixture, the organic layer was separated and the organic layer was washed with brine and dried over anhydrous magnesium sulfate. The mixture was filtered, and then the solvent in the filtrate was distilled off under reduced pressure. The obtained residue (solid) was washed with n-heptane to obtain the title compound (1.43 g, 6.91 mmol).

$^1$H-NMR (CDCl$_3$) δ: 3.96 (s, 6H), 6.89 (s, 2H), 7.01 (s, 2H).

Production Example 2C (1)

Ethyl 4-amino-3-methoxybenzoate

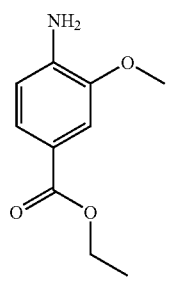

[Chemical Formula 13]

To a mixture of 4-amino-3-methoxybenzoic acid (15 g, 89.7 mmol) and ethanol (170 mL) was added concentrated sulfuric acid (5 mL), and the mixture was heated to reflux for 7 hours. The reaction mixture was then returned to room temperature. The solvent in the filtrate was distilled off under reduced pressure. Water, a saturated aqueous solution of sodium hydrogencarbonate and ethyl acetate were added to the residue After thoroughly shaking the mixture, the organic layer was separated and the organic layer was washed with brine and dried over anhydrous magnesium sulfate. The mixture was then filtered, and the solvent in the filtrate was distilled off under reduced pressure to obtain the title compound (17.8 g, 91.2 mmol).

$^1$H-NMR (CDCl$_3$) δ: 1.37 (t, J=6.8 Hz, 3H), 3.90 (s, 3H), 4.32 (q, J=6.8 Hz, 2H) 6.66 (d, J=8.0 Hz, 1H), 7.45 (d, J=1.6 Hz, 1H), 7.54 (dd, T=1.6, 8.0 Hz, 1H).

Production Example 2C (2)

Ethyl 4-amino-3-chloro-5-methoxybenzoate

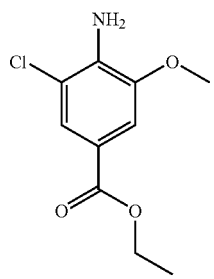

[Chemical Formula 14]

After adding acetonitrile (170 mL) and N-chlorosuccinimide (13.4 g, 100 mmol) to ethyl 4-amino-3-methoxybenzoate (17.8 g, 91.2 mmol) in that order, the mixture was stirred at 60° C. for 2 hours. The mixture was returned to room temperature, and the solvent in the mixture was distilled off under reduced pressure. The residue was purified by silica gel column chromatography (mixture of n-heptane and ethyl acetate: n-heptane/ethyl acetate=8/1 then 4/1) to obtain the title compound (15.8 g, 68.8 mmol).

$^1$H-NMR (CDCl$_3$) δ: 1.37 (t, J=6.8 Hz, 3H), 3.91 (s, 3H), 4.32 (q, J=6.8 Hz, 2H), 4.58 (br.s, 2H), 7.36 (d, J=1.8 Hz, 1H), 7.65 (d, J=1.8 Hz, 1H).

Production Example 2C (3)

Ethyl 3-chloro-4-iodo-5-methoxybenzoate

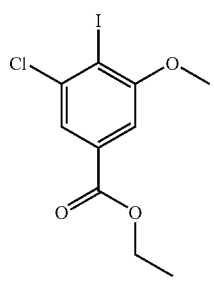

[Chemical Formula 15]

To ethyl 4-amino-3-chloro-5-methoxybenzoate (15.8 g, 68.8 mmol) were added acetonitrile (40 mL) and diiodomethane (22.2 mL, 275 mmol) in that order, and then the mixture was stirred at 70° C. and isoamyl nitrite (13.9 mL, 103 mmol) was added dropwise over a period of 10 minutes. The mixture was then stirred at 70° C. for 40 minutes. After returning the mixture to room temperature, the solvent in the mixture was distilled off under reduced pressure and the residue was purified by silica gel column chromatography (mixture of n-heptane and ethyl acetate: n-heptane/ethyl acetate=8/1 then 5/1) to obtain the title compound (15.6 g, 45.8 mmol).

$^1$H-NMR (CDCl$_3$) δ: 1.40 (t, J=7.2 Hz, 3H), 3.95 (s, 3H), 4.38 (q, J=7.2 Hz, 2H), 7.30 (d, J=1.6 Hz, 1H), 7.73 (d, J=1.6 Hz, 1H).

Production Example 2C (4)

(3-Chloro-4-iodo-5-methoxyphenyl)methanol

[Chemical Formula 16]

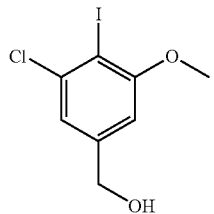

To a mixture of ethyl 3-chloro-4-iodo-5-methoxybenzoate (15.6 g, 45.8 mmol) and toluene (150 mL) was added diisobutylaluminum hydride (1.01 M solution in toluene: 95.2 mL, 96.2 mmol) while stirring at −78° C., and stirring was continued for 3 hours while raising the temperature to −30° C. After then adding a solution of Rochelle salt (sodium potassium (+)-tartrate tetrahydrate) (77.6 g, 275 mmol) in water (400 mL) to the mixture, stirring was continued for 5 hours at room temperature and ethyl acetate was added. After thoroughly shaking the mixture, the organic layer was separated and the organic layer was washed with brine and dried over anhydrous magnesium sulfate. The mixture was then filtered, and the solvent in the filtrate was distilled off under reduced pressure to obtain the title compound (13.7 g, 45.8 mmol).

$^1$H-NMR (CDCl$_3$) δ: 3.90 (s, 3H), 4.66 (s, 2H), 6.72 (d, J=1.2 Hz, 1H), 7.09 (br., 1H).

Production Example 2C (5)

1-Chloro-2-iodo-3-methoxy-5-(methoxymethyl)benzene

[Chemical Formula 17]

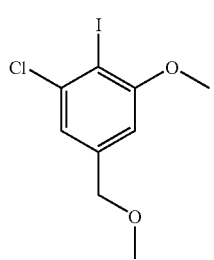

To a mixture of (3-chloro-4-iodo-5-methoxyphenyl)methanol (13.7 g, 45.9 mmol) and NMP (90 mL) were added sodium hydride (60% dispersion in oil: 2.02 g, 50.5 mmol) and iodomethane (3.14 mL, 50.4 mmol), and the mixture was stirred at room temperature for 4 hours. Water and diethyl ether were added to the mixture. After thoroughly shaking the mixture, the organic layer was separated and the organic layer was washed with brine and dried over anhydrous magnesium sulfate. The mixture was filtered, and then the solvent in the filtrate was distilled off under reduced pressure.

The residue was purified by silica gel column chromatography (mixture of n-heptane and ethyl acetate: n-heptane/ethyl acetate=8/1 then 4/1) to obtain the title compound (13.2 g, 42.2 mmol).

$^1$H-NMR (CDCl$_3$) δ: 3.40 (s, 3H), 3.90 (s, 3H), 4.40 (s, 2H), 6.69 (s, 1H), 7.07 (s, 1H).

Production Example 2C (6)

[2-Chloro-6-methoxy-4-(methoxymethyl)phenyl]boronic acid

[Chemical Formula 18]

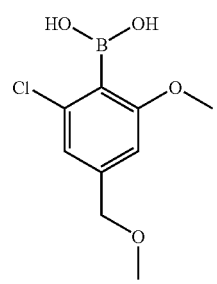

To a mixture of 1-chloro-2-iodo-3-methoxy-5-(methoxymethyl)benzene (4.72 g, 15.1 mmol) and THF (150 mL) was added n-butyllithium (1.58 M solution in n-hexane: 10.5 mL, 16.6 mmol) while stirring at −100° C., and stirring was continued for 30 minutes at −100° C. to −85° C. After then adding trimethyl borate (4.21 mL, 37.8 mmol), stirring was continued for 4 hours while slowly raising the temperature to −20° C. A saturated aqueous solution of ammonium chloride and 1N hydrochloric acid were then added to the reaction mixture, and ethyl acetate was further added.

After thoroughly shaking the mixture, the organic layer was separated and the organic layer was washed with brine and dried over anhydrous magnesium sulfate. The mixture was filtered, and then the solvent in the filtrate was distilled off under reduced pressure. The obtained residue (solid) was washed with n-heptane to obtain the title compound (2.65 g, 11.5 mmol).

$^1$H-NMR (CDCl$_3$) δ: 3.42 (s, 3H), 3.92 (s, 3H), 4.44 (s, 2H), 6.23 (s, 2H), 6.86 (s, 1H), 7.00 (br.s, 1H).

Example 1

N-Butyl-3-[2,6-dimethoxy-4-(methoxymethyl)phenyl]-6-methoxy-N-(tetrahydro-2H-pyran-4-yl)pyrazolo[5,1-b][1,3]thiazole-7-amine

[Chemical Formula 19]

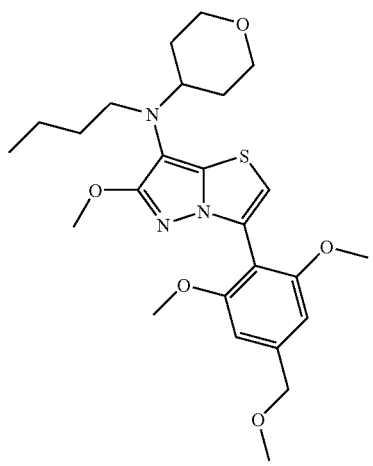

(1a)
2,6-Dimethoxy-4-(methoxymethyl)benzaldehyde

[Chemical Formula 20]

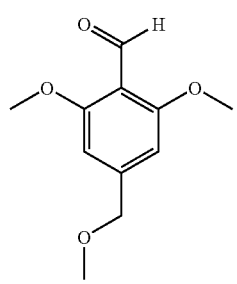

To a mixture of 1,3-dimethoxy-5-methoxymethyl-2-bromobenzene (Production Example 8X of WO 04/037822) (33.8 g, 129 mmol) and tetrahydrofuran (338 mL) was added n-butyllithium (2.77 M solution in n-hexane: 55.9 mL, 155 mmol) at −78° C. After stirring the mixture at −78° C. for 30 minutes, DMF (11 mL, 142 mmol) was added and stirring was continued for 2 hours while heating to room temperature. A saturated aqueous solution of ammonium chloride and ethyl acetate were added to the reaction mixture.

After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=2/1 then 1/1) to obtain the title compound (16.3 g, 77.5 mmol).

$^1$H-NMR (CDCl$_3$) δ: 3.45 (s, 3H), 3.91 (s, 6H), 4.46 (s, 2H), 6.56 (s, 2H), 10.48 (s, 1H).

(1b)
1-[2,6-Dimethoxy-4-(methoxymethyl)phenyl]ethanone

[Chemical Formula 21]

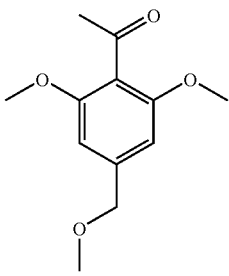

To a mixture of 2,6-dimethoxy-4-(methoxymethyl)benzaldehyde (16.3 g, 77.5 mmol) and THF (200 mL) was added methylmagnesium bromide (0.99 M solution in n-hexane: 95.9 mL, 93 mmol) at 0° C., and the mixture was stirred for 30 minutes. A saturated aqueous solution of ammonium chloride and ethyl acetate were added to the reaction mixture at 0° C.

After thoroughly shaking the mixture, the organic layer was separated and the organic layer was washed with brine and dried over anhydrous magnesium sulfate. The mixture was filtered, and then the solvent in the filtrate was distilled off under reduced pressure. Dichloromethane-acetonitrile (9:1,160 mL), 4 ÅMS (38 g), 4-methylmorpholine-4-oxide (14.6 g, 121 mmol) and tetrapropylammonium perruthenate (1.41 g, 4.02 mmol) were added to the obtained residue in that order and the mixture was stirred at room temperature for 13 hours. Ethyl acetate was added to the mixture, and silica gel column chromatography was performed for suction filtration. The solvent in the obtained filtrate was distilled off under reduced pressure. The residue was purified by silica gel column chromatography (mixture of n-heptane and ethyl acetate: n-heptane/ethyl acetate=1/1 then 1/2) to obtain the title compound (16.8 g, 75.1 mmol).

$^1$H-NMR (CDCl$_3$) δ: 2.47 (s, 3H), 3.41 (s, 3H), 3.81 (s, 6H), 4.44 (s, 2H), 6.54 (s, 2H).

(1c) Ethyl 3-{[4-(2,6-dimethoxy-4-(methoxymethyl)phenyl]-2-thioxo-1,3-thiazole-3(2H)-yl]-amino}-3-oxopropanoate

[Chemical Formula 22]

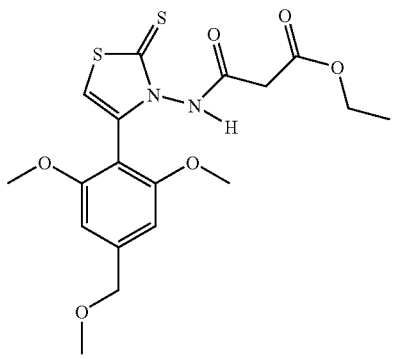

After adding tetrahydrofuran (140 mL) and triethylamine (56.1 mL, 403 mmol) to 1-[2,6-dimethoxy-4-(methoxymethyl)phenyl]ethanone (22.7 g, 102 mmol), tert-butyldimethylsilyl trifluoromethanesulfonic acid (33.1 mL, 145 mmol) was slowly added dropwise at 0° C. and the mixture was stirred for 30 minutes. To this mixture was added N-bromosuccinimide (18.8 g, 107 mmol) at 0° C., and stirring was continued for 1.5 hours. A saturated aqueous solution of sodium hydrogencarbonate was added to the mixture, and ethyl acetate was added.

After thoroughly shaking the mixture, the organic layer was separated and the organic layer was washed with brine and dried over anhydrous magnesium sulfate. The mixture was filtered, and then the solvent in the filtrate was distilled off under reduced pressure.

Tetrabutylammonium fluoride (1.0 M solution in THF: 91.4 mL, 91.4 mmol) was added to a mixture of the obtained residue and tetrahydrofuran (140 mL) at 0° C., and the mixture was stirred for 30 minutes. A saturated aqueous solution of ammonium chloride and ethyl acetate were added to the reaction mixture at 0° C.

After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=3/1 then 2/1).

To a mixture of the obtained residue and water-ethanol (2:1,275 mL) was added potassium hydrazinecarbodithioate (Heterocycles, vol. 23, No. 12, 1985, 3099-3106) at 4° C., and the mixture was stirred for 20 hours. The mixture was suction filtered with a glass filter, and the residue was washed with water and dried under reduced pressure. To a mixture of the obtained residue and dichloromethane (400 mL) was added dropwise ethylmalonyl chloride (8.86 mL, 66.6 mmol) at 0° C., and the mixture was stirred at room temperature for 30 minutes. The solvent in the filtrate was distilled off under reduced pressure. The residue was purified by silica gel column chromatography (mixture of n-heptane and ethyl acetate: n-heptane/ethyl acetate=1/1 then 1/3) to obtain the title compound (11.7 g, 27.6 mmol).

$^1$H-NMR (CDCl$_3$) δ: 1.24 (t, J=7.2 Hz, 3H), 3.33 (br.s, 2H), 3.44 (s, 3H), 3.82 (s, 6H), 4.14 (q, J=7.2 Hz, 2H), 4.45 (s, 2H), 4.49 (s, 1H), 6.57 (s, 2H), 9.67 (s, 1H).

(1d) Ethyl 3-[2,6-dimethoxy-4-(methoxymethyl)phenyl]-6-hydroxypyrazolo[5,1-b][1,3]thiazole-7-carboxylate

[Chemical Formula 23]

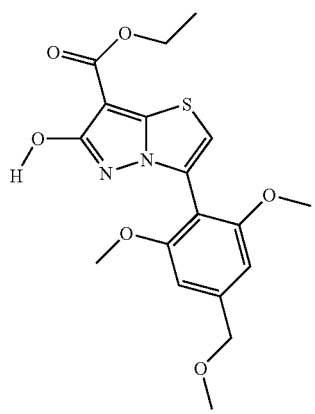

Acetone (235 mL) was added to ethyl 3-{[4-(2,6-dimethoxy-4-(methoxymethyl)phenyl]-2-thioxo-1,3-thiazole-3(2H)-yl]-amino}-3-oxopropanoate (11.7 g, 27.6 mmol), and then iodomethane (17.1 mL, 276 mmol) was added dropwise at room temperature and the mixture was stirred for 23 hours. The solvent in the filtrate was distilled off under reduced pressure. To the obtained residue were added tert-butanol (235 mL) and potassium tert-butoxide in that order, and the mixture was stirred at room temperature for 3.5 hours. Water was added to the mixture while cooling on ice, and then aqueous 2N hydrochloric acid was added until the pH of the mixture reached approximately 4. The precipitated solid was collected by filtration, and the resulting residue was washed with water and dried under reduced pressure to obtain the title compound (6.3 g, 16 mmol).

$^1$H-NMR (CDCl$_3$) δ: 1.41 (t, J=6.8 Hz, 3H), 3.44 (s, 3H), 3.75 (s, 6H), 4.39 (q, J=6.8 Hz, 2H), 4.49 (s, 2H), 6.62 (s, 2H), 6.72 (s, 1H).

(1e) Ethyl 3-[2,6-dimethoxy-4-(methoxymethyl)phenyl]-6-methoxypyrazolo[5,1-b][1,3]thiazole-7-carboxylate

[Chemical Formula 24]

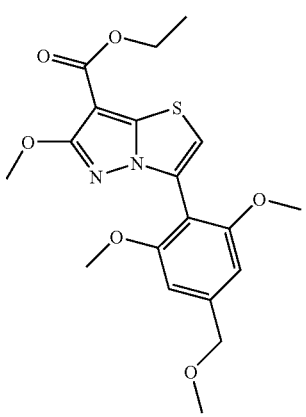

After adding DMF (164 mL), cesium carbonate (26 g, 80.1 mmol) and iodomethane (4.99 mL, 80.1 mmol) in that order to ethyl 3-[2,6-dimethoxy-4-(methoxymethyl)phenyl]-6-hydroxypyrazolo[5,1-b][1,3]thiazole-7-carboxylate (6.3 g, 16 mmol), the mixture was stirred at 70° C. for 15 hours.

Water and ethyl acetate were then added to the reaction mixture while cooling on ice. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=1/2) to obtain the title compound (2.8 g, 6.89 mmol).

$^1$H-NMR (CDCl$_3$) δ: 1.38 (t, J=7.2 Hz, 3H), 3.47 (s, 3H), 3.77 (s, 6H), 3.96 (s, 3H), 4.33 (q, J=7.2 Hz, 2H), 4.51 (s, 2H), 6.65 (s, 2H), 6.71 (s, 1H).

(1f) 3-[2,6-Dimethoxy-4-(methoxymethyl)phenyl]-6-methoxypyrazolo[5,1-b][1,3]thiazole-7-carboxylic acid

[Chemical Formula 25]

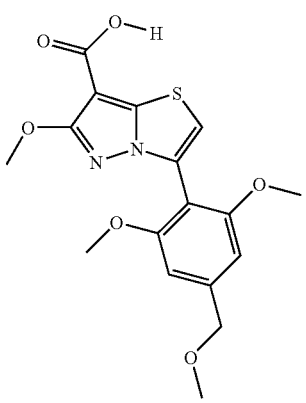

After adding ethanol (124 mL) and aqueous 5N sodium hydroxide (11 mL, 55 mmol) in that order to ethyl 3-[2,6-dimethoxy-4-(methoxymethyl)phenyl]-6-methoxypyrazolo[5,1-b][1,3]thiazole-7-carboxylate (2.8 g, 6.89 mmol), the mixture was heated to reflux for 2 hours. Aqueous 5N hydrochloric acid (11 mL) was then added to the mixture while cooling on ice, and the solvent in the mixture was distilled off under reduced pressure. Water was added to the residue, and the precipitated solid was collected by filtration, washed with water and dried under reduced pressure to obtain the title compound (2.52 g, 6.66 mmol).

$^1$H-NMR (DMSO-$d_6$) δ: 3.38 (s, 3H), 3.72 (s, 6H), 3.79 (s, 3H), 4.48 (s, 2H), 6.76 (s, 2H), 7.16 (s, 1H).

(1g) 3-[2,6-Dimethoxy-4-(methoxymethyl)phenyl]-6-methoxypyrazolo[5,1-b][1,3]thiazole

[Chemical Formula 26]

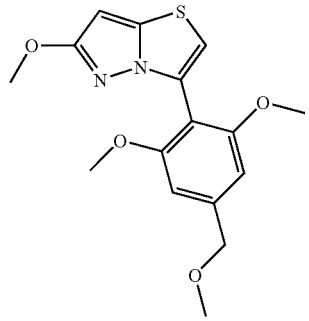

After adding an aqueous solution of polyphosphoric acid (2.6 wt %: 214 mL) to 3-[2,6-dimethoxy-4-(methoxymethyl)phenyl]-6-methoxypyrazolo[5,1-b][1,3]thiazole-7-carboxylic acid (2.52 g, 6.66 mmol), the mixture was heated at 120° C. for 3.5 hours. Water and ethyl acetate were then added to the reaction mixture at room temperature.

After thoroughly shaking the mixture, the organic layer was separated and dried over anhydrous magnesium sulfate. The mixture was filtered, and then the solvent in the filtrate was distilled off under reduced pressure. The residue was purified by (NH)silica gel column chromatography (ethyl acetate) to obtain the title compound (2.17 g, 6.47 mmol).

$^1$H-NMR (CDCl$_3$) δ: 3.46 (s, 3H), 3.77 (s, 6H), 3.89 (s, 3H), 4.50 (s, 2H), 5.84 (s, 1H), 6.40 (s, 1H), 6.63 (s, 2H).

(1h) 3-[2,6-Dimethoxy-4-(methoxymethyl)phenyl]-6-methoxy-7-nitrosopyrazolo[5,1-b][1,3]thiazole

[Chemical Formula 27]

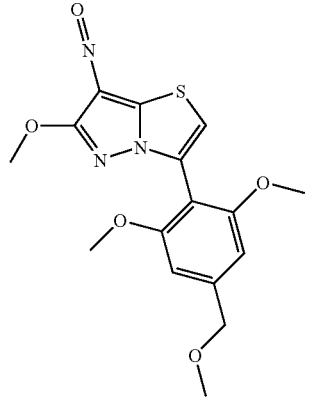

A mixture of water and 5N hydrochloric acid (1:4, 70 mL) was added to 3-[2,6-dimethoxy-4-(methoxymethyl)phenyl]-6-methoxypyrazolo[5,1-b][1,3]thiazole (2.17 g, 6.47 mmol), and then sodium nitrite (1.06 g, 15.3 mmol) was added at 0° C. and the mixture was stirred for 1 hour. Aqueous 5N sodium hydroxide and ethyl acetate were added to the mixture at room temperature. After thoroughly shaking the mixture, the organic layer was separated and dried over anhydrous magnesium sulfate. The mixture was then filtered, and the solvent in the filtrate was distilled off under reduced pressure to obtain the title compound (2.34 g, 6.44 mmol).

$^1$H-NMR (CDCl$_3$) δ: 3.49 (s, 3H), 3.79 (s, 6H), 4.23 (s, 3H), 4.52 (s, 2H), 6.66 (s, 2H), 6.90 (s, 1H)

(1i) 3-[2,6-Dimethoxy-4-(methoxymethyl)phenyl]-6-methoxypyrazolo[5,1-b][1,3]thiazole-7-amine

[Chemical Formula 28]

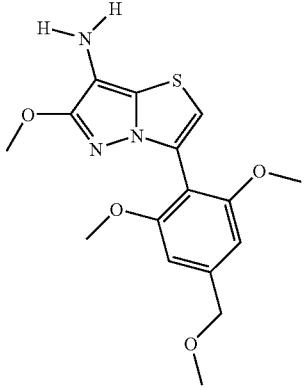

Ethyl acetate (109 mL) and 10% palladium-carbon powder (50% wet: 2.34 g, 2.2 mmol) were added in that order to 3-[2,6-dimethoxy-4-(methoxymethyl)phenyl]-6-methoxy-7-nitrosopyrazolo[5,1-b][1,3]thiazole (2.34 g, 6.44 mmol), and the mixture was stirred for 1 hour under a hydrogen atmosphere. The mixture was filtered with Celite and the solvent in the obtained filtrate was distilled off under reduced pressure. The residue was purified by (NH)silica gel column chromatography (ethyl acetate) to obtain the title compound (1.43 g, 4.09 mmol).

$^1$H-NMR (CDCl$_3$) δ: 2.60 (br.s, 2H), 3.46 (s, 3H), 3.77 (s, 6H), 3.89 (s, 3H), 4.50 (s, 2H), 6.40 (s, 1H), 6.64 (s, 2H).

(1j) tert-Butyl {3-[2,6-dimethoxy-4-(methoxymethyl)phenyl]-6-methoxypyrazolo[5,1-b][1,3]thiazol-7-yl}carbamate

[Chemical Formula 29]

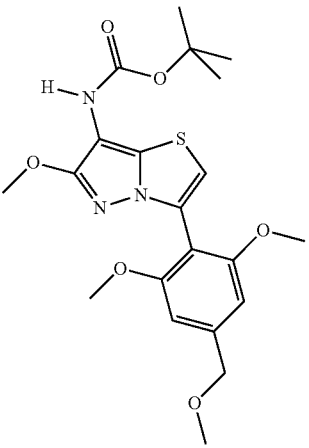

Dichloromethane (50 mL), triethylamine (0.3 mL, 2.15 mmol) and di-tert-butyl dicarbonate (375 mg and 1.72 mmol) were added in that order to 3-[2,6-dimethoxy-4-(methoxymethyl)phenyl]-6-methoxypyrazolo[5,1-b][1,3]thiazole-7-amine (500 mg, 1.43 mmol), and the mixture was stirred at room temperature for 22 hours. The solvent in the mixture was distilled off under reduced pressure. The residue was purified by silica gel column chromatography (mixture of n-heptane and ethyl acetate: n-heptane/ethyl acetate=1/1 then 1/2) to obtain the title compound (511 mg, 1.14 mmol).

$^1$H-NMR (CDCl$_3$) δ: 1.52 (s, 9H), 3.46 (s, 3H), 3.75 (s, 6H), 3.88 (s, 3H), 4.49 (s, 2H), 6.08 (br.s, 1H), 6.43 (s, 1H), 6.63 (s, 2H).

(1k) N-Butyl-3-[2,6-dimethoxy-4-(methoxymethyl)phenyl]-6-methoxy-N-(tetrahydro-2H-pyran-4-yl)pyrazolo[5,1-b][1,3]thiazole-7-amine

[Chemical Formula 30]

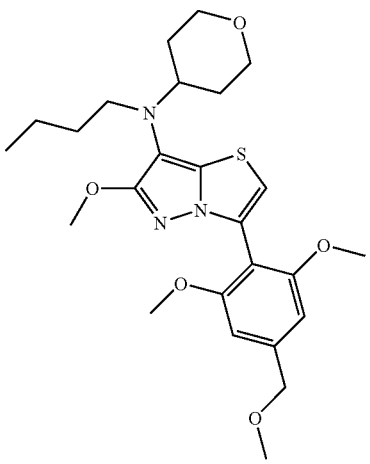

Sodium hydride (60% dispersion in oil: 8.1 mg, 0.203 mmol) was added to a mixture of tert-butyl {3-[2,6-dimethoxy-4-(methoxymethyl)phenyl]-6-methoxypyrazolo[5,1-b][1,3]thiazol-7-yl}carbamate (70 mg, 0.156 mmol) and DMF (6 mL) at room temperature, and the mixture was stirred for 30 minutes. To this mixture was added dropwise 1-iodobutane (0.024 mL, 0.203 mmol) at room temperature, and stirring was continued for 1 hour. Water and ethyl acetate were then added to the reaction mixture while cooling on ice.

After thoroughly shaking the mixture, the organic layer was separated and the organic layer was washed with brine and dried over anhydrous magnesium sulfate. The mixture was filtered, and then the solvent in the filtrate was distilled off under reduced pressure.

Dichloromethane (5 mL) and trifluoroacetic acid (1 mL) were added in that order to the residue, and the mixture was stirred at room temperature for 1 hour. The solvent in the filtrate was distilled off under reduced pressure. After then adding methanol (6 mL), tetrahydro-4H-pyran-4-one (0.03 mL, 0.312 mmol) and acetic acid (1 mL) in that order to the residue at room temperature, α-picolineborane (33.4 mg, 0.312 mmol) was added at 0° C. and the mixture was stirred for 1 hour. To this mixture was added a 5N aqueous solution of sodium hydroxide to approximate neutral pH of the mixture while cooling on ice, and then ethyl acetate was added.

After thoroughly shaking the mixture, the organic layer was separated and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=2/3) to obtain the title compound (61 mg, 0.125 mmol).

$^1$H-NMR (CDCl$_3$) δ: 0.86 (t, J=7.2 Hz, 3H), 1.22-1.42 (m, 4H), 1.56-1.68 (m, 2H), 1.77-1.88 (m, 2H), 2.97 (t, J=7.2 Hz, 2H), 3.00-3.11 (m, 1H), 3.33 (td, J=1.6, 11.6 Hz, 2H), 3.47 (s, 3H), 3.79 (s, 6H), 3.86 (s, 3H), 3.92-4.03 (m, 2H), 4.50 (s, 2H), 6.42 (s, 1H), 6.65 (s, 2H).

Example 2

N-Butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine

[Chemical Formula 31]

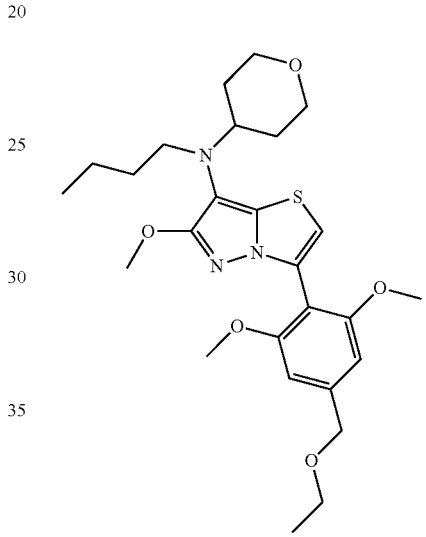

(2a) Ethyl 6-oxo-5,6-dihydropyrazolo[5,1-b][1,3]thiazole-7-carboxylate

[Chemical Formula 32]

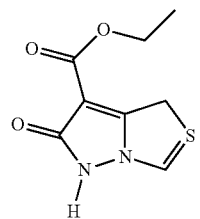

To a mixture of diethyl malonate (100 g, 624 mmol) and DMF (900 mL) were added cesium carbonate (488 g, 1.5 mol) and carbon disulfide (45.3 mL, 749 mmol) while stirring at room temperature, and then stirring was continued at room temperature for 5 minutes. After adding bromoacetaldehydediethylacetal (290 mL, 1.87 mol) dropwise to the mixture at room temperature, sodium iodide (9.34 g, 62.4 mmol) was added and the mixture was stirred at 60° C. for 8 hours. Water and diethyl ether were added to the mixture at room temperature.

After thoroughly shaking the mixture, the organic layer was separated and the organic layer was washed with brine and dried over anhydrous magnesium sulfate. The mixture was filtered, and then the solvent in the filtrate was distilled off under reduced pressure.

To a mixture of the obtained residue and ethanol (900 mL) was added hydrazine hydrate (60.7 mL, 1.25 mol) while stirring in a water bath, and the mixture was stirred at room temperature for 13 hours. The mixture was filtered and the solvent in the filtrate was distilled off under reduced pressure.

To the obtained residue were added 1,4-dioxane (1 L) and 5N hydrochloric acid (200 mL) in that order, and the mixture was stirred at 60° C. for 4 hours. The mixture was returned to room temperature, and the solvent in the mixture was distilled off under reduced pressure. Water was added to the resulting residue, and the mixture was filtered to obtain a filtered residue and filtrate. The residue was washed with water and then dried under reduced pressure to obtain the title compound (42.5 g, 200 mmol).

Ethyl acetate was added to the obtained filtrate. After thoroughly shaking the mixture, the organic layer was separated and the organic layer was washed with brine and dried over anhydrous magnesium sulfate. The mixture was filtered, and then the solvent in the filtrate was distilled off under reduced pressure. Diethyl ether was added to the resulting residue, and the precipitated solid was filtered and dried under reduced pressure to obtain the title compound (2.6 g, 12.3 mmol).

$^1$H-NMR (CDCl$_3$) δ: 1.41 (t, J=7.0 Hz, 3H), 4.40 (q, J=7.0 Hz, 2H), 6.89 (d, J=4.0 Hz, 1H), 7.69 (d, J=4.4 Hz, 1H).

(2b) Ethyl 6-methoxypyrazolo[5,1-b][1,3]thiazole-7-carboxylate

[Chemical Formula 33]

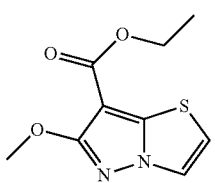

To a mixture of ethyl 6-oxo-5,6-dihydropyrazolo[5,1-b][1,3]thiazole-7-carboxylate (41.3 g, 195 mmol) and DMF (624 mL) were added cesium carbonate (127 g, 389 mmol) and iodomethane (24.2 mL, 389 mmol) while stirring at room temperature. The mixture was stirred at room temperature for 1 hour, and then water and a mixed solvent of ethyl acetate/diethyl ether (1/1) were added.

After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=9/1 then 1/2.3) to obtain the title compound (30.7 g, 136 mmol).

$^1$H-NMR (CDCl$_3$) δ: 1.39 (t, J=7.0 Hz, 3H), 4.08 (s, 3H), 4.35 (q, J=7.0 Hz, 2H), 6.87 (d, J=4.4 Hz, 1H), 7.66 (d, J=4.4 Hz, 1H).

(2c) 6-Methoxypyrazolo[5,1-b][1,3]thiazole

[Chemical Formula 34]

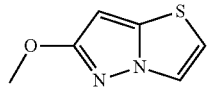

To a mixture of ethyl 6-methoxypyrazolo[5,1-b][1,3]thiazole-7-carboxylate (30.7 g, 136 mmol) and ethanol (407 mL) was added aqueous 5N sodium hydroxide (136 mL) while stirring at room temperature, and the mixture was stirred at 80° C. for 2 hours. A suitable amount of 5N hydrochloric acid was then added while stirring on ice to approximate neutral pH of the mixture. Ethanol in the mixture was distilled off under reduced pressure. The precipitated solid in the mixture was collected by filtration and washed with water.

To the obtained residue were added 1,4-dioxane (400 mL) and concentrated hydrochloric acid (200 mL) in that order, and the mixture was stirred at 60° C. for 1.5 hours. 1,4-Dioxane in the mixture was distilled off under reduced pressure. A suitable amount of sodium hydroxide was added to a weakly acidic pH of the mixture while stirring on ice, and then ethyl acetate was added.

After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=1/0 then 2.3/1) to obtain the title compound (15.8 g, 103 mmol).

$^1$H-NMR (CDCl$_3$) δ: 3.95 (s, 3H), 5.81 (d, J=0.8 Hz, 1H), 6.60 (d, J=4.0 Hz, 1H), 7.58 (dd, J=0.8, 4.4 Hz, 1H).

(2d) tert-Butyl (6-methoxypyrazolo[5,1-b][1,3]thiazol-7-yl)carbamate

[Chemical Formula 35]

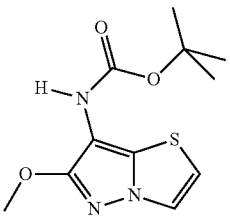

To a mixture of 6-methoxypyrazolo[5,1-b][1,3]thiazole (15.8 g, 103 mmol) and 5N hydrochloric acid (350 mL) was added a mixture of sodium nitrite (10.6 g, 154 mmol) and water (115 mL) while stirring on ice. After stirring the mixture at room temperature for 0.5 hour, aqueous 5N sodium hydroxide was added in an appropriate amount for approximate neutral pH of the mixture, while stirring on ice. The precipitate in the mixture was collected by filtration and washed with water.

Ethanol (200 mL), THF (300 mL) and 10% palladium-carbon (50% wet: 16 g) were added in that order to the obtained residue, and the mixture was stirred at room temperature for 5 hours at an atmospheric pressure under a hydrogen atmosphere. The mixture was filtered with Celite and the solvent in the obtained filtrate was distilled off under reduced pressure.

To a mixture of the obtained residue and dichloromethane (425 mL) were added di-tert-butyl dicarbonate (24.1 g, 111 mmol) and triethylamine (17.8 mL, 128 mmol) while stirring at room temperature, and the mixture was stirred at room temperature for 11 hours. The solvent in the mixture was distilled off under reduced pressure, and then the residue was purified by silica gel column chromatography (mixture of n-heptane and ethyl acetate: n-heptane/ethyl acetate=2/1) to obtain the title compound (16.5 g, 61.4 mmol).

$^1$H-NMR (CDCl$_3$) δ: 1.51 (s, 9H), 3.98 (s, 3H), 6.12 (br.s, 1H), 6.54 (d, J=4.0 Hz, 1H), 7.48 (d, J=4.4 Hz, 1H).

(2d-2) Alternative synthesis method of tert-butyl (6-methoxypyrazolo[5,1-b][1,3]thiazol-7-yl)carbamate To a mixture of 6-methoxypyrazolo[5,1-b]thiazole-7-carboxylic acid (300 mg, 1.51 mmol) and 1,4-dioxane (4 mL) were added triethylamine (0.215 mL, 1.54 mmol) and diphenylphosphoryl azide (0.325 mL, 1.51 mmol) while stirring at room temperature, and the mixture was stirred and heated to reflux for 3 hour. After returning the mixture to room temperature, triethylamine (0.631 mL, 4.53 mmol) and tert-butanol (0.289 mL, 3.02 mmol) were added and the mixture was stirred and heated to reflux for 3 hour. After returning the mixture to room temperature, the solvent in the mixture was distilled off under reduced pressure and the residue was purified by silica gel column chromatography (mixture of n-heptane and ethyl acetate: n-heptane/ethyl acetate=1/4) to obtain the title compound (144 mg, 0.535 mmol).

$^1$H-NMR (CDCl$_3$) δ: 1.51 (s, 9H), 3.98 (s, 3H), 6.12 (br.s, 1H), 6.54 (d, J=4.0 Hz, 1H), 7.48 (d, J=4.4 Hz, 1H).

(2e) tert-Butyl (3-bromo-6-methoxypyrazolo[5,1-b][1,3]thiazol-7-yl)carbamate

[Chemical Formula 36]

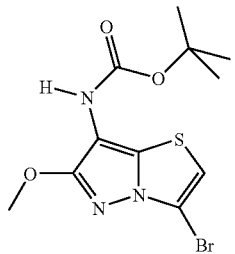

To a mixture of tert-butyl (6-methoxypyrazolo[5,1-b][1,3]thiazol-7-yl)carbamate (16.5 g, 61.4 mmol) and THF (410 mL) was added n-butyllithium (2.77 M solution in n-hexane: 62.1 mL, 172 mmol) while stirring at −78° C. After further stirring the mixture at −78° C. for 40 minutes, 1,2-dibromotetrafluoroethane (10.2 mL, 86 mmol) was added and stirring was continued for 2 hours while heating to room temperature. A saturated aqueous solution of ammonium chloride and ethyl acetate were added to the mixture, and then acetic acid was added to a weakly acidic pH of the mixture. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=1/0 then 4/1) to obtain the title compound (14.3 g, 41.1 mmol).

$^1$H-NMR (CDCl$_3$) δ: 1.51 (s, 9H), 4.04 (s, 3H), 6.16 (br.s, 1H), 6.50 (s, 1H).

(2f) tert-Butyl {3-[4-(ethoxymethyl)-2,6-dimethoxyphenyl]-6-methoxypyrazolo[5,1-b][1,3]thiazol-7-yl}carbamate

[Chemical Formula 37]

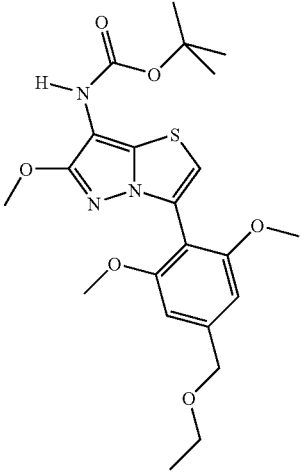

To a mixture of tert-butyl (3-bromo-6-methoxypyrazolo[5,1-b][1,3]thiazol-7-yl)carbamate (2.00 g, 5.74 mmol), DME (200 mL) and water (70 mL) were added 2,6-dimethoxy-4-(ethoxymethyl)phenylboric acid (Production Example 33 of WO 04/037822) (2.07 g, 8.64 mmol), potassium carbonate (1.59 g, 11.5 mmol), triphenylphosphine (0.75 g, 2.87 mmol) and palladium acetate (0.13 g, 0.57 mmol) in that order, and the mixture was stirred at 90° C. (internal temperature) for 4 hours. Water was added to the reaction mixture, and then ethyl acetate was added.

After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=2/1 then 1/1) to obtain the title compound (2.49 g, 5.37 mmol).

$^1$H-NMR (CDCl$_3$) δ: 1.29 (t, J=7.2 Hz, 3H), 1.52 (s, 9H), 3.61 (q, J=7.2 Hz, 2H), 3.75 (s, 6H), 3.87 (s, 3H), 4.53 (s, 2H), 6.09 (br.s, 1H), 6.42 (s, 1H), 6.64 (s, 2H).

(2g) N-Butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine

[Chemical Formula 38]

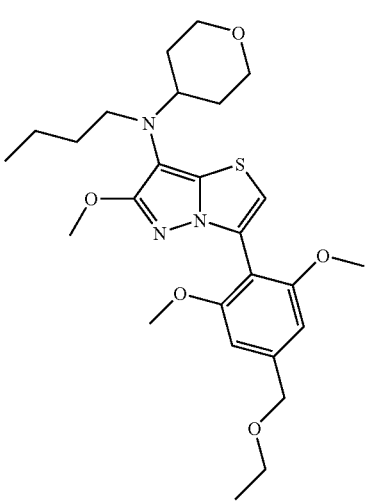

To a mixture of tert-butyl {3-[4-(ethoxymethyl)-2,6-dimethoxyphenyl]-6-methoxypyrazolo[5,1-b][1,3]thiazol-7-yl}carbamate (100 mg, 0.22 mmol) and DMF (5 mL) was added sodium hydride (60% dispersion in oil: 11.2 mg, 0.28 mmol) at room temperature, and the mixture was stirred for 30 minutes. After then adding 1-iodobutane (33.0 μL, 0.28 mmol) to the mixture, stirring was continued for 30 minutes. Water was added to the mixture while cooling on ice, and then ethyl acetate was added.

After thoroughly shaking the mixture, the organic layer was separated and the organic layer was washed with brine and dried over anhydrous magnesium sulfate. The mixture was filtered, and then the solvent in the filtrate was distilled off under reduced pressure.

Dichloromethane (5 mL) was added to the resulting residue, trifluoroacetic acid (1 mL) was added, and the mixture was stirred at room temperature for 1 hour. The solvent in the filtrate was distilled off under reduced pressure.

THF (10 mL) was then added to the resulting residue, tetrahydro-4H-pyran-4-one (42.2 μL, 0.43 mmol), acetic acid (1 mL) and sodium triacetoxyborohydride (91.6 mg, 0.43 mmol) were added in that order, and the mixture was stirred at room temperature for 14 hours.

To this mixture was added aqueous 5N sodium hydroxide to approximate neutral pH of the mixture while cooling on ice, and then ethyl acetate was added.

After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=2/1 then 1/1) to obtain the title compound (81.0 mg, 0.16 mmol).

$^1$H-NMR (CDCl$_3$) δ: 0.87 (t, J=6.8 Hz, 3H), 1.30 (t, J=6.8 Hz, 3H), 1.24-1.40 (m, 4H), 1.52-1.67 (m, 2H), 1.78-1.87 (m, 2H), 2.97 (t, J=6.8 Hz, 2H), 2.99-3.11 (m, 1H), 3.38 (td, J=1.6, 11.6 Hz, 2H), 3.63 (q, J=7.2 Hz, 2H), 3.79 (s 6H), 3.86 (s, 3H), 3.94-4.03 (m, 2H), 4.55 (s, 2H), 6.41 (s, 1H), 6.66 (s, 2H).

Example 3

N-(2-Cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine

[Chemical Formula 39]

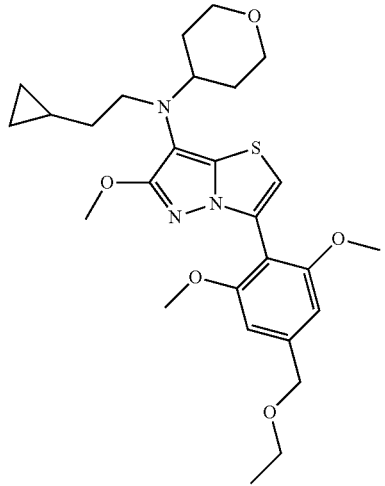

To a mixture of tert-butyl {3-[4-(ethoxymethyl)-2,6-dimethoxyphenyl]-6-methoxypyrazolo[5,1-b][1,3]thiazol-7-yl}carbamate (100 mg, 0.216 mmol) and DMSO (5 mL) were added powdered sodium hydroxide (17.3 mg, 0.432 mmol) and 2-cyclopropylethyl methanesulfonate (70.9 mg, 0.432 mmol) in that order at room temperature, and the mixture was stirred for 1 hour. Water was added to the mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure.

Dichloromethane (5 mL) was added to the resulting residue, trifluoroacetic acid (1 mL) was added, and the mixture was stirred at room temperature for 1 hour. The solvent in the filtrate was distilled off under reduced pressure.

THF (10 mL) was then added to the resulting residue, tetrahydro-4H-pyran-4-one (42.2 μL, 0.432 mmol), acetic acid (1 mL) and sodium triacetoxyborohydride (91.6 mg, 0.432 mmol) were added in that order, and the mixture was stirred at room temperature for 4 hours.

To this mixture there was added aqueous 5N sodium hydroxide to approximate neutral pH of the mixture while cooling on ice, and then ethyl acetate was added.

After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by silica gel column chromatography (mixture of n-heptane and ethyl acetate: n-heptane/ethyl acetate=2/1 then 1/1) to obtain the title compound (78.9 mg, 0.15 mmol).

$^1$H-NMR (CDCl$_3$) δ: −0.02-0.06 (m, 2H), 0.34-0.44 (m, 2H), 0.62-0.76 (m, 1H), 1.32 (t, J=6.8 Hz, 3H), 1.24-1.37 (m, 2H), 1.54-1.70 (m, 2H), 1.80-1.90 (m, 2H), 3.10 (t, J=7.6 Hz, 2H), 3.02-3.16 (m, 1H), 3.40 (td, J=1.6, 11.6 Hz, 2H), 3.64 (q, J=7.2 Hz, 2H), 3.81 (s, 6H), 3.87 (s, 3H), 3.96-4.06 (m, 2H), 4.57 (s, 2H), 6.43 (s, 1H), 6.68 (s, 2H).

Example 4

N-(Cyclobutylmethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine

[Chemical Formula 40]

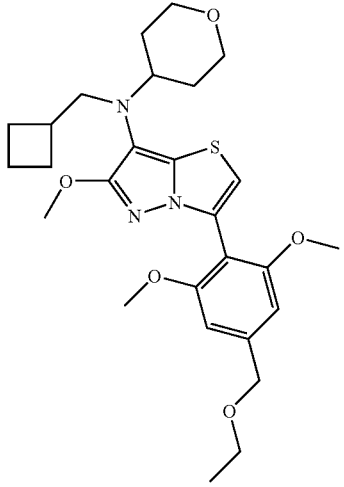

To mixture of tert-butyl {3-[4-(ethoxymethyl)-2,6-dimethoxyphenyl]-6-methoxypyrazolo[5,1-b][1,3]thiazol-7-yl}carbamate (100 mg, 0.216 mmol) and DMSO (0.5 mL) were added powdered sodium hydroxide (17.3 mg, 0.43 mmol) and (bromomethyl)cyclobutane (36.4 μL, 0.324 mmol) in that order at room temperature, and the mixture was stirred for 1 hour. A saturated aqueous solution of ammonium chloride and ethyl acetate were added to the reaction mixture. After thoroughly shaking the mixture, the organic layer was separated and the solvent was distilled off with a nitrogen airflow.

Dichloromethane (0.6 mL) was added to the resulting residue, trifluoroacetic acid (0.3 mL) was added, and the mixture was stirred at room temperature for 1 hour. The solvent in the mixture was then distilled off with a nitrogen airflow. THF (1 mL) was added to the resulting residue, tetrahydro-4H-pyran-4-one (29.8 μL, 0.324 mmol) and sodium triacetoxyborohydride (68.7 mg, 0.324 mmol) were added in that order, and the mixture was stirred at room temperature for 1 hour. A saturated aqueous solution of sodium hydrogencarbonate was added to the mixture, and ethyl acetate was added. After thoroughly shaking the mixture, the organic layer was separated and the solvent was distilled off with a nitrogen airflow. The residue was purified by silica gel column chromatography (mixture of n-heptane and ethyl acetate: n-heptane/ethyl acetate=19/1 then 2.3/1) to obtain the title compound (98.9 mg, 0.192 mmol).

$^1$H-NMR (CDCl$_3$) δ: 1.30 (t, J=4.0 Hz, 3H), 1.50-1.64 (m, 4H), 1.66-1.89 (m, 6H), 2.28-2.39 (m, 1H), 2.96-3.06 (m, 1H), 2.99 (d, J=6.8 Hz, 2H), 3.37 (dt, J=2.0, 12.0 Hz, 2H), 3.62 (q, J=7.0 Hz, 2H), 3.77 (s, 6H), 3.85 (s, 3H), 3.93-4.00 (m, 2H), 4.54 (s, 2H), 6.40 (s, 1H), 6.65 (s, 2H).

Example 5

N-(Cyclopropylmethyl)-3-[4-(ethoxymethyl)-2,6-dimethoxyphenyl]-6-methoxy-N-(tetrahydro-2H-pyran-3-yl)pyrazolo[5,1-b][1,3]thiazole-7-amine

[Chemical Formula 41]

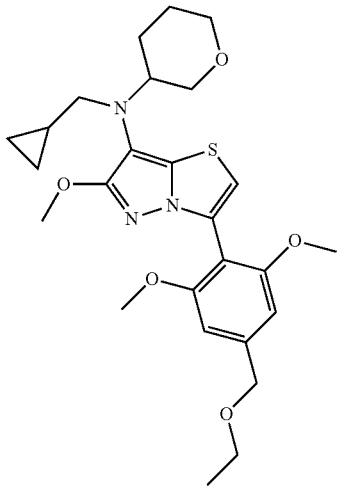

To a mixture of tert-butyl {3-[4-(ethoxymethyl)-2,6-dimethoxyphenyl]-6-methoxypyrazolo[5,1-b][1,3]thiazol-7-yl}carbamate (120 mg, 0.259 mmol) and DMSO (0.8 mL) were added powdered sodium hydroxide (20.8 mg, 0.516 mmol) and cyclopropylmethyl bromide (37.7 μL, 0.389 mmol) at room temperature, and the mixture was stirred for 1 hour. A saturated aqueous solution of ammonium chloride and ethyl acetate were added to the reaction mixture. After thoroughly shaking the mixture, the organic layer was separated and the solvent was distilled off with a nitrogen airflow.

Dichloromethane (0.6 mL) was added to the resulting residue, trifluoroacetic acid (0.3 mL) was further added, and the mixture was stirred at room temperature for 1 hour. The solvent in the mixture was then distilled off with a nitrogen airflow. THF (1 mL) was then added to the resulting residue, dihydro-2H-pyran-3(4H)-one (38.9 mg, 0.389 mmol) and sodium triacetoxyborohydride (82.4 mg, 0.389 mmol) were added in that order, and the mixture was stirred at room temperature for 1 hour. A saturated aqueous solution of sodium hydrogencarbonate was added to the mixture, and ethyl acetate was added. After thoroughly shaking the mixture, the organic layer was separated and the solvent was distilled off with a nitrogen airflow. The residue was purified by silica gel column chromatography (mixture of n-heptane and ethyl acetate: n-heptane/ethyl acetate=19/1 then 2.3/1) to obtain the title compound (93.8 mg, 0.187 mmol).

$^1$H-NMR (CDCl$_3$) δ: –0.02-0.05 (m, 2H), 0.28-0.37 (m, 2H), 0.77-0.91 (m, 1H), 1.23-1.33 (m, 1H), 1.30 (t, J=7.0 Hz, 3H), 1.33-1.46 (m, 1H), 1.58-1.72 (m, 1H), 2.06 (br.d, J=12.0 Hz, 1H), 2.82-2.94 (m, 2H), 3.09-3.24 (m, 3H), 3.62 (q, J=7.0 Hz, 2H), 3.73-3.89 (m, 1H), 3.78 (s, 6H), 3.86 (s, 3H), 4.08 (br.d, J=9.2 Hz, 1H), 4.54 (s, 2H), 6.42 (s, 1H), 6.66 (s, 2H).

Example 6

3-[4-(Ethoxymethyl)-2,6-dimethoxyphenyl]-6-methoxy-N-propyl-N-(tetrahydro-2H-pyran-3-yl)pyrazolo[5,1-b][1,3]thiazole-7-amine

[Chemical Formula 42]

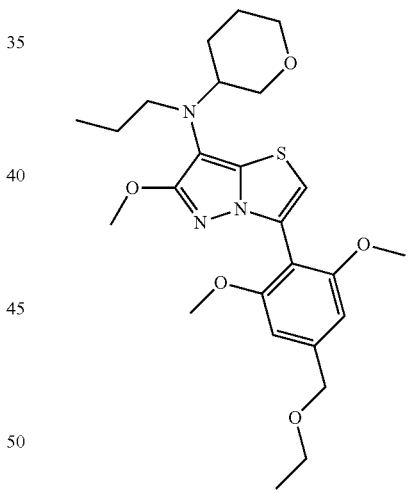

To a mixture of tert-butyl {3-[4-(ethoxymethyl)-2,6-dimethoxyphenyl]-6-methoxypyrazolo[5,1-b][1,3]thiazol-7-yl}carbamate (120 mg, 0.259 mmol) and DMSO (0.8 mL) were added powdered sodium hydroxide (20.8 mg, 0.516 mmol) and 1-iodopropane (37.9 μL, 0.389 mmol) in that order at room temperature, and the mixture was stirred for 1 hour. A saturated aqueous solution of ammonium chloride and ethyl acetate were added to the reaction mixture. After thoroughly shaking the mixture, the organic layer was separated and the solvent was distilled off with a nitrogen airflow.

Dichloromethane (0.6 mL) was added to the resulting residue, trifluoroacetic acid (0.3 mL) was added, and the mixture was stirred at room temperature for 1 hour. The solvent in the mixture was then distilled off with a nitrogen airflow. THF (1 mL) was then added to the resulting residue, dihydro-2H-pyran-3(4H)-one (38.9 mg, 0.389 mmol) and sodium triacetoxyborohydride (82.4 mg, 0.389 mmol) were added in that order, and the mixture was stirred at room temperature for 1 hour. A saturated aqueous solution of sodium hydrogencarbonate was added to the mixture, and ethyl acetate was further added. After thoroughly shaking the mixture, the organic layer was separated and the solvent was distilled off under a nitrogen stream. The residue was purified by silica gel column chromatography (mixture of n-heptane and ethyl acetate: n-heptane/ethyl acetate=19/1 then 2.3/1) to obtain the title compound (83.6 mg, 0.171 mmol).

$^1$H-NMR (CDCl$_3$) δ: 0.86 (t, J=7.2 Hz, 3H), 1.26-1.57 (m, 3H), 1.30 (t, J=7.0 Hz, 3H), 1.59-1.68 (m, 2H), 2.02-2.10 (m, 1H), 2.94 (t, J=7.4 Hz, 2H), 3.04 (tt, J=4.0, 10.8 Hz, 1H), 3.14-3.24 (m, 2H), 3.62 (q, J=7.0 Hz, 2H), 3.72-3.88 (m, 1H), 3.79 (s, 6H), 3.85 (s, 3H), 4.04-4.11 (m, 1H), 4.54 (s, 2H), 6.42 (s, 1H), 6.66 (s, 2H).

Example 7

N-(Cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine

[Chemical Formula 43]

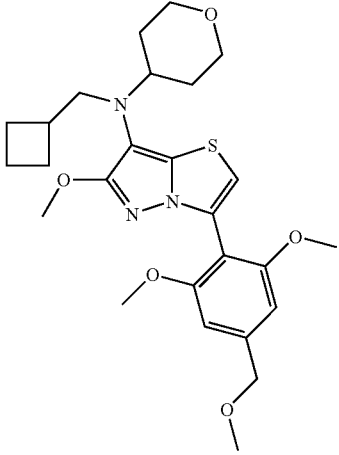

(7a) tert-Butyl {3-[2,6-dimethoxy-4-(methoxymethyl)phenyl]-6-methoxypyrazolo[5,1-b][1,3]thiazol-7-yl}carbamate

[Chemical Formula 44]

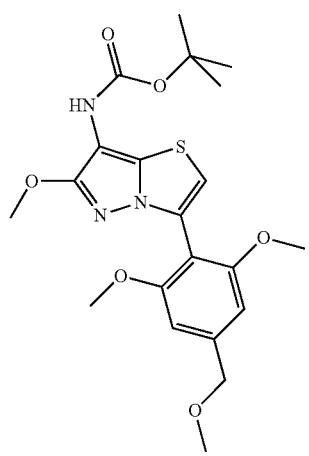

To a mixture of tert-butyl (3-bromo-6-methoxypyrazolo[5,1-b][1,3]thiazol-7-yl)carbamate (998 mg, 2.87 mmol), DME (107 mL) and water (36 mL) were added 2,6-dimethoxy-4-(methoxymethyl)phenylboric acid (Production Example 29 of WO 04/03782) (973 mg, 4.31 mmol), potassium carbonate (791 mg, 5.74 mmol), triphenylphosphine (374 mg, 1.43 mmol) and palladium acetate (64.5 mg, 0.285 mmol) in that order, and the mixture was stirred at 90° C. (internal temperature) for 1.5 hours. Water was added to the mixture, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by silica gel column chromatography (mixture of n-heptane and ethyl acetate: n-heptane/ethyl acetate=2/1 then 1/1) to obtain the title compound (1.22 g, 2.71 mmol).

$^1$H-NMR (CDCl$_3$) δ: 1.52 (s, 9H), 3.46 (s, 3H), 3.75 (s, 6H), 3.87 (s, 3H), 4.49 (s, 2H), 6.09 (br.s, 1H), 6.43 (s, 1H), 6.63 (s, 2H).

(7b) N-(Cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine

[Chemical Formula 45]

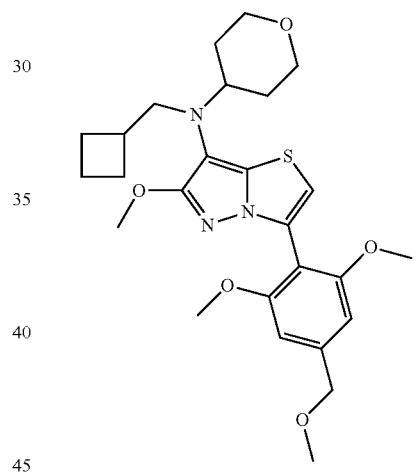

Sodium hydride (60% dispersion in oil: 34.5 mg, 0.863 mmol) was added to a mixture of tert-butyl {3-[2,6-dimethoxy-4-(methoxymethyl)phenyl]-6-methoxypyrazolo[5,1-b][1,3]thiazol-7-yl}carbamate (300 mg, 0.664 mmol) and DMF (6 mL) at room temperature, and the mixture was stirred for 30 minutes. To this mixture was added (bromomethyl)cyclobutane (97.0 µL, 0.863 mmol), and stirring was continued for 2 hours and 40 minutes. Water was added to the mixture while cooling on ice, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure.

Dichloromethane (10 mL) was then added to the resulting residue, trifluoroacetic acid (4 mL) was added, and the mixture was stirred at room temperature for 1 hour and 20 minutes. The solvent in the filtrate was distilled off under reduced pressure.

THF (30 mL) was then added to the resulting residue, tetrahydro-4H-pyran-4-one (123 µL, 1.33 mmol) and sodium triacetoxyborohydride (282 mg, 1.33 mmol) were added in that order, and the mixture was stirred at room temperature for 2 hours and 50 minutes.

A saturated aqueous solution of sodium hydrogencarbonate was added to the mixture while cooling on ice, and ethyl acetate was added.

After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by silica gel column chromatography (mixture of n-heptane and ethyl acetate: n-heptane/ethyl acetate=9/1 then 3/2) to obtain the title compound (237 mg, 0.472 mmol).

$^1$H-NMR (CDCl$_3$) δ: 1.50-1.64 (m, 4H), 1.68-1.89 (m, 6H), 2.29-2.39 (m, 1H), 2.99 (d, J=7.2 Hz, 2H), 2.97-3.05 (m, 1H), 3.33-3.41 (m, 2H), 3.47 (s, 3H), 3.78 (s, 6H), 3.85 (s, 3H), 3.93-4.01 (m, 2H), 4.50 (s, 2H), 6.41 (s, 1H), 6.64 (s, 2H).

Example 8

3-[2,6-Dimethoxy-4-(methoxymethyl)phenyl]-6-methoxy-N-pentyl-N-(tetrahydro-2H-pyran-4-yl)pyrazolo[5,1-b][1,3]thiazole-7-amine

[Chemical Formula 46]

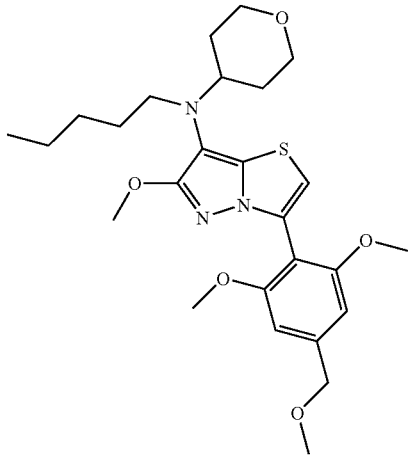

Sodium hydride (60% dispersion in oil: 11.6 mg, 0.289 mmol) was added to a mixture of tert-butyl {3-[2,6-dimethoxy-4-(methoxymethyl)phenyl]-6-methoxypyrazolo[5,1-b][1,3]thiazol-7-yl}carbamate (100 mg, 0.222 mmol) and DMF (2 mL) at room temperature, and the mixture was stirred for 30 minutes. After then adding 1-bromopentane (35.8 μL, 0.289 mmol) to the mixture, stirring was continued for 30 minutes. Water was added to the mixture while cooling on ice, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure.

Dichloromethane (5 mL) was then added to the resulting residue, trifluoroacetic acid (2 mL) was added, and the mixture was stirred at room temperature for 1 hour. The solvent in the filtrate was distilled off under reduced pressure.

THF (10 mL) was then added to the resulting residue, tetrahydro-4H-pyran-4-one (40.8 μL, 0.444 mmol) and sodium triacetoxyborohydride (94.1 mg, 0.444 mmol) were added in that order, and the mixture was stirred at room temperature for 1 hour. A saturated aqueous solution of sodium hydrogencarbonate was added to the mixture while cooling on ice, and ethyl acetate was added.

After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by silica gel column chromatography (mixture of n-heptane and ethyl acetate: n-heptane/ethyl acetate=9/1 then 3/2) to obtain the title compound (83.3 mg, 0.17 mmol).

$^1$H-NMR (CDCl$_3$) δ: 0.85 (t, J=6.8 Hz, 3H), 1.22-1.32 (m, 4H), 1.32-1.41 (m, 2H), 1.53-1.65 (m, 2H), 1.78-1.86 (m, 2H), 2.97 (dd, J=7.2, 7.6 Hz, 2H), 3.00-3.10 (m, 1H), 3.33-3.43 (m, 2H), 3.47 (s, 3H), 3.79 (s, 6H), 3.86 (s, 3H), 3.94-4.02 (m, 2H), 4.50 (s, 2H), 6.42 (s, 1H), 6.65 (s, 2H).

Example 9

N-(Cyclopropylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine

[Chemical Formula 47]

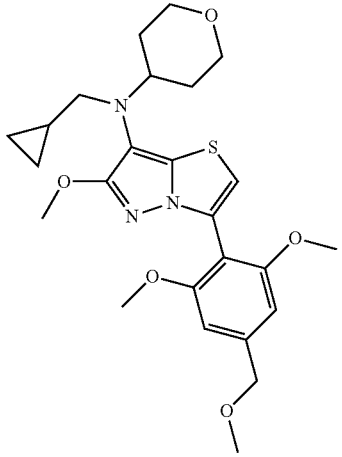

Sodium hydride (60% dispersion in oil: 9.28 mg, 0.232 mmol) was added to a mixture of tert-butyl {3-[2,6-dimethoxy-4-(methoxymethyl)phenyl]-6-methoxypyrazolo[5,1-b][1,3]thiazol-7-yl}carbamate (80 mg, 0.178 mmol) and DMF (5 mL) at room temperature, and the mixture was stirred for 30 minutes. After then adding bromomethylcyclopropane (22.6 μL, 0.232 mmol) to the mixture, stirring was continued for 30 minutes. Water was added to the mixture while cooling on ice, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure.

Dichloromethane (5 mL) was then added to the resulting residue, trifluoroacetic acid (1 mL) was added, and the mixture was stirred at room temperature for 1 hour. The solvent in the filtrate was distilled off under reduced pressure.

After then adding methanol (6 mL), and then tetrahydro-4H-pyran-4-one (34.8 μL, 0.356 mmol), acetic acid (1 mL) and α-picolineborane (38.1 mg, 0.356 mmol) in that order to the obtained residue, the mixture was stirred for 1 hour at room temperature. To this mixture was added aqueous 5N sodium hydroxide to approximate neutral pH of the mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=1/1) to obtain the title compound (62.4 mg, 0.128 mmol).

$^1$H-NMR (CDCl$_3$) δ: −0.02-0.06 (m, 2H), 0.29-0.40 (m, 2H), 0.78-0.92 (m, 1H), 1.50-1.66 (m, 2H), 1.78-1.88 (m, 2H), 2.88 (d, J=6.8 Hz, 2H), 3.10-3.22 (m, 1H), 3.39 (td, J=1.6, 11.6 Hz, 2H), 3.47 (s, 3H), 3.79 (s, 6H), 3.87 (s, 3H), 3.92-4.03 (m, 2H), 4.50 (s, 2H), 6.41 (s, 1H), 6.65 (s, 2H).

Example 10

3-[2,6-Dimethoxy-4-(methoxymethyl)phenyl]-6-methoxy-N-propyl-N-(tetrahydro-2H-pyran-4-yl)pyrazolo[5,1-b][1,3]thiazole-7-amine

[Chemical Formula 48]

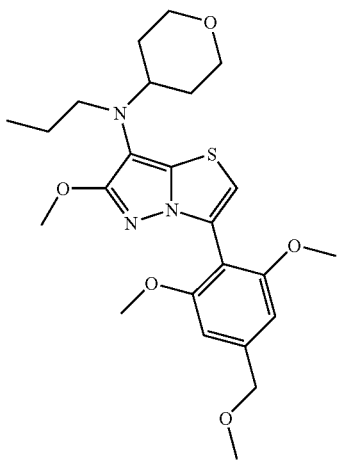

Sodium hydride (60% dispersion in oil: 6.73 mg, 0.168 mmol) was added to a mixture of tert-butyl {3-[2,6-dimethoxy-4-(methoxymethyl)phenyl]-6-methoxypyrazolo[5,1-b][1,3]thiazol-7-yl}carbamate (58 mg, 0.13 mmol) and DMF (4 mL) at room temperature, and the mixture was stirred for 30 minutes. After then adding 1-iodopropane (16.4 μL, 0.168 mmol) to the mixture, stirring was continued for 30 minutes. Water was added to the mixture while cooling on ice, and then ethyl acetate was further added. After thoroughly shaking the mixture, the organic layer was separated and the organic layer was washed with brine and dried over anhydrous magnesium sulfate. The mixture was filtered, and then the solvent in the filtrate was distilled off under reduced pressure.

Dichloromethane (5 mL) was added to the resulting residue, trifluoroacetic acid (1 mL) was further added, and the mixture was stirred at room temperature for 1 hour. The solvent in the filtrate was distilled off under reduced pressure.

After then adding methanol (6 mL), and then tetrahydro-4H-pyran-4-one (25.4 μL, 0.26 mmol), acetic acid (1 mL) and α-picolineborane (27.8 mg, 0.26 mmol) in that order to the obtained residue, the mixture was stirred for 1 hour at room temperature. To this mixture there was added aqueous 5N sodium hydroxide to approximate neutral pH of the mixture while cooling on ice, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by silica gel column chromatography (mixture of n-heptane and ethyl acetate: n-heptane/ethyl acetate=1/1) to obtain the title compound (50.0 mg, 0.105 mmol).

$^1$H-NMR (CDCl$_3$) δ: 0.87 (t, J=7.2 Hz, 3H), 1.32-1.45 (m, 2H), 1.53-1.66 (m, 2H), 1.78-1.88 (m, 2H), 2.90-2.99 (m, 2H), 3.00-3.12 (m, 1H), 3.38 (td, J=2.0, 12.0 Hz, 2H), 3.47 (s, 3H), 3.79 (s, 6H), 3.86 (s, 3H), 3.94-4.03 (m, 2H), 4.50 (s, 2H), 6.42 (s, 1H), 6.65 (s, 2H).

Example 11

N-(Cyclopropylmethyl)-3-[2,6-dimethoxy-4-(methoxymethyl)phenyl]-6-methoxy-N-(tetrahydro-2H-pyran-3-yl)pyrazolo[5,1-b][1,3]thiazole-7-amine

[Chemical Formula 49]

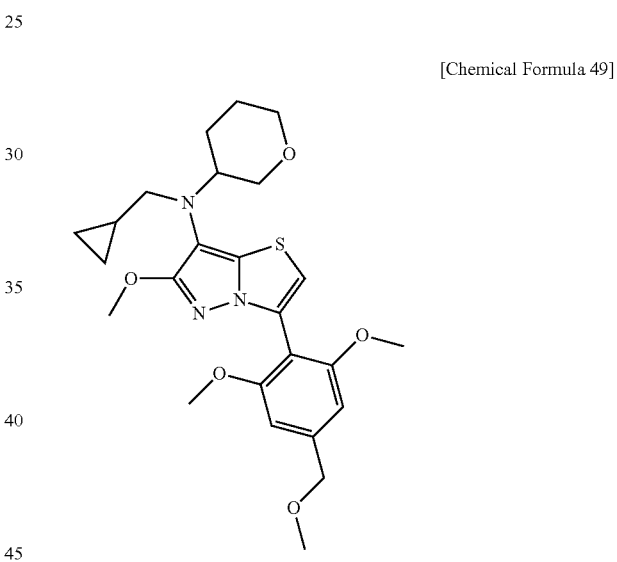

To a mixture of tert-butyl {3-[2,6-dimethoxy-4-(methoxymethyl)phenyl]-6-methoxypyrazolo[5,1-b][1,3]thiazol-7-yl}carbamate (120 mg, 0.267 mmol) and DMSO (0.8 mL) were added powdered sodium hydroxide (21.4 mg, 0.534 mmol) and cyclopropylmethyl bromide (38.8 μL, 0.401 mmol) at room temperature, and the mixture was stirred for 1 hour. A saturated aqueous solution of ammonium chloride and ethyl acetate were added to the reaction mixture. After thoroughly shaking the mixture, the organic layer was separated and the solvent was distilled off with a nitrogen airflow.

Dichloromethane (0.6 mL) was added to the resulting residue, trifluoroacetic acid (0.3 mL) was added, and the mixture was stirred at room temperature for 1 hour. The solvent in the mixture was then distilled off with a nitrogen airflow. THF (1 mL) was added to the resulting residue, dihydro-2H-pyran-3(4H)-one (40.1 mg, 0.401 mmol) and sodium triacetoxyborohydride (84.9 mg, 0.401 mmol) were added in that order, and the mixture was stirred at room temperature for 1 hour. A saturated aqueous solution of sodium hydrogencarbonate was added to the mixture, and ethyl acetate was added. After thoroughly shaking the mixture, the organic layer was separated and the solvent was distilled off under a nitrogen stream. The residue was purified by silica gel column chromatography (mixture of n-heptane and ethyl acetate: n-heptane/ethyl acetate=19/1 then 2.3/1) to obtain the title compound (96.1 mg, 0.197 mmol).

$^1$H-NMR (CDCl$_3$) δ: −0.02-0.05 (m, 2H), 0.30-0.37 (m, 2H), 0.77-0.88 (m, 1H), 1.34-1.46 (m, 1H), 1.60-1.69 (m, 2H), 2.02-2.10 (m, 1H), 2.86 (dd, J=6.4, 12.8 Hz, 1H), 2.90 (dd, J=6.4, 12.8 Hz, 1H), 3.08-3.24 (m, 3H), 3.47 (s, 3H), 3.75-3.88 (m, 1H), 3.78 (s, 6H), 3.86 (s, 3H), 4.05-4.11 (m, 1H), 4.50 (s, 2H), 6.43 (s, 1H), 6.65 (s, 2H).

Example 12

3-[2,6-Dimethoxy-4-(methoxymethyl)phenyl]-6-methoxy-N-[(2-methylcyclopropyl)methyl]-N-(tetrahydro-2H-pyran-4-yl)pyrazolo[5,1-b][1,3]thiazole-7-amine

[Chemical Formula 50]

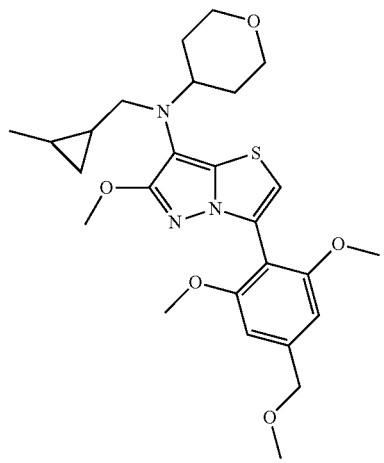

(12a) 3-[2,6-Dimethoxy-4-(methoxymethyl)phenyl]-6-methoxypyrazolo[5,1-b][1,3]thiazole-7-amine

[Chemical Formula 51]

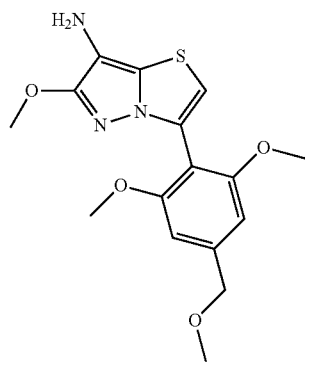

To a mixture of tert-butyl {3-[2,6-dimethoxy-4-(methoxymethyl)phenyl]-6-methoxypyrazolo[5,1-b][1,3]thiazol-7-yl}carbamate (1.37 g, 3.05 mmol) and ethyl acetate (10 mL) was added a 4M solution of HCl in ethyl acetate (20 mL), and the mixture was stirred at room temperature for 3 hours. The solvent in the mixture was distilled off under reduced pressure, and then ethyl acetate was added to the obtained residue and a saturated aqueous solution of sodium carbonate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure. To the residue there was added a mixture of n-heptane and ethyl acetate, and the precipitated solid was collected by filtration and dried under reduced pressure to obtain the title compound (836.6 mg, 2.39 mmol).

$^1$H-NMR (CDCl$_3$) δ: 2.60 (br.s, 2H), 3.46 (s, 3H), 3.77 (s, 6H), 3.89 (s, 3H), 4.50 (s, 2H), 6.40 (s, 1H), 6.64 (s, 2H).

(12b) N-{3-[2,6-Dimethoxy-4-(methoxymethyl)phenyl]-6-methoxypyrazolo[5,1-b][1,3]thiazol-7-yl}-2-methylcyclopropanecarboxamide

[Chemical Formula 52]

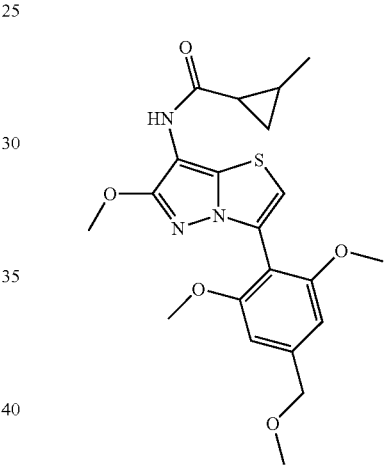

To a mixture of WSCD (104 mg, 0.67 mmol) and DMF (5 mL) was added 1-hydroxybenzotriazole (90.4 mg 0.67 mmol, and then 3-(2,6-dimethoxy-4-methoxymethylphenyl)-6-methoxypyrazolo[5,1-b]thiazol-7-ylamine (200 mg, 0.57 mmol) and 2-methylcyclopropanecarboxylic acid (60.8 μL, 0.62 mmol) were added in that order and the mixture was stirred at room temperature for 14 hours. Water was added to the reaction mixture, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by (NH)silica gel chromatography (mixture of n-heptane and ethyl acetate: n-heptane/ethyl acetate=1/1) to obtain the title compound (215.9 mg, 0.50 mmol).

$^1$H-NMR (CDCl$_3$) δ: 0.65-0.68 (m, 1H), 1.14 (d, J=6.0 Hz, 3H), 1.21-1.31 (m, 2H), 1.46-1.52 (m, 1H), 3.46 (s, 3H), 3.75 (s, 6H), 3.90 (s, 3H), 4.49 (s, 2H), 6.43 (s, 1H), 6.62 (s, 2H), 7.14 (br.s, 1H).

(12c) 3-[2,6-Dimethoxy-4-(methoxymethyl)phenyl]-6-methoxy-N-[(2-methylcyclopropyl)methyl]-N-(tetrahydro-2H-pyran-4-yl)pyrazolo[5,1-b][1,3]thiazole-7-amine

[Chemical Formula 53]

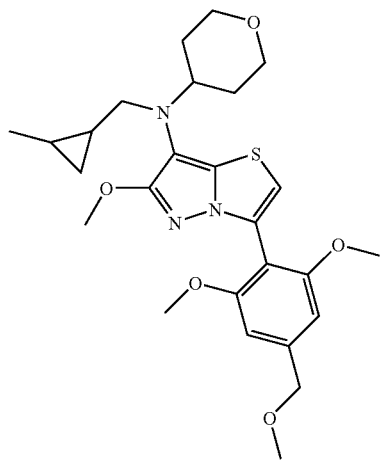

To a mixture of N-{3-[2,6-dimethoxy-4-(methoxymethyl)phenyl]-6-methoxypyrazolo[5,1-b][1,3]thiazol-7-yl}-2-methylcyclopropanecarboxamide (100 mg, 0.23 mmol) and THF (2 mL) was added a solution of borane in tetrahydrofuran (0.99 M, 609 μL, 0.60 mmol), and the mixture was stirred at 55° C. for 2 hours. Water was added to the reaction mixture, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure. To a mixture of the obtained residue and THF (1.5 mL) were added trifluoroacetic acid (150 μL), and then tetrahydro-4H-pyran-4-one (32 μL, 0.35 mmol) and sodium triacetoxyborohydride (73.8 mg, 0.35 mmol) in that order, and the mixture was stirred at room temperature for 1 hour. Water was added to the reaction mixture, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by (NH)silica gel column chromatography (mixture of n-heptane and ethyl acetate: n-heptane/ethyl acetate=4/1). The fractions containing the target substance were collected, the solvent was distilled off under reduced pressure, and then a mixture of n-heptane and diisopropyl ether was added to the resulting residue. The precipitated solid was collected by filtration, and the obtained residue was washed with a small amount of n-heptane and then dried under reduced pressure to obtain the title compound (43.7 mg, 0.09 mmol).

$^1$H-NMR (CDCl$_3$) δ: 0.06-0.10 (m, 1H), 0.15-0.19 (m, 1H), 0.26-0.36 (m, 1H), 0.47-0.58 (m, 1H), 0.79 (d, J=5.6 Hz, 3H), 1.50-1.68 (m, 2H), 1.78-1.89 (m, 2H), 2.68 (dd, J=8.0, 12.0 Hz, 1H), 3.04-3.18 (m, 2H), 3.33-3.46 (m, 2H), 3.48 (s, 3H), 3.79 (s, 6H), 3.87 (s, 3H), 3.94-4.03 (m, 2H), 4.52 (s, 2H), 6.41 (s, 1H), 6.66 (s, 2H).

Example 13

3-[2-Chloro-6-methoxy-4-(methoxymethyl)phenyl]-6-methoxy-N-propyl-N-(tetrahydro-2H-pyran-4-yl)pyrazolo[5,1-b][1,3]thiazole-7-amine

[Chemical Formula 54]

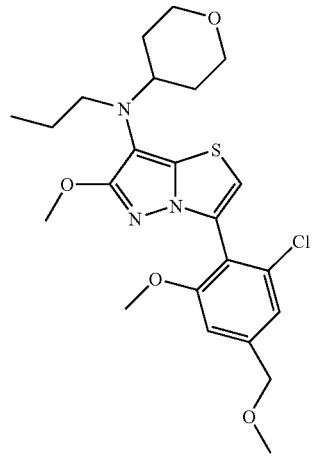

(13a) tert-Butyl {3-[2-chloro-6-methoxy-4-(methoxymethyl)phenyl]-6-methoxy-pyrazolo[5,1-b][1,3]thiazol-7-yl}carbamate

[Chemical Formula 55]

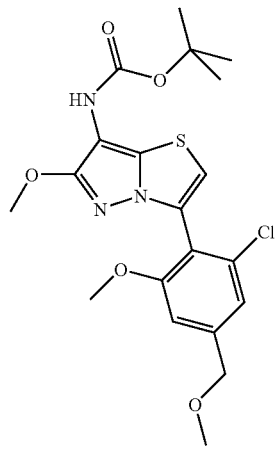

To a mixture of tert-butyl (3-bromo-6-methoxypyrazolo[5,1-b][1,3]thiazol-7-yl)carbamate (500 mg, 1.44 mmol) toluene (8 mL) and ethanol (4 mL) were added [2-chloro-6-methoxy-4-(methoxymethyl)phenyl]boronic acid (498 mg, 2.16 mmol), a 1M aqueous solution of sodium carbonate (2.88 mL, 2.88 mmol) and tetrakis(triphenylphosphine)palladium(0) (166 mg, 0.14 mmol) in that order, and the mixture was stirred at 110° C. for 6 hours. Water was added to the mixture, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure. The residue was purified by (NH)silica gel column chromatography (mixture of n-heptane and ethyl acetate: n-heptane/ethyl acetate=3/1 then 2/1) to obtain the title compound (349 mg, 0.77 mmol).

¹H-NMR (CDCl₃) δ: 1.52 (s, 9H), 3.46 (s, 3H), 3.76 (s, 3H), 3.87 (s, 3H), 4.48 (s, 2H), 6.13 (br.s, 1H), 6.48 (s, 1H), 6.91 (s, 1H), 7.08 (s, 1H).

(13b) 3-[2-Chloro-6-methoxy-4-(methoxymethyl)phenyl]-6-methoxy-N-propyl-N-(tetrahydro-2H-pyran-4-yl)pyrazolo[5,1-b][1,3]thiazole-7-amine

[Chemical Formula 56]

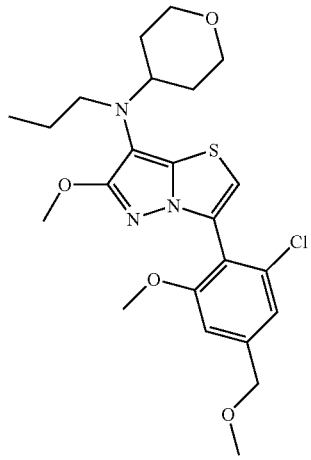

To a mixture of tert-butyl {3-[2-chloro-6-methoxy-4-(methoxymethyl)phenyl]-6-methoxy-pyrazolo[5,1-b][1,3]thiazol-7-yl}carbamate (148 mg, 0.33 mmol) and DMF (4 mL) was added sodium hydride (60% dispersion in oil: 17 mg, 0.42 mmol) at room temperature, and the mixture was stirred for 10 minutes. After then adding 1-iodobutane (41.3 μL, 0.42 mmol) to the mixture, stirring was continued for 2 hours. Water was added to the reaction mixture, and then ethyl acetate was added. After thoroughly shaking the mixture, the organic layer was separated and the organic layer was washed with brine and dried over anhydrous magnesium sulfate.

The mixture was filtered, and then the solvent in the filtrate was distilled off under reduced pressure.

Dichloromethane (2 mL) was added to the resulting residue, trifluoroacetic acid (2 mL) was added, and the mixture was stirred at room temperature for 1 hour. The solvent in the filtrate was distilled off under reduced pressure.

THF (4 mL) was then added to the resulting residue, tetrahydro-4H-pyran-4-one (59.9 μL, 0.65 mmol) and sodium triacetoxyborohydride (138 mg, 0.65 mmol) were added in that order, and the mixture was stirred at room temperature for 14 hours. A saturated aqueous solution of sodium hydrogencarbonate was added to the reaction mixture, and ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by (NH)silica gel chromatography (mixture of n-heptane and ethyl acetate: n-heptane/ethyl acetate=4/1 then 3/1) to obtain the title compound (94.8 mg, 0.20 mmol).

¹H-NMR (CDCl₃) δ: 0.88 (t, J=7.2 Hz, 3H), 1.32-1.44 (m, 2H), 1.52-1.66 (m, 2H), 1.79-1.86 (m, 2H), 2.92-2.97 (m, 2H), 3.02-3.11 (m, 1H), 3.34-3.41 (m, 2H), 3.47 (s, 3H), 3.80 (s, 3H), 3.85 (s, 3H), 3.96-4.02 (m, 2H), 4.49 (s, 2H), 6.46 (s, 1H), 6.93 (br.s, 1H), 7.09 (br.s, 1H).

Example 14

4-{7-[(Cyclopropylmethyl)(tetrahydrofuran-3-ylmethyl)amino]-6-methoxypyrazolo[5,1-b][1,3]thiazol-3-yl}-3,5-diimethoxybenzonitrile

[Chemical Formula 57]

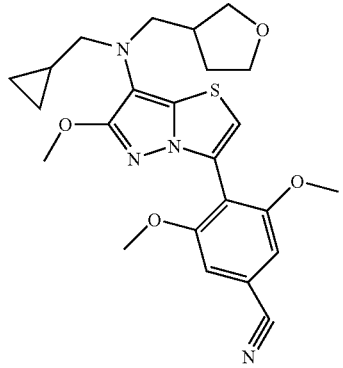

(14a) tert-Butyl[3-(4-cyano-2,6-dimethoxyphenyl)-6-methoxypyrazolo[5,1-b][1,3]thiazol-7-yl]carbamate

[Chemical Formula 58]

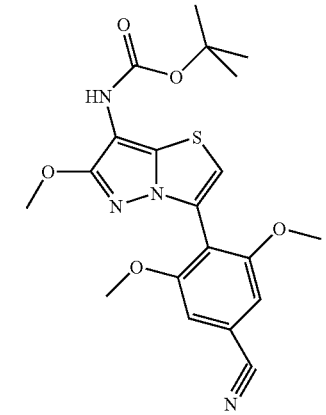

To a mixture of tert-butyl (3-bromo-6-methoxypyrazolo[5,1-b][1,3]thiazol-7-yl)carbamate (461 mg, 1.33 mmol), DME (49 mL) and water (16 mL) were added (4-cyano-2,6-dimethoxyphenyl)boronic acid (412 mg, 2.00 mmol), potassium carbonate (366 mg, 2.66 mmol), triphenylphosphine (174 mg, 0.659 mmol) and palladium acetate (29.8 mg, 0.132 mmol) in that order, and the mixture was stirred at 90° C. (internal temperature) for 2 hours. Water was added to the mixture, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=2/1 then 1/1) to obtain the title compound (296 mg, 0.688 mmol).

$^1$H-NMR (CDCl$_3$) δ: 1.52 (s, 9H), 3.78 (s, 6H), 3.87 (s, 3H), 6.11 (br.s, 1H), 6.50 (s, 1H), 6.91 (s, 2H).

(14b) 4-{7-[(Cyclopropylmethyl)(tetrahydrofuran-3-ylmethyl)amino]-6-methoxypyrazolo[5,1-b][1,3]thiazol-3-yl}-3,5-dimethoxybenzonitrile

[Chemical Formula 59]

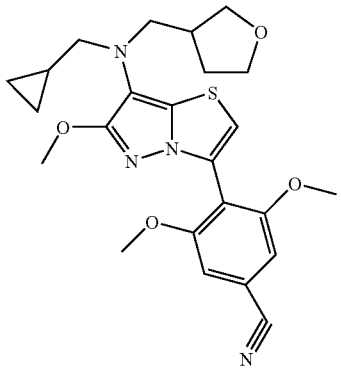

To a mixture of tert-butyl [3-(4-cyano-2,6-dimethoxyphenyl)-6-methoxypyrazolo[5,1-b][1,3]thiazol-7-yl]carbamate (66 mg, 0.153 mmol) and DMF (4 mL) were added sodium hydride (60% dispersion in oil: 7.96 mg, 0.199 mmol) and cyclopropylmethyl bromide (19.3 μL, 0.199 mmol) in that order at room temperature, and the mixture was stirred for 1 hour. Water was added to the mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure.

Dichloromethane (6 mL) was added to the residue, trifluoroacetic acid (1 mL) was added, and the mixture was stirred at room temperature for 1 hour. The solvent in the filtrate was distilled off under reduced pressure.

After then adding methanol (6 mL), and then tetrahydrofuran-3-carboxaldehyde (55.4 μL, 0.306 mmol), acetic acid (1 mL) and α-picolineborane (32.7 mg, 0.306 mmol) in that order to the obtained residue, the mixture was stirred for 1 hour at room temperature. To this mixture was added aqueous 5N sodium hydroxide to approximate neutral pH of the mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=2/1 then 1/1) to obtain the title compound (53.9 mg, 0.115 mmol).

$^1$H-NMR (CDCl$_3$) δ: 0.01-0.10 (m, 2H), 0.36-0.46 (m, 2H), 0.83-0.96 (m, 1H), 1.58-1.71 (m, 1H), 1.90-2.03 (m, 1H), 2.26-2.40 (m, 1H), 2.81 (d, J=6.4 Hz, 2H), 2.95 (dd, J=8.4, 12.0 Hz, 1H), 3.07 (dd, J=6.8, 12.0 Hz, 1H), 3.56 (dd, J=6.0, 8.4 Hz, 1H), 3.65-3.74 (m, 1H), 3.81 (s, 6H), 3.86 (s, 3H), 3.76-3.88 (m, 2H), 6.49 (s, 1H), 6.92 (s, 2H).

Example 15

4-{7-[(Cyclopropylmethyl)(tetrahydro-2H-pyran-4-ylmethyl)amino]-6-methoxypyrazolo[5,1-b][1,3]thiazol-3-yl}-3,5-dimethoxybenzonitrile

[Chemical Formula 60]

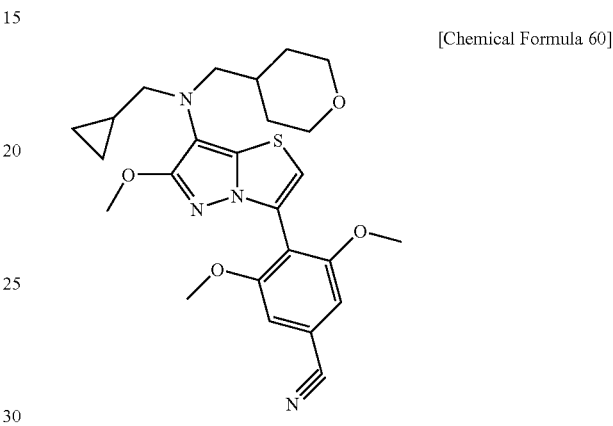

To a mixture of tert-butyl [3-(4-cyano-2,6-dimethoxyphenyl)-6-methoxypyrazolo[5,1-b][1,3]thiazol-7-yl]carbamate (90 mg, 0.21 mmol) and DMSO (0.8 mL) were added powdered sodium hydroxide (16.8 mg 0.42 mmol) and cyclopropylmethyl bromide (30.7 μL, 0.317 mmol) at room temperature, and the mixture was stirred for 1 hour. A saturated aqueous solution of ammonium chloride and ethyl acetate were then added to the reaction mixture. After thoroughly shaking the mixture, the organic layer was separated and the solvent was distilled off with a nitrogen airflow.

Dichloromethane (0.6 mL) was added to the resulting residue, trifluoroacetic acid (0.2 mL) was added and the mixture was stirred at room temperature for 2 hours. The solvent in the mixture was then distilled off with a nitrogen airflow. THF (1 mL) was then added to the resulting residue, tetrahydro-2H-pyran-4-carbaldehyde (36 mg, 0.315 mmol) and sodium triacetoxyborohydride (66.8 mg, 0.315 mmol) were added in that order, and the mixture was stirred at room temperature for 2 hours. A saturated aqueous solution of sodium hydrogencarbonate was added to the mixture, and ethyl acetate was added. After thoroughly shaking the mixture, the organic layer was separated and the solvent was distilled off with a nitrogen airflow. The residue was purified by silica gel column chromatography (mixture of n-heptane and ethyl acetate: n-heptane/ethyl acetate=1/0 then 3/2) to obtain the title compound (71.3 mg, 0.148 mmol).

$^1$H-NMR (CDCl$_3$) δ: 0.00-0.06 (m, 2H), 0.36-0.44 (m, 2H), 0.84-0.94 (m, 1H), 1.21-1.34 (m, 2H), 1.54-1.67 (m, 1H), 1.71-1.80 (m, 2H), 2.80 (d, J=6.8 Hz, 2H), 2.89 (d, J=7.2 Hz, 2H), 3.33 (dt, J=1.6, 11.6 Hz, 2H), 3.82 (s, 6H), 3.86 (s, 3H), 3.90-3.97 (m, 2H), 6.49 (s, 1H), 6.93 (s, 2H).

Example 16

N-(Cyclopropylmethyl)-6-methoxy-N-(tetrahydro-2H-pyran-4-ylmethyl)-3-(2,4,6-trimethoxyphenyl)-pyrazolo[5,1-b][1,3]thiazole-7-amine

[Chemical Formula 61]

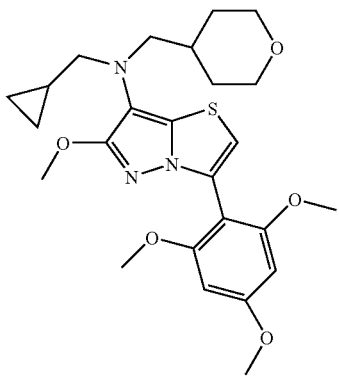

(16a) tert-Butyl(3,5-dimethoxyphenoxy)dimethylsilane

[Chemical Formula 62]

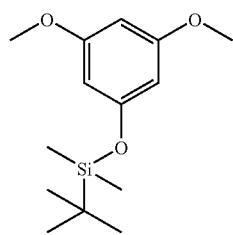

To a mixture of 3,5-dimethoxyphenol (3.00 g, 19.5 mmol) and DMF (45 mL) were added imidazole (2.66 g, 39.0 mmol) and tert-butyldimethylchlorosilane (2.94 g, 19.5 mmol) in that order, and the mixture was stirred for 19.5 hours at room temperature. Water was added to the reaction mixture, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=9/1) to obtain the title compound (4.98 g, 18.6 mmol).

$^1$H-NMR (CDCl$_3$) δ: 0.21 (s, 6H), 0.98 (s, 9H), 3.75 (s, 6H), 6.02 (d, J=2.4 Hz, 2H), 6.11 (t, J=2.4 Hz, 1H).

(16b) (4-{[tert-Butyl(dimethyl)silyl]oxy}-2,6-dimethoxyphenyl)boronic acid

[Chemical Formula 63]

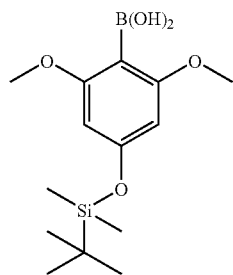

To a mixture of tert-butyl(3,5-dimethoxyphenoxy)dimethylsilane (4.97 g, 18.5 mmol) and THF (50.0 mL) were added N,N,N',N'-tetramethylethylenediamine (3.35 mL, 22.2 mmol) and n-butyllithium (2.77 M solution in n-hexane: 8.01 mL, 22.2 mmol) in that order at room temperature, and the mixture was stirred for 1 hour at room temperature. The mixture was then cooled to −78° C. (internal temperature), and then trimethyl borate (2.48 mL, 22.2 mmol) was added and the temperature was raised to room temperature while stirring. A saturated aqueous solution of ammonium chloride was added to the reaction mixture and then ethyl acetate was added, while cooling on ice. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=4/1) to obtain the title compound (3.50 g, 11.2 mmol).

$^1$H-NMR (CDCl$_3$) δ: 0.25 (s, 6H), 1.00 (s, 9H), 3.86 (s, 6H), 6.11 (s, 2H), 7.04 (s, 2H).

(16c) tert-Butyl[3-(4-hydroxy-2,6-dimethoxyphenyl)-6-methoxypyrazolo[5,1-b][1,3]thiazol-7-yl)]carbamate

[Chemical Formula 64]

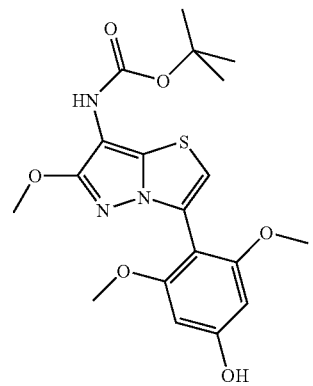

To a mixture of tert-butyl (3-bromo-6-methoxypyrazolo[5,1-b][1,3]thiazol-7-yl)carbamate (400 mg, 1.15 mmol), 1,4-dioxane (26.7 mL) and water (13.3 mL) were added (4-{[tert-butyl(dimethyl)silyl]oxy}-2,6-dimethoxyphenyl)boronic acid (647 mg, 2.07 mmol), potassium carbonate (318 mg, 2.29 mmol) and tetrakis(triphenylphosphine)palladium(0) (133 mg, 0.115 mmol) in that order, and the mixture was stirred for 1 hour at 110° C. (internal temperature). Water was added to the mixture, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=1/1) to obtain the title compound (224 mg, 0.53 mmol).

$^1$H-NMR (CDCl$_3$) δ: 1.54 (s, 9H), 3.61 (s, 6H), 3.99 (s, 3H), 5.93 (s, 2H), 6.10 (br.s, 1H), 6.38 (s, 1H).

(16d) tert-Butyl[6-methoxy-3-(2,4,6-trimethoxyphenyl)pyrazolo[5,1-b][1,3]thiazol-7-yl)]carbamate

[Chemical Formula 65]

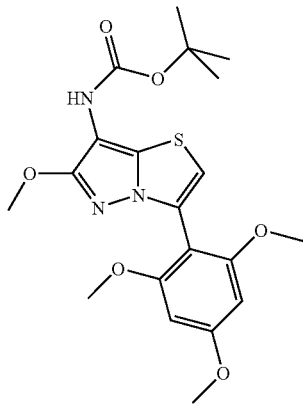

To a mixture of tert-butyl [3-(4-hydroxy-2,6-dimethoxyphenyl)-6-methoxypyrazolo[5,1-b][1,3]thiazol-7-yl)]carbamate (224 mg, 0.531 mmol) and DMF (5.00 mL) were added potassium carbonate (117 mg, 0.85 mmol) and iodomethane (52.9 μL, 0.85 mmol) in that order at room temperature, and the mixture was stirred for 14.5 hours. Water was added to the reaction mixture, and then ethyl acetate was added. After thoroughly shaking the mixture, the organic layer was separated and the organic layer was washed with brine and dried over anhydrous magnesium sulfate. The mixture was then filtered, and the solvent in the filtrate was distilled off under reduced pressure to obtain the title compound (231 mg, 0.53 mmol).

$^1$H-NMR (CDCl$_3$) δ: 1.52 (s, 9H), 3.73 (s, 6H), 3.86 (s, 3H), 3.89 (s, 3H), 6.10 (br.s, 1H), 6.20 (s, 2H), 6.40 (s, 1H).

(16e) N-(Cyclopropylmethyl)-6-methoxy-N-(tetrahydro-2H-pyran-4-ylmethyl)-3-(2,4,6-trimethoxyphenyl)pyrazolo[5,1-b][1,3]thiazole-7-amine

[Chemical Formula 66]

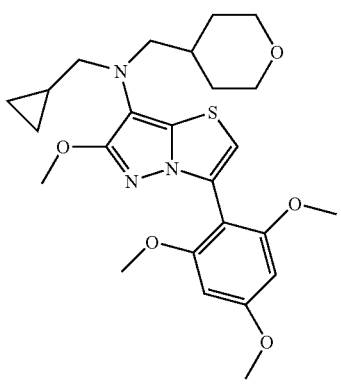

To a mixture of tert-butyl [6-methoxy-3-(2,4,6-trimethoxyphenyl)pyrazolo[5,1-b][1,3]thiazol-7-yl)]carbamate (112 mg, 0.256 mmol) and DMF (2.5 mL) was added sodium hydride (60% dispersion in oil: 16.0 mg, 0.333 mmol) at room temperature, and the mixture was stirred for 30 minutes. After adding cyclopropylmethyl bromide (32.3 μL, 0.333 mmol) to the mixture, stirring was continued for 40 minutes. Water was added to the mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure.

Dichloromethane (2.5 mL) was added to the resulting residue, trifluoroacetic acid (1 mL) was added, and the mixture was stirred at room temperature for 1 hour and 20 minutes. The solvent in the filtrate was distilled off under reduced pressure.

THF (4 mL) was then added to the resulting residue, tetrahydro-2H-pyran-4-carbaldehyde (29.4 mg, 0.257 mmol) and sodium triacetoxyborohydride (54.5 mg, 0.257 mmol) were added in that order, and the mixture was stirred at room temperature for 2 hours. A saturated aqueous solution of sodium hydrogencarbonate was added to the mixture while cooling on ice, and ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=9/1 then 3/2) to obtain the title compound (75.0 mg, 0.16 mmol).

$^1$H-NMR (CDCl$_3$) δ: 0.00-0.06 (m, 2H), 0.35-0.43 (m, 2H), 0.87-0.97 (m, 1H), 1.20-1.36 (m, 2H), 1.55-1.69 (m, 1H), 1.71-1.81 (m, 2H), 2.80 (dd, J=6.4 Hz, 2H), 2.89 (d, J=6.8 Hz, 2H), 3.27-3.39 (m, 2H), 3.76 (s, 6H), 3.87 (s, 3H), 3.88 (s, 3H), 3.88-3.98 (m, 2H), 6.23 (s, 2H), 6.37 (s, 1H).

Example 17

3-{4-[(Cyclobutyloxy)methyl]-2,6-dimethoxyphenyl}-6-methoxy-N-propyl-N-(tetrahydro-2H-pyran-4-yl)pyrazolo[5,1-b][1,3]thiazole-7-amine

[Chemical Formula 67]

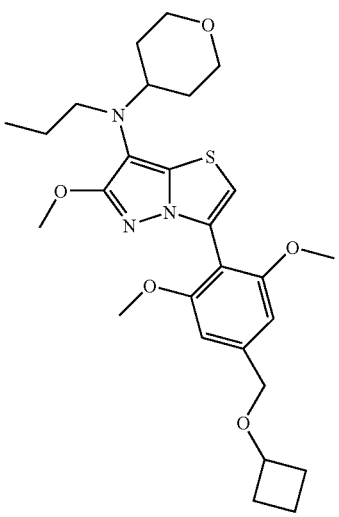

(17a) (4-Bromo-3,5-dimethoxyphenyl)methanol

[Chemical Formula 68]

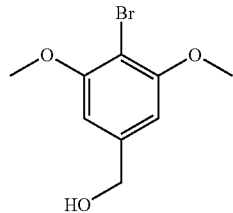

To a mixture of 4-bromo-3,5-dimethoxybenzoic acid (50.0 g, 192 mmol) and THF (1 L) was added borane-methyl sulfide (27.1 mL, 286 mmol) while cooling on ice, and the mixture was heated to reflux for 1 hour. Water was slowly added to the mixture while cooling on ice, and then the solvent in the mixture was distilled off under reduced pressure. Water and ethyl acetate were added to the residue. After thoroughly shaking the mixture, the organic layer was separated and the organic layer was washed with brine and dried over anhydrous magnesium sulfate. The mixture was then filtered, and the solvent in the filtrate was distilled off under reduced pressure to obtain the title compound (47.3 g, 191 mmol).

$^1$H-NMR (CDCl$_3$) δ: 1.80 (s, 1H), 3.91 (s, 6H), 4.68 (s, 2H), 6.60 (s, 2H).

(17b) 2-Bromo-5-(chloromethyl)-1,3-dimethoxybenzene

[Chemical Formula 69]

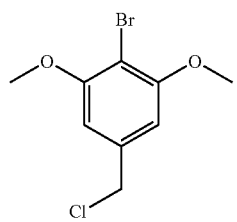

To a mixture of (4-bromo-3,5-dimethoxyphenyl)methanol (10.0 g, 40.6 mmol) and dichloromethane (100 mL) were added triethylamine (12.4 mL, 89.3 mmol) and methanesulfonyl chloride (3.46 mL, 44.7 mmol) in that order while cooling on ice, and the mixture was stirred at room temperature for 14 hours. Water was added to the mixture, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=4/1) to obtain the title compound (2.47 g, 9.30 mmol).

$^1$H-NMR (CDCl$_3$) δ: 3.92 (s, 6H), 4.55 (s, 2H), 6.60 (s, 2H).

(17c) 2-Bromo-5-[(cyclobutyloxy)methyl]-1,3-dimethoxybenzene

[Chemical Formula 70]

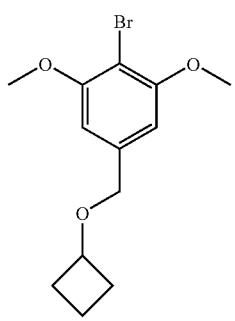

To a mixture of cyclobutyl alcohol (4.16 g, 57.7 mmol) and DMF (30 mL) was added sodium hydride (60% dispersion in oil: 2.31 g, 57.7 mmol) while cooling on ice, and the mixture was stirred at room temperature for 1 hour. To this mixture was slowly added dropwise a mixture of 2-bromo-5-(chloromethyl)-1,3-dimethoxybenzene (2.47 g, 9.3 mmol) and DMF (30 mL), and the resulting mixture was stirred at room temperature for 1 hour. Water was added to the mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=4/1) to obtain the title compound (2.39 g, 7.94 mmol).

$^1$H-NMR (CDCl$_3$) δ: 1.43-1.60 (m, 1H), 1.65-1.80 (m, 1H), 1.92-2.08 (m, 2H), 2.15-2.28 (m, 2H), 3.90 (s, 6H), 3.96-4.07 (m, 1H), 4.38 (s, 2H), 6.56 (s, 2H).

(17d) {4-[(Cyclobutyloxy)methyl]-2,6-dimethoxyphenyl}boronic acid

[Chemical Formula 71]

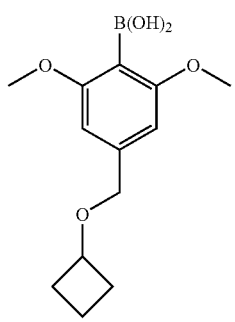

To a mixture of 2-bromo-5-[(cyclobutyloxy)methyl]-1,3-dimethoxybenzene (2.39 g, 7.94 mmol) and THF (20 mL) was added n-butyllithium (2.73 M solution in n-hexane: 3.49 mL, 9.53 mmol) at −78° C. (internal temperature), and the mixture was stirred for 1 hour. After then adding trimethyl borate (1.07 mL, 9.53 mmol) to the mixture, the temperature was slowly raised to room temperature while stirring. A saturated aqueous solution of ammonium chloride was added to the reaction mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. Heptane (30 mL) was added to the residue, the precipitated solid was collected by filtration and dried under reduced pressure to obtain the title compound (905 mg, 3.40 mmol).

$^1$H-NMR (CDCl$_3$) δ: 1.45-1.60 (m, 1H), 1.67-1.80 (m, 1H), 1.94-2.08 (m, 2H), 2.18-2.30 (m, 2H), 3.92 (s, 6H), 3.96-4.07 (m, 1H), 4.41 (s, 2H), 6.61 (s, 2H), 7.18 (s, 2H).

(17e) tert-Butyl (3-{4-[(cyclobutyloxy)methyl]-2,6-dimethoxyphenyl}-6-methoxypyrazolo[5,1-b][1,3]thiazol-7-yl)carbamate

[Chemical Formula 72]

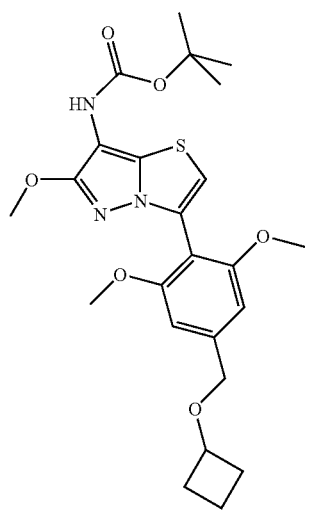

To a mixture of tert-butyl (3-bromo-6-methoxypyrazolo[5,1-b][1,3]thiazol-7-yl)carbamate (987 mg, 2.83 mmol), DME (80 mL) and water (28 mL) were added {4-[(cyclobutyloxy)methyl]-2,6-dimethoxyphenyl}boronic acid (904 mg, 3.4 mmol), potassium carbonate (785 mg, 5.68 mmol), triphenylphosphine (370 mg, 1.42 mmol) and palladium acetate (63.7 mg, 0.282 mmol) in that order, and the mixture was stirred at 90° C. (internal temperature) for 3 hours. Water was added to the reaction mixture, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=2/1) to obtain the title compound (1.24 g, 2.53 mmol).

$^1$H-NMR (CDCl$_3$) δ: 1.52 (s, 9H), 1.46-1.62 (m, 1H), 1.66-1.81 (m, 1H), 1.96-2.10 (m, 2H), 2.20-2.32 (m, 2H), 3.75 (s, 6H), 3.87 (s, 3H), 4.02-4.13 (m, 1H), 4.43 (s, 2H), 6.08 (br.s, 1H), 6.41 (s, 1H), 6.62 (s, 2H).

(17f) 3-{4-[(Cyclobutyloxy)methyl]-2,6-dimethoxyphenyl}-6-methoxy-N-propyl-N-(tetrahydro-2H-pyran-4-yl)pyrazolo[5,1-b][1,3]thiazole-7-amine

[Chemical Formula 73]

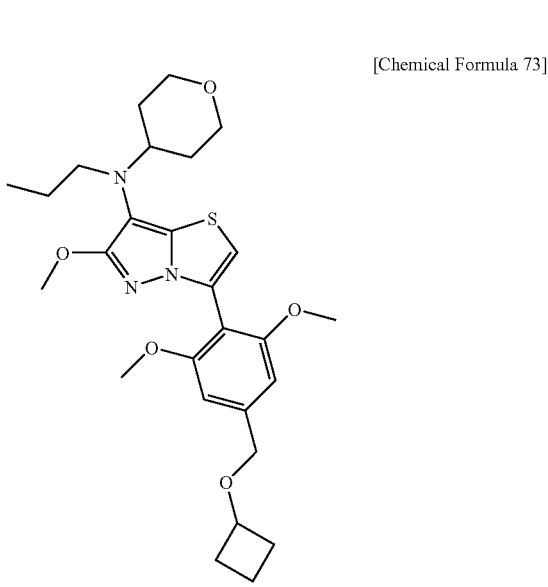 [SMILES: CCCN(c1c(OC)nn2c(-c3c(OC)cc(COC4CCC4)cc3OC)csc12)C1CCOCC1]

To a mixture of tert-butyl (3-{4-[(cyclobutyloxy)methyl]-2,6-dimethoxyphenyl}-6-methoxypyrazolo[5,1-b][1,3]thiazol-7-yl)carbamate (123 mg, 0.251 mmol) and DMF (6 mL) was added sodium hydride (60% dispersion in oil: 13.0 mg, 0.326 mmol) at room temperature, and the mixture was stirred for 30 minutes. After then adding 1-iodopropane (35.4 μL, 0.326 mmol) to the mixture, stirring was continued for 30 minutes. Water was added to the mixture while cooling on ice, and then ethyl acetate was added. After thoroughly shaking the mixture, the organic layer was separated and the organic layer was washed with brine and dried over anhydrous magnesium sulfate. The mixture was filtered, and then the solvent in the filtrate was distilled off under reduced pressure.

Dichloromethane (6 mL) was added to the resulting residue, trifluoroacetic acid (1 mL) was added, and the mixture was stirred at room temperature for 1 hour. The solvent in the filtrate was distilled off under reduced pressure.

THF (10 mL) was then added to the resulting residue, tetrahydro-4H-pyran-4-one (49 μL, 0.501 mmol), acetic acid (1 mL) and sodium triacetoxyborohydride (106 mg, 0.501 mmol) were added in that order, and the mixture was stirred at room temperature for 14 hours. To this mixture there was added aqueous 5N sodium hydroxide to approximate neutral pH of the mixture while cooling on ice, and then ethyl acetate was added.

After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (mixture of n-heptane and ethyl acetate: n-heptane/ethyl acetate=1/1) to obtain the title compound (98.0 mg, 0.19 mmol).

$^1$H-NMR (CDCl$_3$) δ: 0.87 (t, J=7.2 Hz, 3H), 1.32-1.44 (m, 2H), 1.46-1.66 (m, 3H), 1.69-1.87 (m, 3H), 1.98-2.11 (m, 2H), 2.21-2.33 (m, 2H), 2.94 (t, J=7.2 Hz, 2H), 3.00-3.10 (m, 1H), 3.38 (td, J=1.6, 11.6 Hz, 2H), 3.79 (s, 6H), 3.85 (s, 3H), 3.94-4.02 (m, 2H), 4.03-4.13 (m, 1H), 4.44 (s, 2H), 6.40 (s, 1H), 6.64 (s, 2H).

Example 1 x

N-Butyl-3-[2,6-dimethoxy-4-(methoxymethyl)phenyl]-6-methoxy-N-(tetrahydro-2H-pyran-4-yl)pyrazolo[5,1-b][1,3]thiazole-7-amine hydrobromide To a mixture of N-butyl-3-[2,6-dimethoxy-4-(methoxymethyl)phenyl]-6-methoxy-N-(tetrahydro-2H-pyran-4-yl)pyrazolo[5,1-b][1,3]thiazole-7-amine (6 mg) and methanol (1 mL) was added hydrobromic acid (8.84M, 2.0 µL), and the mixture was stirred at room temperature for 1 hour and the solvent was distilled off under reduced pressure. Methanol (1 mL) was added to the residue and the solvent was distilled off under reduced pressure. Ethyl acetate (1 mL) was added to the resultant residue and the solvent was distilled off under reduced pressure and dried to obtain the titled compound (6.0 mg).

Example 2x

N-Butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine hydrobromide To N-butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine (1.02 g) was added acetone (2 mL) warmed by hot water, then hydrobromic acid (8.84M, 240 µL) was added, and the mixture was stirred. The solvent in the mixture was partially removed by blowing nitrogen stream, and the mixture was further stirred.

The mixture was allowed to stand at room temperature under reduced pressure for 13 hours to remove the solvent in the residue. The resultant residue was finely triturated, acetone (2 mL) and heptane (2 mL) were added, and the mixture was shaken under sonication (a bath-type sonicator) for 1 minute. The vessel was protected from light and sealed tightly, and the mixture was stirred for one day.

The precipitate in the mixture was collected by suction filtration, and allowed to stand at room temperature under reduced pressure to remove the solvent in the residue. To the residue was added acetone (20 mL), and heptane (3 mL) was added and the mixture was stirred for several minutes. Heptane (5 mL) was added, the vessel was protected from light, and the mixture was stirred for one day. The precipitate in the mixture was collected by suction filtration, and allowed to stand at room temperature under reduced pressure to remove the solvent in the residue and the title compound (701.17 mg) was obtained.

Example 2y

N-Butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine phosphate To N-butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine (2.99 g) were added ethanol (7 mL) warmed by hot water and phosphoric acid (14.6M, 410 µL). Heptane was added by 1 mL and the volume totaled 30 mL. The mixture was stirred for 1 hour under shading.

The precipitate in the mixture was collected by suction filtration, allowed to stand at room temperature under reduced pressure for 1 week to remove the solvent in the residue and dried by heating at 60° C. for 1.5 hours to obtain the title compound (4.10 g).

Example 3x

N-(2-Cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine phosphate To a mixture of N-(2-cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine (757.0 mg), ethanol (10 mL) and ethyl acetate (5 mL) was added phosphoric acid (14.6M, 101 µL). The mixture was stirred at room temperature for 5 minutes and the solvent was removed by blowing nitrogen stream and dried to obtain the title compound (856.0 mg).

Example 3y

N-(2-Cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine methanesulfonate To a mixture of N-(2-cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine (16.2 mg) and ethyl acetate (0.5 mL) was added methanesulfonic acid (2.05 µL). The mixture was stirred at room temperature for 1 hour and the solvent was removed by blowing nitrogen stream and dried to obtain the title compound (19.2 mg).

Example 3z

N-(2-Cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine sulfate To a mixture of N-(2-cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine (59.6 mg), ethanol (2 mL) and ethyl acetate (1 mL) was added concentrated sulfuric acid (6.18 µL). The mixture was stirred at room temperature for 2 hours and the solvent was removed by blowing nitrogen stream and dried to obtain the title compound (66.3 mg).

Example 4x

N-(Cyclobutylmethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine methanesulfonate To a mixture of N-(cyclobutylmethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine (13.4 mg) and ethyl acetate (0.5 mL) was added methanesulfonic acid (1.69 µL). The mixture was stirred at room temperature for 1 hour and the solvent was removed by blowing nitrogen stream and dried to obtain the title compound (15.9 mg).

Example 5x

N-(Cyclopropylmethyl)-3-[4-(ethoxymethyl)-2,6-dimethoxyphenyl]-6-methoxy-N-(tetrahydro-2H-pyran-3-yl)pyrazolo[5,1-b][1,3]thiazole-7-amine sulfate To a mixture of N-(cyclopropylmethyl)-3-[4-(ethoxymethyl)-2,6-dimethoxyphenyl]-6-methoxy-N-(tetrahydro-2H- pyran-3-yl)pyrazolo[5,1-b][1,3]thiazole-7-amine (42.0 mg), ethanol (2 mL) and ethyl acetate (1 mL) was added concentrated sulfuric acid (4.46 μL). The mixture was stirred at room temperature for 2 hours and the solvent was removed by blowing nitrogen stream and dried to obtain the title compound (45.7 mg).

Example 6x

3-[4-(Ethoxymethyl)-2,6-dimethoxyphenyl]-6-methoxy-N-propyl-N-(tetrahydro-2H-pyran-3-yl)pyrazolo[5,1-b][1,3]thiazole-7-amine sulfate To a mixture of 3-[4-(ethoxymethyl)-2,6-dimethoxyphenyl]-6-methoxy-N-propyl-N-(tetrahydro-2H-pyran-3-yl)pyrazolo[5,1-b][1,3]thiazole-7-amine (8.1 mg) and ethanol (2 mL) was added concentrated sulfuric acid (0.88 μL). The mixture was stirred at room temperature for 2 hours and the solvent was removed by blowing nitrogen stream and dried to obtain the title compound (9.8 mg).

Example 7x

N-(Cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine sulfate To a mixture of N-(cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine (99.0 mg), ethanol (2 mL) and ethyl acetate (1 mL) was added concentrated sulfuric acid (10.5 μL). The mixture was stirred at room temperature for 2 hours and the solvent was distilled off under reduced pressure and dried to obtain the title compound (120.4 mg).

Example 7y

N-(Cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine methanesulfonate To a mixture of N-(cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine (26.2 mg) and ethyl acetate (1.0 mL) was added methanesulfonic acid (3.40 μL). The mixture was stirred at room temperature for 1 hour and the solvent was removed by blowing nitrogen stream and dried to obtain the title compound (31.2 mg).

Example 8x

3-[2,6-Dimethoxy-4-(methoxymethyl)phenyl]-6-methoxy-N-pentyl-N-(tetrahydro-2H-pyran-4-yl)pyrazolo[5,1-b][1,3]thiazole-7-amine methanesulfonate To a mixture of 3-[2,6-dimethoxy-4-(methoxymethyl)phenyl]-6-methoxy-N-pentyl-N-(tetrahydro-2H-pyran-4-yl)pyrazolo[5,1-b][1,3]thiazole-7-amine (12.2 mg) and ethyl acetate (0.5 mL) was added methanesulfonic acid (1.58 μL). The mixture was stirred at room temperature for 1 hour and the solvent was removed by blowing nitrogen stream and dried to obtain the title compound (14.5 mg).

Example 9x

N-(Cyclopropylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine hydrochloride To a mixture of N-(cyclopropylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine (8.38 mg) and ethyl acetate (0.5 mL) was added hydrochloric acid in diethyl ether (1M, 17.2 μL). The mixture was stirred at room temperature for 1.5 hours and the solvent was removed by blowing nitrogen stream and dried to obtain the title compound (9.22 mg).

Example 10x

3-[2,6-Dimethoxy-4-(methoxymethyl)phenyl]-6-methoxy-N-propyl-N-(tetrahydro-2H-pyran-4-yl)pyrazolo[5,1-b][1,3]thiazole-7-amine hydrochloride To a mixture of 3-[2,6-dimethoxy-4-(methoxymethyl)phenyl]-6-methoxy-N-propyl-N-(tetrahydro-2H-pyran-4-yl)pyrazolo[5,1-b][1,3]thiazole-7-amine (6.98 mg) and ethyl acetate (0.5 mL) was added hydrochloric acid in diethyl ether (1M, 14.7 μL). The mixture was stirred at room temperature for 1.5 hours and the solvent was removed by blowing nitrogen stream and dried to obtain the title compound (7.84 mg).

Example 11x

N-(Cyclopropylmethyl)-3-[2,6-dimethoxy-4-(methoxymethyl)phenyl]-6-methoxy-N-(tetrahydro-2H-pyran-3-yl)pyrazolo[5,1-b][1,3]thiazole-7-amine phosphate To a mixture of N-(cyclopropylmethyl)-3-[2,6-dimethoxy-4-(methoxymethyl)phenyl]-6-methoxy-N-(tetrahydro-2H-pyran-3-yl)pyrazolo[5,1-b][1,3]thiazole-7-amine (30.0 mg) and ethyl acetate (0.6 mL) was added phosphoric acid (14.6M, 4.00 μL). The mixture was stirred at room temperature for 5 minutes and the solvent was removed by blowing nitrogen stream and dried to obtain the title compound (35.8 mg).

Example 12x

3-[2,6-Dimethoxy-4-(methoxymethyl)phenyl]-6-methoxy-N-[(2-methylcyclopropyl)methyl]-N-(tetrahydro-2H-pyran-4-yl)pyrazolo[5,1-b][1,3]thiazole-7-amine methanesulfonate To a mixture of 3-[2,6-dimethoxy-4-(methoxymethyl)phenyl]-6-methoxy-N-[(2-methylcyclopropyl)methyl]-N-(tetrahydro-2H-pyran-4-yl)pyrazolo[5,1-b][1,3]thiazole-7-amine (14.6 mg) and ethyl acetate (0.5 mL) was added methanesulfonic acid (1.90 μL). The mixture was stirred at room temperature for 1 hour and the solvent was removed by blowing nitrogen stream and dried to obtain the title compound (17.4 mg).

Example 13x

3-[2-Chloro-6-methoxy-4-(methoxymethyl)phenyl]-6-methoxy-N-propyl-N-(tetrahydro-2H-pyran-4-yl)pyrazolo[5,1-b][1,3]thiazole-7-amine methanesulfonate To a mixture of 3-[2-chloro-6-methoxy-4-(methoxymethyl)phenyl]-6-methoxy-N-propyl-N-(tetrahydro-2H-pyran-4-yl)pyrazolo[5,1-b][1,3]thiazole-7-amine (10.7 mg) and ethyl acetate (0.5 mL) was added methanesulfonic acid (1.45 µL). The mixture was stirred at room temperature for 1 hour and the solvent was removed by blowing nitrogen stream and dried to obtain the title compound (12.8 mg).

Example 14x

4-{7-[(Cyclopropylmethyl)(tetrahydrofuran-3-ylmethyl)amino]-6-methoxypyrazolo[5,1-b][1,3]thiazol-3-yl}-3,5-dimethoxybenzonitrile hydrobromide To a mixture of 4-{7-[(cyclopropylmethyl)(tetrahydrofuran-3-ylmethyl)amino]-6-methoxypyrazolo[5,1-b][1,3]thiazol-3-yl}-3,5-dimethoxybenzonitrile (8.0 mg) and methanol (1 mL) was added hydrobromic acid (8.84M, 2.4 µL), and the mixture was stirred at room temperature for 1 hour and the solvent was distilled off under reduced pressure. Methanol (1 mL) was added to the residue and the solvent was distilled off under reduced pressure. Ethyl acetate (1 mL) was added to the resultant residue and the solvent was distilled off under reduced pressure and dried to obtain the titled compound (8.0 mg).

Example 15x

4-{7-[(Cyclopropylmethyl)(tetrahydro-2H-pyran-4-ylmethyl)amino]-6-methoxypyrazolo[5,1-b][1,3]thiazol-3-yl}-3,5-dimethoxybenzonitrile hydrochloride To a mixture of 4-{7-[(cyclopropylmethyl)(tetrahydro-2H-pyran-4-ylmethyl)amino]-6-methoxypyrazolo[5,1-b][1,3]thiazol-3-yl}-3,5-dimethoxybenzonitrile (26.4 mg) and ethyl acetate (0.5 mL) was added hydrochloric acid in diethyl ether (1M, 54.7 µL). The mixture was stirred at room temperature for 1 hour and the solvent was removed by blowing nitrogen stream and dried to obtain the title compound (28.4 mg).

Example 16x

N-(Cyclopropylmethyl)-6-methoxy-N-(tetrahydro-2H-pyran-4-ylmethyl)-3-(2,4,6-trimethoxyphenyl)-pyrazolo[5,1-b][1,3]thiazole-7-amine hydrochloride To a mixture of N-(Cyclopropylmethyl)-6-methoxy-N-(tetrahydro-2H-pyran-4-ylmethyl)-3-(2,4,6-trimethoxyphenyl)-pyrazolo[5,1-b][1,3]thiazole-7-amine (6.51 mg) and ethyl acetate (0.5 mL) was added hydrochloric acid in diethyl ether (1M, 13.4 µL). The mixture was stirred at room temperature for 1.5 hours and the solvent was removed by blowing nitrogen stream and dried to obtain the title compound (7.41 mg).

Example 17x

3-{4-[(Cyclobutyloxy)methyl]-2,6-dimethoxyphenyl}-6-methoxy-N-propyl-N-(tetrahydro-2H-pyran-4-yl)pyrazolo[5,1-b][1,3]thiazole-7-amine phosphate To a mixture of 3-{4-[(cyclobutyloxy)methyl]-2,6-dimethoxyphenyl}-6-methoxy-N-propyl-N-(tetrahydro-2H-pyran-4-yl)pyrazolo[5,1-b][1,3]thiazole-7-amine (30.0 mg) and ethyl acetate (0.6 mL) was added phosphoric acid (14.6M, 4.00 µL). The mixture was stirred at room temperature for 5 minutes and the solvent was removed by blowing nitrogen stream and dried to obtain the title compound (36.1 mg).

Pharmacological Test Example

The binding capacities of the compounds of the invention for CRF1 receptor (CRFR1) were evaluated. The test methods and results were as described below.

Test Example 1

CRFR1 Binding Test (1) Preparation of CRFR1-Expressing Cells

The membrane fraction of human CRFR1 high-expressing cells was used as the material for a CRFR1 binding experiment. The CRFR1-expressing cells were prepared in the following manner. The full-length CRFR1 gene was obtained by PCR using human brain cDNA library (QuickClone™ Clontech). The obtained DNA fragment was inserted into a cloning vector and the nucleotide sequence was confirmed. cDNA having the proper nucleotide sequence was linked to an expression vector (pcDNA3.1™, Invitrogen). The CRFR1 expression vector was introduced into HEK293 cell, and the resistant cells which proliferated in culture medium containing G418 (1 mg/ml) were cloned by the limiting dilution method. Out of the cloned cells, cells having high binding affinity between the membrane fraction per unit of protein and sauvagine were selected according to the following binding experiment. And the selected cells were used for the experiments.

(2) Preparation of Membrane Fraction

The cloned cells obtained in (1) were collected and suspended in ice-cooled membrane buffer (50 mM Tris-HCl, 5 mM $MgCl_2$, 2 mM EGTA, 1 mM DTT, protease inhibitor cocktail (COMPLETE™, Roche Diagnostics) pH 7.3), and then the cells were disrupted with a Polytron (KINEMATICA) while cooling on ice (level 5, 10 seconds, 2-5 times, ice-cooling) and then centrifuged (2,000 rpm, 5 minutes, 4° C.), after which the supernatant was collected. Membrane buffer was added to the precipitate, and the mixture was subjected to Polytron treatment (same conditions as above) and centrifuged (same conditions as above), and the obtained supernatant was collected and combined with the previous supernatant. This was centrifuged (13,000 rpm (18,000×g), 30 minutes, 4° C.) to prepare cell membranes. The precipitated cell membranes were suspended in membrane buffer and disrupted with a Polytron (level 5, 10 seconds, 3-5 times, ice-cooling) to prepare a dispersed suspension. The protein assay was performed.

The following method (1) or (2) was performed for use as the cell membrane fraction.

(1) The above dispersed suspension was diluted with membrane buffer containing 0.1% BSA to a protein concentration of 200 µg/ml, for use as the cell membrane fraction (2) The above dispersed suspension was frozen for preservation, and if needed, thawed, re-dispersed and diluted for used as the cell membrane fraction.

(3) Binding Experiment:

A binding competition experiment with CRF was conducted by the SPA (GE Healthcare) method using a 96-well plate. A mixture of 5 µg of the cell membrane fraction protein, 1 mg of SPA beads and 100 pM $^{125}$I-CRF (Perkin Elmer) was allowed to stand at room temperature for at least 2 hours in the presence of a test compound, and the radioactivity of each well after centrifugation (1,200 rpm (260×g), 5 minutes, room temperature) was measured with a TopCount (registered trademark; Perkin Elmer).

(4) Calculation of Binding Capacity

The radioactivity with addition of a 4,000-fold excess of non-radioactive sauvagine as the nonspecific binding was subtracted from each value, and the resulting value was expressed as a percentage (% of control), with 100% as the radioactivity without addition of the test compound (control). The $IC_{50}$ value was calculated from a binding inhibition curve drawn with test compound concentration on the horizontal axis and % (% of control) on the vertical axis.

<Test Results>

As shown by the following table, the compounds of the invention exhibit excellent binding capacity for CRFR1.

TABLE 1

| Compound No. (Example No.) | CRF1 receptor binding capacity $IC_{50}$ (nM) |
|---|---|
| 1 | 52 |
| 2 | 70 |
| 3 | 65 |
| 4 | 34 |
| 5 | 29 |
| 6 | 39 |
| 7 | 46 |
| 8 | 63 |
| 9 | 101 |
| 10 | 98 |
| 11 | 37 |
| 12 | 82 |
| 13 | 63 |
| 14 | 90 |
| 15 | 70 |
| 16 | 29 |
| 17 | 36 |

Test Example 2

Evaluation of Anxiolytic Effect by Mice in Light/Dark Box Test in Mice (1) Test Procedure:

The light/dark box test in mice was carried out according to a modified method of Belzung C., Misslin R., Vogel E. et al. (Reference; Behavioural effects of the benzodiazepine receptor partial agonist RO16-6028 in mice, Psychopharmacology, 97, 388-391, 1989). The test apparatus used was a light/dark box comprising a covered black acrylic box (dark box; 15×10×20 cm), an uncovered white acrylic box (light box; 15×20×20 cm) and a black acrylic tunnel (10×7×4.5 cm) which connects dark box and light box and enables a mouse to freely move back and forth between the dark box and light box. In this test apparatus, however, a transparent acrylic polymer was used for the front side (20×20 cm) and back side (20×20 cm) of the light box to allow observation of the behavior. After setting illumination so that the light intensity of the floor of the light box was 150 Lux, 5-week-old male Balb/c mice (purchased from Nihon Charles River) were introduced into the dark box at the beginning of the test. For the test, the tested compound was suspended in 5% dimethylsulfoxide, 5% Cremopor EL and 90% physiological saline and orally administered to the test animals one hour prior to the start of the test.

(2) Calculation of Anxiolytic Effect:

The behavior of the mice was observed for 5 minutes after start of the test. The time spent in the light box was measured as an index of the anxiolytic effect, with "spend in the light box" defined as the state in which all limbs of the mice were on the floor of the light box. The minimum dose which significantly prolonged the time spent in the light box in comparison with that of vehicle-treated group was determined as the minimum effective dose (MED). The statistical significance between the vehicle-treated group and the test compound-treated groups was analyzed by one way analysis of variance followed by Dunnett multiple comparison when multiple doses were set for the same test, and by the Mann-Whitney U test when only one dose was set.

<Test Results>

The compounds of Examples 1, 2, 3, 4, 5, 9, 10, 13 and 14 exhibited an excellent anxiolytic effects in the light/dark box test in mice, with statistically significant effects being observed at 30 mg/kg (oral administration).

TABLE 2

| Compound No. (Example No.) | Effective Dose (mg/kg) |
|---|---|
| 1 | 30 |
| 2 | 30 |
| 3 | 30 |
| 4 | 30 |
| 5 | 30 |
| 9 | 30 |
| 10 | 30 |
| 13 | 30 |
| 14 | 30 |

INDUSTRIAL APPLICABILITY

According to the invention it is possible to provide pharmaceutical compositions comprising 3-phenylpyrazolo[5,1-b]thiazole compounds or salts thereof, which exhibit CRF receptor antagonism. The compounds or salts thereof according to the invention have excellent CRF receptor antagonism, and sufficient pharmacological activity, safety and pharmacokinetic properties as drugs.

The pharmaceutical compositions of the invention are useful for treatment or prevention of diseases associated with CRF and/or CRF receptors, and are particularly useful as therapeutic or prophylactic agents for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia.

What is claimed is:

1. A compound represented by the following formula (I) or salt thereof,

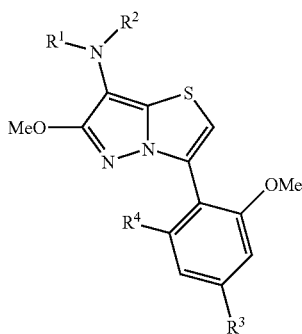

(I)

wherein

R¹ represents the formula -A¹¹-A¹²;

R² represents tetrahydrofurylmethyl, tetrahydropyranylmethyl or tetrahydropyranyl;

A¹¹ represents a single bond, methylene or 1,2-ethylene;

A¹² represents C1-6 alkyl or C3-6 cycloalkyl, or C3-6 cycloalkyl having methyl;

R³ represents methoxy, cyano, cyclobutyloxymethyl, methoxymethyl or ethoxymethyl; and R⁴ represents methoxy or chlorine.

2. A compound or salt thereof as claimed in claim 1, wherein R² is tetrahydropyran-4-yl, tetrahydropyran-3-yl, (tetrahydropyran-4-yl)methyl or (tetrahydrofuran-3-yl)methyl.

3. A compound or salt thereof as claimed in claim 1 or 2, wherein R¹ is n-propyl, n-butyl, n-pentyl, cyclopropylmethyl, cyclobutylmethyl, 2-(cyclopropyl)ethyl or (2-methylcyclopropyl)methyl.

4. A therapeutic agent for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, or dementia, which comprises a compound or salt thereof according to claim 1.

5. N-Butyl-3-[2,6-dimethoxy-4-(methoxymethyl)phenyl]-6-methoxy-N-(tetrahydro-2H-pyran-4-yl)pyrazolo[5,1-b][1,3]thiazole-7-amine or salt thereof.

6. N-Butyl-3-[4-(ethoxymethyl)-2,6-dimethoxyphenyl]-6-methoxy-N-(tetrahydro-2H-pyran-4-yl)pyrazolo[5,1-b][1,3]thiazole-7-amine or salt thereof.

7. N-(2-Cyclopropylethyl)-3-[4-(ethoxymethyl)-2,6-dimethoxyphenyl]-6-methoxy-N-(tetrahydro-2H-pyran-4-yl)pyrazolo[5,1-b][1,3]thiazole-7-amine or salt thereof.

8. 3-[4-(Ethoxymethyl)-2,6-dimethoxyphenyl]-6-methoxy-N-propyl-N-(tetrahydro-2H-pyran-3-yl)pyrazolo[5,1-b][1,3]thiazole-7-amine or salt thereof.

9. N-(Cyclobutylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine or salt thereof.

10. N-(Cyclopropylmethyl)-3-[2,6-dimethoxy-4-(methoxymethyl)phenyl]-6-methoxy-N-(tetrahydro-2H-pyran-4-yl)pyrazolo[5,1-b][1,3]thiazole-7-amine or salt thereof.

11. 3-[2,6-Dimethoxy-4-(methoxymethyl)phenyl]-6-methoxy-N-propyl-N-(tetrahydro-2H-pyran-4-yl)pyrazolo[5,1-b][1,3]thiazole-7-amine or salt thereof.

12. 3-[2-Chloro-6-methoxy-4-(methoxymethyl)phenyl]-6-methoxy-N-propyl-N-(tetrahydro-2H-pyran-4-yl)pyrazolo[5,1-b][1,3]thiazole-7-amine or salt thereof.

13. 4-{7-[(Cyclopropylmethyl)(tetrahydrofuran-3-ylmethyl)amino]-6-methoxypyrazolo[5,1-b][1,3]thiazol-3-yl}-3,5-dimethoxybenzonitrile or salt thereof.

14. N-(Cyclopropylmethyl)-6-methoxy-N-(tetrahydro-2H-pyran-4-ylmethyl)-3-(2,4,6-trimethoxyphenyl)-pyrazolo[5,1-b][1,3]thiazole-7-amine or salt thereof.

15. A pharmaceutical composition comprising a compound or salt thereof according to claim 1 as an active ingredient.

16. A therapeutic agent for depression, depressive symptoms, anxiety or irritable bowel syndrome, comprising a compound or salt thereof according to claim 1.

17. A method for treatment of depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, or dementia, comprising administering to a patient, a compound or salt thereof according to claim 1.

18. A method for treatment of depression, depressive symptoms, anxiety or irritable bowel syndrome, comprising administering to a patient, a compound or salt thereof according to claim 1.

19. A compound or salt thereof according to claim 1 for treatment of depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, or dementia.

20. A compound or salt thereof according to claim 1 for treatment of depression, depressive symptoms, anxiety or irritable bowel syndrome.

* * * * *